United States Patent
Becker et al.

(10) Patent No.: US 10,626,087 B2
(45) Date of Patent: Apr. 21, 2020

(54) INDOLINE AND TETRAHYDROQUINOLINE SULFONYL INHIBITORS OF DIMETALLOENZYMES AND USE OF THE SAME

(71) Applicants: LOYOLA UNIVERSITY OF CHICAGO, Chicago, IL (US); Board of Regents, The University of Texas System, Austin, TX (US)

(72) Inventors: Daniel Paul Becker, Glenview, IL (US); Cory Reidl, Franklin Grove, IL (US); Maxwell Moore, Rockford, IL (US); Tahirah K. Heath, Chicago, IL (US); Walter Fast, Austin, TX (US)

(73) Assignees: LOYOLA UNIVERSITY OF CHICAGO, Chicago, IL (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 19 days.

(21) Appl. No.: 15/742,947

(22) PCT Filed: Jul. 11, 2016

(86) PCT No.: PCT/US2016/041797
§ 371 (c)(1),
(2) Date: Jan. 9, 2018

(87) PCT Pub. No.: WO2017/011408
PCT Pub. Date: Jan. 19, 2017

(65) Prior Publication Data
US 2019/0084932 A1    Mar. 21, 2019

Related U.S. Application Data

(60) Provisional application No. 62/191,119, filed on Jul. 10, 2015.

(51) Int. Cl.
| | | |
|---|---|---|
| *A61K 45/06* | (2006.01) | |
| *C07D 209/08* | (2006.01) | |
| *A61P 31/04* | (2006.01) | |
| *C07D 249/04* | (2006.01) | |
| *C07D 401/12* | (2006.01) | |
| *C07D 403/12* | (2006.01) | |

(52) U.S. Cl.
CPC ............ *C07D 209/08* (2013.01); *A61K 45/06* (2013.01); *A61P 31/04* (2018.01); *C07D 249/04* (2013.01); *C07D 401/12* (2013.01); *C07D 403/12* (2013.01)

(58) Field of Classification Search
None
See application file for complete search history.

(56) References Cited

U.S. PATENT DOCUMENTS

| 3,083,207 | A | * | 3/1963 | Hoehn et al. | ........ C07D 209/08 548/490 |
| 3,117,131 | A | * | 1/1964 | Breuer | ................ C07D 209/08 548/490 |
| 2010/0152177 | A1 | | 6/2010 | Dunn et al. | |
| 2013/0109672 | A1 | | 5/2013 | Boxer et al. | |

OTHER PUBLICATIONS

Antibiotic resistance threats in the United States, Centers for Disease Control and Prevention, 2013.
Blotny et al., A new, mild preparation of sulfonyl chlorides, Tetrahedron Lett., 44(7):1499-501 (2003).
Christopeit et al., Discovery of a novel covalent non-ß-lactam inhibitor of the metallo-ß-lactamase NDM-1, Bioorg. Med. Chem., 24(13):2947-53 (2016).
Fischbach et al., Antibiotics for emerging pathogens, Science, 325(5944):1089-93 (2009).
Gillner et al., Inhibitors of bacterial N-succinyl-L,L-diaminopimelic acid desuccinylase (DapE) and demonstration of in vitro antimicrobial activity, Bioorg. Med. Chem. Lett., 19(22):6350-2 (2009).
Gilvarg, N-Succinyl-L-diaminopimelic acid, J. Biol. Chem., 234:2955-9 (1959).
Heath et al., Practical spectrophotometric assay for the dapE-encoded N-succinyl-L,L-diaminopimelic acid desuccinylase, a potential antibiotic target, PLoS One, 24 pp. (Apr. 26, 2018).
International Application No. PCT/US2016/041797, International Preliminary Report on Patentability, dated Jan. 16, 2018.
International Application No. PCT/US2016/041797, International Search Report and Written Opinion, dated Dec. 2, 2016.
Iwao et al., Synthesis of 7-substituted indolines via directed lithiation of 1-(tert-Butoxycarbonyl)indonline: 7-indolinecarboxaldehyde, Org. Synth., 73:85 (1996).
Kim et al., Structure of apo- and monometalated forms of NDM-1—a highly potent carbapenem-hydrolyzing metallo-ß-lactamase, PLoS One, 6(9):e24621 (2011).
Li et al., Simplified captopril analogues as NDM-1 inhibitors, Bioorg. Med. Chem. Lett., 24(1):386-9 (2014).
Phillips et al., 5'-alkyl-benzothiadiazides: a new subgroup of AMPA receptor modulators with improved affinity, Bioorg. Med. Chem., 10(5):1229-48 (2002).
PUBCHEM, Substance Record for SID 187575391, create date: Jul. 7, 2014 (retrieved on Aug. 15, 2016). Retrieved from the Internet at: <https://pubchem.ncbi.nlm.nih.gov/substance/187575391>.
Raushel et al., Efficient synthesis of 1-sulfonyl-1,2,3-triazoles, Org. Lett., 12(21):4952-5 (2010).
Rolain et al., New Delhi metallo-beta-lactamase (NDM-1): towards a new pandemia?, Clin. Microbiol. Infect., 16(12):1699-701 (2010).
Scapin et al., Enzymology of bacterial lysine biosynthesis, Adv. Enzymol. Relat. Areas Mol. Biol., 72:279-324 (1998).
Smith et al., A General and Efficient Method for the Preparation of Organic Sulfonic Acids by Insertion of Sulfur Trioxide into the Metal-Carbon Bond of Organolithiums, J. Org. Chem., 61(4):1530-2 (1996).

(Continued)

*Primary Examiner* — Samantha L Shterengarts
(74) *Attorney, Agent, or Firm* — Marshall, Gerstein & Borun LLP

(57) ABSTRACT

Indoline and tetrahydroquinoline sulfonyl compounds that can inhibit DapE and/or bacterial metallo-β-lactamases ("MBLs"), such as NDM-1 are disclosed. Also disclosed are methods of treating an individual suffering from a bacterial infection using the compounds disclosed herein.

19 Claims, 1 Drawing Sheet

(56) References Cited

OTHER PUBLICATIONS

Spellberg, Antibiotic resistance: promoting critically needed antibiotic research and development and appropriate use ("stewardship") of these previous drugs, Testimony of the Infectious Diseases Society of America Before the House Committee on Energy and Commerce Subcommittee on Health (Jun. 9, 2010).
Uda et al., Selectivity of Inhibition of N-Succinyl-L,L-Diaminopimelic Acid Desuccinylase in Bacteria: The product of dapE-gene is Not the Target of L-Captopril Antimicrobial Activity, Bioinorg. Chem. Appln., Article ID 306465, 6 pp. (2011).
Yang et al., Azolylthioacetamide: A Highly Promising Scaffold for the Development of Metallo-ß-lactamase Inhibitors, ACS Med. Chem. Lett., 6(4):455-60 (2015).
Yang et al., Spectroscopic and mechanistic studies of heterodimetallic forms of metallo-ß-lactamase NDM-1, J. Am. Chem. Soc., 136(20):7273-85 (2014).
Yoo et al., Mechanistic studies on the Cu-catalyzed three-component reactions of sulfonyl azides, 1-alkynes and amines, alcohols, or water: dichotomy via a common pathway, J. Org. Chem., 73(14):5520-8 (2008).
Zhang et al., Diaryl-substituted azolylthioacetamides: Inhibitor discovery of New Delhi metallo-ß-lactamase-1 (NDM-1), ChemMedChem., 9(11):2445-8 (2014).

\* cited by examiner

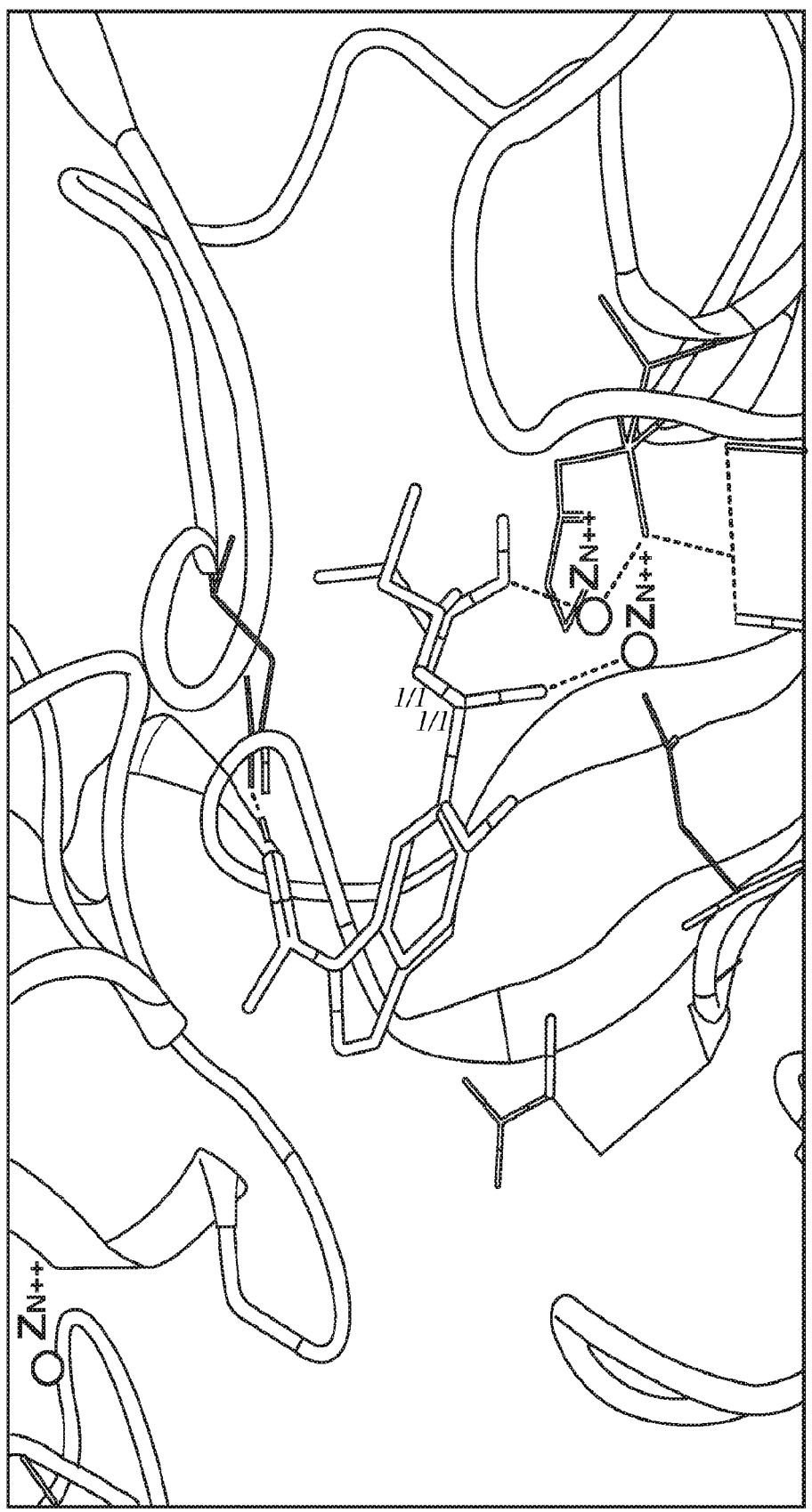

INDOLINE AND TETRAHYDROQUINOLINE SULFONYL INHIBITORS OF DIMETALLOENZYMES AND USE OF THE SAME

CROSS-REFERENCE TO RELATED APPLICATION

This application is filed pursuant to 35 U.S.C. § 371 as a U.S. National Phase Application of International Patent Application No. PCT/US16/041797, filed Jul. 11, 2016, claiming the benefit under 35 U.S.C. § 119(e) of U.S. Provisional Patent Application Ser. No. 62/191,119 filed Jul. 10, 2015, the disclosures of which are each incorporated herein by reference.

STATEMENT OF GOVERNMENT SUPPORT

This invention was made with government support under GM111926 awarded by the National Institutes of Health. The Government has certain rights in the invention.

FIELD

The present disclosure relates to indoline and tetrahydroquinoline sulfonyl compounds that inhibit dimetalloenzymes, such as the bacterial enzyme New Delhi metallo-β-lactamase ("NDM-1") and dapE-encoded N-succinyl-L,L-diaminopimelic acid desuccinylase ("DapE"). The present disclosure also relates to compositions containing the indoline and tetrahydroquinoline sulfonyl compounds described herein and to methods of treating bacterial infections by administering a therapeutically effective amount of a compound described herein, optionally with a second therapeutic, such as a β-lactam antibiotic.

BACKGROUND

The Centers for Disease Control and Prevention ("CDC") estimates that nearly two million infections annually involve resistant bacteria which result in at least 23,000 deaths every year, and notes the potentially catastrophic consequences of inaction. See *Antibiotic resistance threats in the United States,* 2013, U.S. Department of Health and Human Services, Centers for Disease Control and Prevention, pp. 1-113 (2013) at 6. Due to the increasing prevalence of drug resistance in bacterial strains, compromised in particular through overuse, antibiotic treatments are losing efficacy and potency in fighting infections, and, according to the Infectious Disease Society of America, at least ten new synthetic antibacterial drugs need to enter the market by the year 2020 in order to maintain the current quality of healthcare. See Spellberg, B. *Antibiotic Resistance: Promoting Critically Needed Antibiotic Research and Development and Appropriate Use ("Stewardship") of these Precious Drugs,* Testimony of the Infectious Diseases Society of America (IDSA), Before the House Committee on Energy and Commerce Subcommittee on Health, Jun. 9, 2010.

Multidrug-resistant *Mycobacterium tuberculosis*, methicillin-resistant and vancomycin-resistant *Staphylococcus aureus*, and $^{bla}$NDM-1/$^{bla}$KPC *Klebsiella pneumoniae* are significant global threats. See Fischbach, M. A.; Walsh, C. T. *Science*, 325:1089-1093 (2009). Therefore, it is urgent that new antibiotics, especially with new mechanisms of action, are discovered to meet the challenge of drug-resistant strains. See World Health Organization (2013) Global Tuberculosis Report, 308.

The bacterial enzyme, N-succinyl-L,L-diaminopimelic acid desuccinylase ("DapE") is a protein involved in the lysine and diaminopimelic acid ("Dap") biosynthetic pathway, and is critical for the synthesis of the bacterial cell wall. See Gillner, et al. Bioorg. Med. Chem. Lett., 2009, 19, 6350-635; Scapin, et al. Adv. Enzymol. Relat. Areas Mol. Biol., 1998, 72, 279-32; Gilvarg, et al. J. Biol. Chem., 1959, 234, 2955-2959. Small molecules that are able to block DapE activity are expected to be toxic to bacteria, allowing them to function effectively as antibiotics. Traditional DapE inhibitors, however, are suboptimal because they contain thiol moieties. The thiol moieties are prone to oxidation and also exhibit promiscuous selectivity because they often bind tightly to any zinc-containing enzyme. Also, at least one thiol-containing antimicrobial, captopril, was found to be independent of DapE inhibition. See Creus et al., *Bioinorg. Chem. Appl.,* 2011, 306465.

Metalloproteins account for nearly half the proteins in biology, but in contrast to the more ubiquitous mononuclear enzymes, di-nuclear metalloproteins constitute a large class of these proteins, yet we currently lack effective methods of inhibiting these enzymes for the development of new therapies.

β-Lactam antibiotics are the most commonly used antibacterial agents, and growing resistance to these drugs is a concern. Metallo-β-lactamases ("MBLs") are a diverse set of enzymes that catalyze the hydrolysis of a broad range of β-lactam drugs conferring resistance to the bacteria. New Delhi metallo-β-lactamase 1 ("NDM-1") is a zinc-dependent metallohydrolase found in bacteria that confers resistance to commonly-administered antibiotics, including penicillins, cephalosporins, and carbapenems. See Rolain, J. M.; Parola, P.; Cornaglia, G. *Clinical Microbiology and Infection* 2010, 16, 1699-1701; *PLoS One* 2011, 6, e24621; *J. Am. Chem. Soc.* 2014, 136, 7273-7285. Horizontal gene transfer has enabled the bla$_{NDM-1}$ gene to spread between species, facilitating the development of multi-drug resistant bacterial strains. Id. Bacteria carrying the bla$_{NDM-1}$ gene have been found on all continents, and consequently, NDM-1 has gained international attention as a clinically relevant pharmaceutical target. Id. Known inhibitors of MBLs, such as thiol-containing inhibitors, are prone to oxidation and challenges with selectivity due to the thiol moiety. See Li et al., Bioorganic & Medicinal Chemistry 24:386-389 (2014). As such, drug development efforts of NDM-1 have proven ineffective due to a lack of effective inhibitors. See Rolain et al., *Clinical Microbiology and Infection,* 16:1699-1701 (2010).

Therefore, new compounds capable of inhibiting DapE and MBLs, such as NDM-1 are greatly needed. See, e.g, Christopeit et al., *Bioorganic & Medicinal Chemistry* 24:2947-2943 (2016); Zhang et al., *ChemMedChem Communications* 9:2445-2448 (2014), Feng et al., *Bioorganic & Medicinal Chemistry* 22:5185-5189 (2012), Yang et al., *ACS Medicinal Chemistry Letters* 6:455-460 (2015).

SUMMARY

One aspect of the disclosure provides a compound having a structure of Formula (I), or a pharmaceutically acceptable salt thereof:

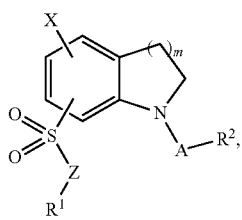

(I)

wherein m is 1 or 2;

A is C=O or SO$_2$;

X is H, C$_{1-6}$alkyl, halo, OH, C$_{1-6}$alkoxy, aryl, or heteroaryl having 1, 2, 3, or 4 heteroatoms selected from N, O, and S;

Z is

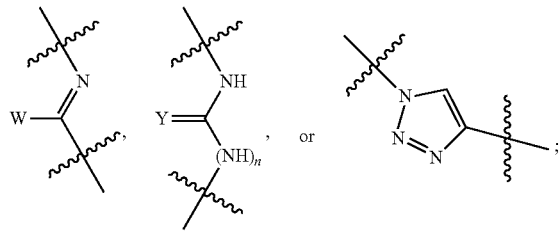

n is 0 or 1;

W is NR$^3$R$^4$ or OR$^7$;

Y is O, S, or NR$^6$;

R$^1$ is C$_{1-6}$alkyl, C$_{2-6}$alkenyl, C$_{1-4}$alkylene-OH, C$_{1-4}$alkylene-CN, C$_{1-4}$alkylene-halo, C$_{1-4}$alkylene-NR$^6$$_2$, C$_{0-4}$alkylene-R$^5$, C$_{1-4}$alkylene-C(=O)R$^5$, C$_{1-4}$alkylene-C(=O)OR$^5$, C$_{1-4}$alkylene-NHC(O)R$^5$, C$_{1-4}$alkylene-NHC(O)OR$_5$, C$_{1-4}$alkylene-C(=NOR$^6$)R$^5$, or C$_{1-4}$alkylene-OSO$_2$R$^5$;

R$^2$ is C$_{1-6}$alkyl, C$_{2-6}$alkenyl, C$_{1-4}$alkylene-CN, C$_{1-4}$alkylene-halo, C$_{0-4}$alkylene-R$^5$, C$_{0-4}$alkylene-OR$^5$, or C$_{1-4}$alkylene-SO$_2$R$^5$;

R$^3$ and R$^4$ are each independently H, C$_{1-4}$alkyl, C$_{0-4}$alkylene-C(O)C$_{1-4}$alkyl, C$_{0-4}$alkylene-CO$_2$R$^6$, C$_{0-4}$alkylene-NR$^6$$_2$, C$_{0-4}$alkylene-C$_{3-6}$cycloalkyl, C$_{0-4}$alkylene-C$_{3-6}$heterocycloalkyl having 1, 2, or 3 heteroatoms selected from N, O and S, or C$_{0-4}$alkylene-C$_{6-10}$aryl, or R$^3$ and R$^4$ are taken together with the nitrogen to which they are attached to form a 5-7 membered ring;

R$^5$ is H, C$_{1-6}$alkyl, C$_{2-6}$alkenyl, C$_{0-4}$alkylene-C$_{3-6}$cycloalkyl, C$_{0-4}$alkylene-C$_{3-6}$heterocycloalkyl having 1, 2, or 3 heteroatoms selected from N, O and S, C$_{0-4}$alkylene-C$_{6-10}$aryl, C$_{2-4}$alkenylene-C$_{6-10}$aryl, C$_{0-4}$alkylene-C$_{5-10}$heteroaryl having 1, 2, 3, or 4 heteroatoms selected from N, O, and S, or NR$^3$R$^4$;

each R$^6$ independently is H or C$_{1-3}$alkyl; and

R$^7$ is H, C$_{1-6}$alkyl, C$_{0-4}$alkylene-C$_{6-10}$aryl, or C$_{0-4}$alkylene-C(O)—C$_{1-4}$alkylene-NR$^6$$_2$.

In some embodiments, the includes a structure of Formula (I'):

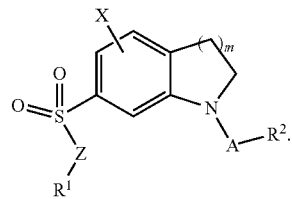

(I')

In some cases, m is 1. In various cases, m is 2.

In some embodiments, A is C=O. In various embodiments, A is SO$_2$.

In some cases, Z is

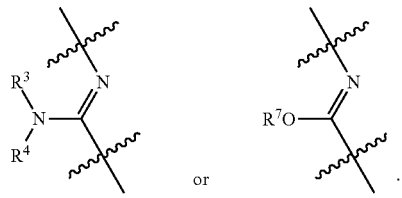

For example, the compound of Formula (I) can include a structure:

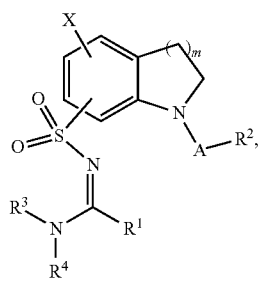

(IA)

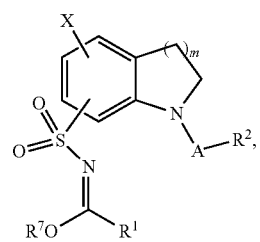

(IB)

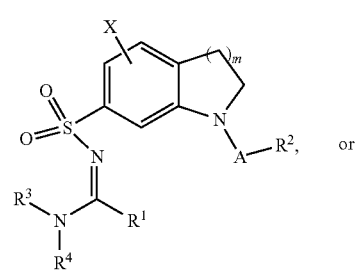

(IA')

(IB')

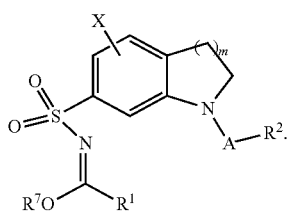

In some embodiments, $R^3$ and $R^4$ are each independently selected from the group consisting of H, $C_{1-4}$alkyl, and $C_{0-4}$alkylene-C(O)$C_{1-4}$alkyl, $C_{0-4}$alkylene-CO$_2$R$^6$, $C_{0-4}$alkylene-NR$^6{}_2$, or $R^3$ and $R^4$ are taken together with the nitrogen to which they are attached to form a 5-7 membered ring; and $R^7$ is H, $C_{1-3}$alkyl, $C_{0-4}$alkylene-$C_{6-10}$aryl, or C(O)—$C_{1-2}$alkylene-NR$^6{}_2$. In various embodiments, $R^3$ and $R^4$ are each independently selected from the group consisting of H,

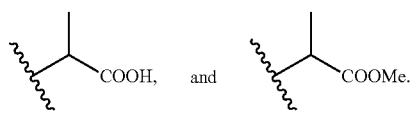

For example, each of $R^3$, $R^4$, and $R^7$ can be H.

In some embodiments, wherein Z is

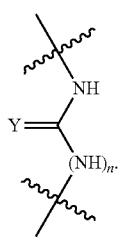

In various of these embodiments, Y is O. In some of these embodiments, Y is S. In some of these embodiments, Y is NR$^6$ (e.g., NH). In some cases, n is 0. In various cases, n is 1. In some embodiments, the compound of Formula (I) has a structure:

(IC)

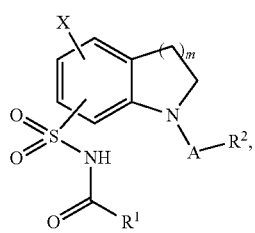

(ID)

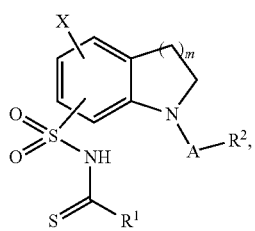

(IE)

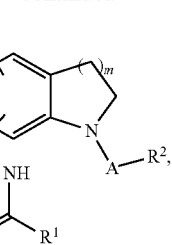

(IF)

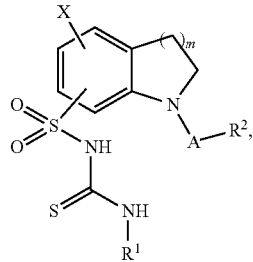

(IC')

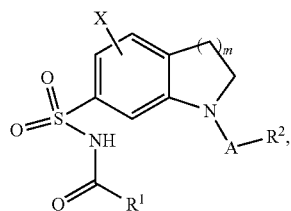

(ID')

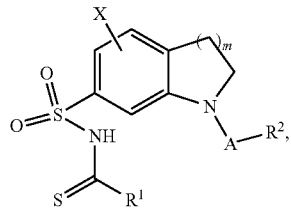

(IE')

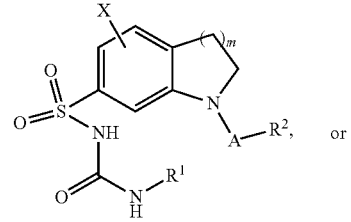

or (IF')

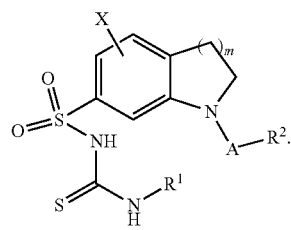

In some cases, wherein Z is

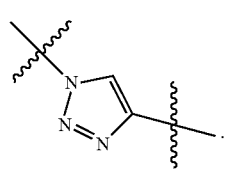 [SMILES: *c1cn(*)nn1]

In some of these embodiments, the compound of Formula (I) includes a structure:

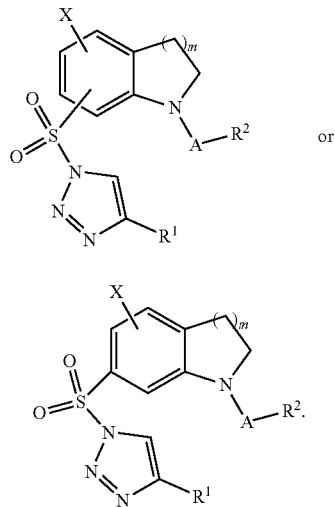

For example, the compound of Formula (I) can have a structure:

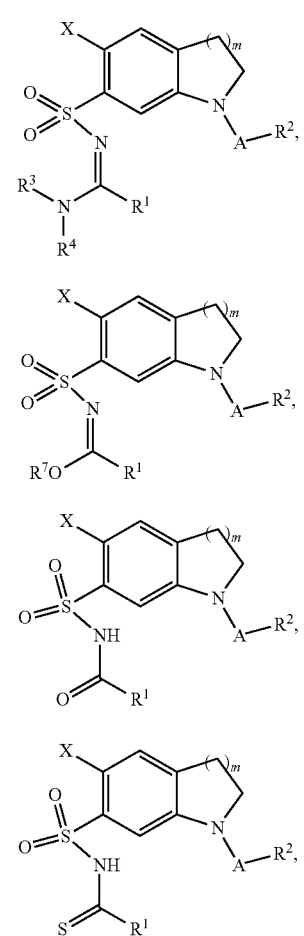

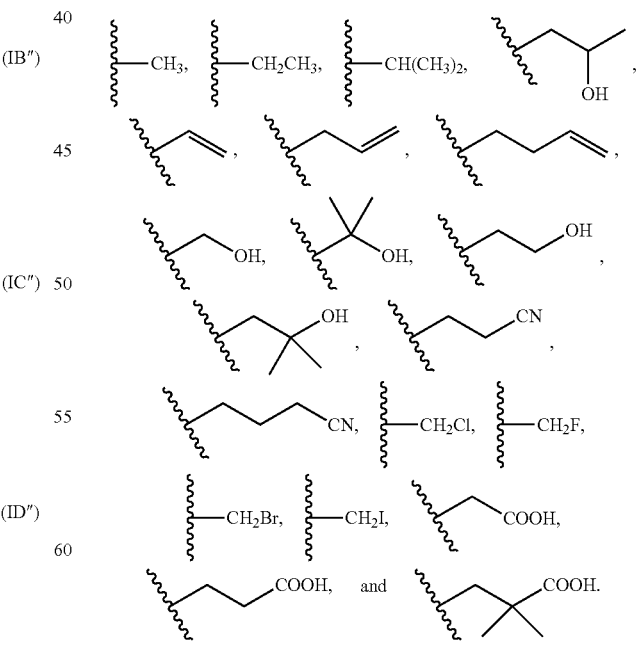

In some cases, X is H, F, Cl, Br, I, CH₃, CF₃, OCH₃, or OCF₃. For example, X can be H, F, Cl, or Br.

In some embodiments, $R^1$ is $C_{1-6}$alkyl, $C_{2-6}$alkenyl, $C_{1-4}$alkylene-OH, $C_{1-4}$alkylene-CN, $C_{1-4}$alkylene-halo, or $C_{1-4}$alkylene-CO$_2$H. For example, $R^1$ can be selected from the group consisting of:

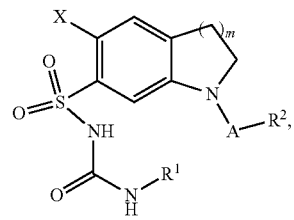

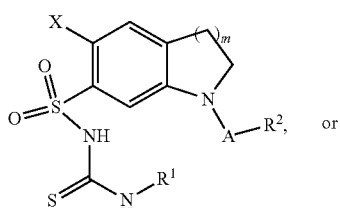

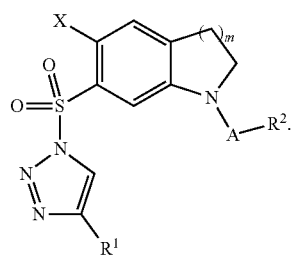

In various embodiments, $R^1$ is $C_{0-4}$alkylene-$C_{3-6}$cycloalkyl or $C_{0-4}$alkylene-heterocycloalkyl having 1, 2, or 3 heteroatoms selected from N, O and S. For example, $R^1$ can be selected from the group consisting of:

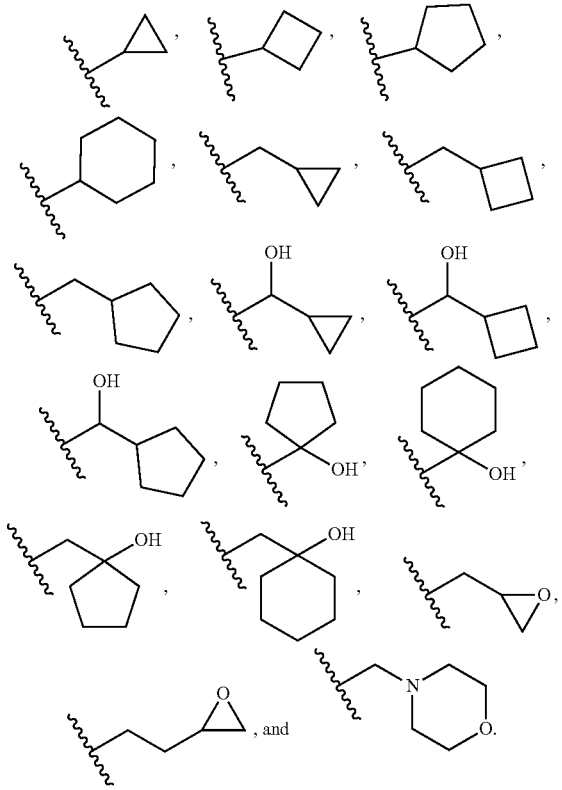

In some cases, $R^1$ is $C_{0-4}$alkylene-$C_{6-10}$aryl. For example, $R^1$ can be selected from the group consisting of:

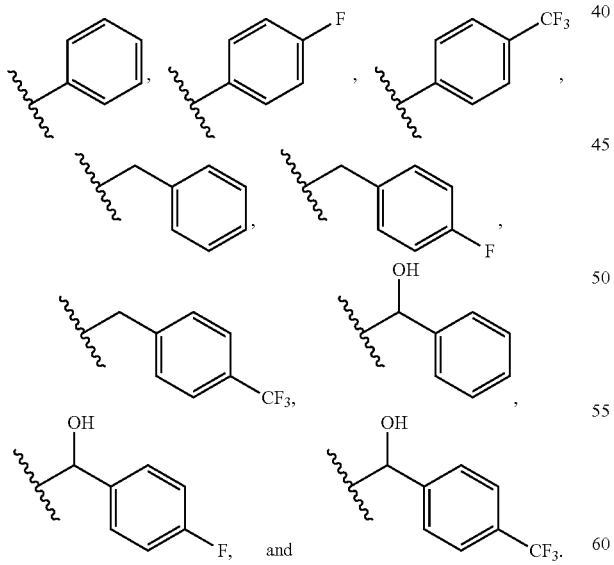

In various cases, $R^1$ is $C_{0-4}$alkylene-$C_{5-10}$heteroaryl having 1, 2, 3, or 4 heteroatoms selected from N, O, and S, or $R^1$ is $C_{0-1}$alkylene-$C_{5-6}$heteroaryl having 1 or 2 heteroatoms. For example, $R^1$ can be selected from the group consisting of:

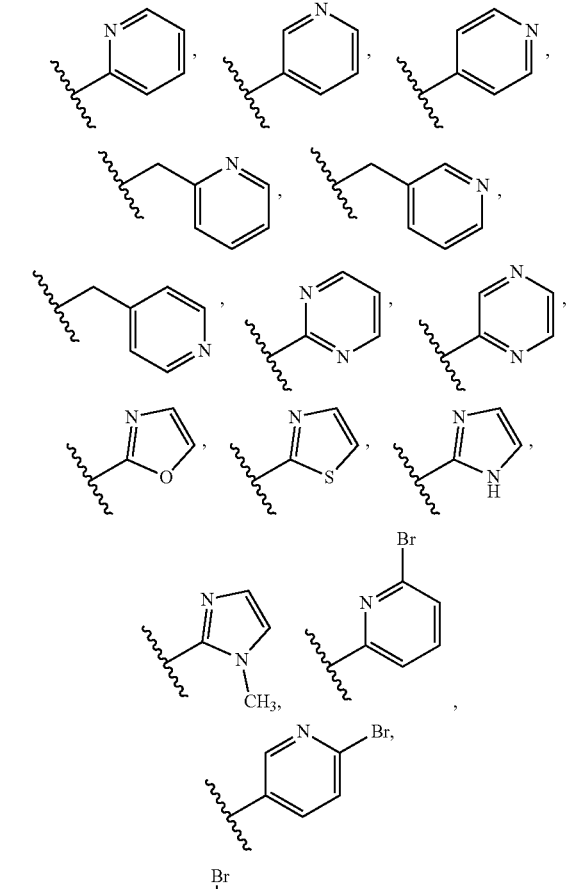

In some embodiments, $R^1$ is $C_{0-4}$alkylene-$NR^6_2$, $C_{1-4}$alkyleneC(=O)$R^5$, $C_{1-4}$alkyleneC(=O)O$R^5$, $C_{1-4}$alkylene-NHC(O)$R^5$, $C_{1-4}$alkylene-NHC(O)O$R_5$, or $C_{1-4}$alkylene-C(=NO$R^6$)$R^5$, and $R^5$ is $C_{1-3}$alkyl, $C_{0-1}$alkylene-phenyl, or $NR^3R^4$. For example, $R^1$ can be selected from the group consisting of:

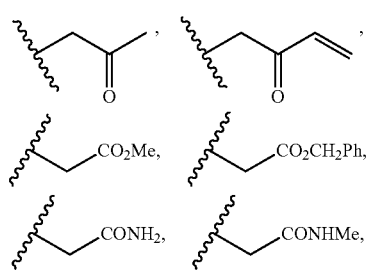

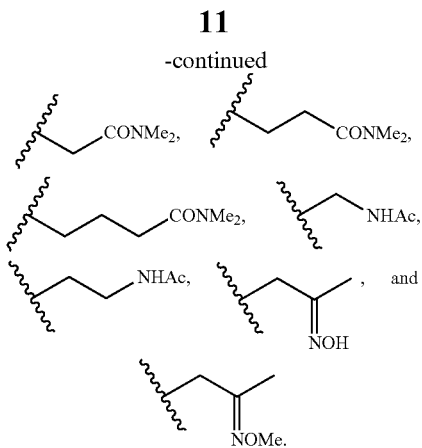

In various embodiments, $R^1$ is $C_{1-4}$alkylene-$OSO_2R^5$, and $R^5$ is $C_{1-3}$alkyl or phenyl. For example, $R^1$ can be selected from the group consisting of $CH_2OSO_2CH_3$, $CH_2OSO_2CF_3$, $CH_2OSO_2Ph$, and $CH_2OSO_2PhCH_3$.

In some embodiments, $R^2$ is $C_{1-6}$alkyl, $C_{2-6}$alkenyl, $C_{1-4}$alkylene-OH, $C_{1-4}$alkylene-CN, or $C_{1-4}$alkylene-halo. For example, $R^2$ can be selected from the group consisting of:

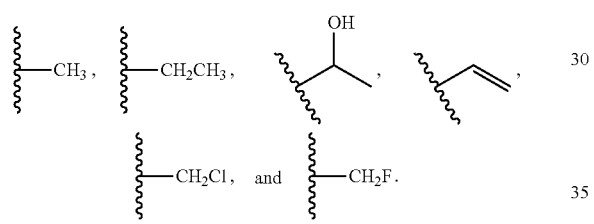

In various cases, $R^2$ is $C_{0-4}$alkylene-$C_{3-6}$cycloalkyl or $C_{0-4}$alkylene-$C_{3-6}$heterocycloalkyl having 1, 2, or 3 heteroatoms selected from N, O and S. For example, $R^2$ can be selected from the group consisting of:

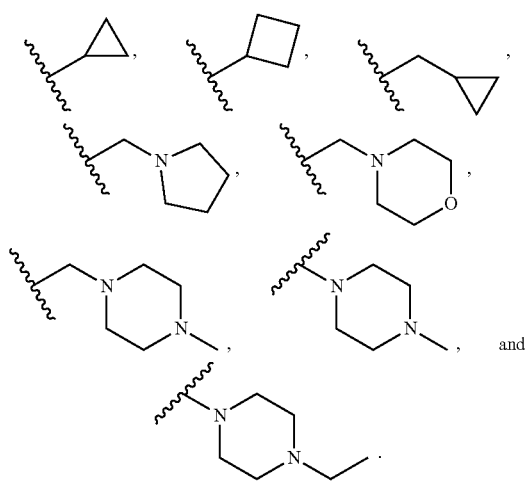

In some embodiments, $R^2$ is $C_{0-4}$alkylene-$C_{6-10}$aryl or $C_{0-4}$alkylene-$C_{5-10}$heteroaryl having 1, 2, 3, or 4 heteroatoms selected from N, O, and S. For example, $R^2$ can be selected from the group consisting of:

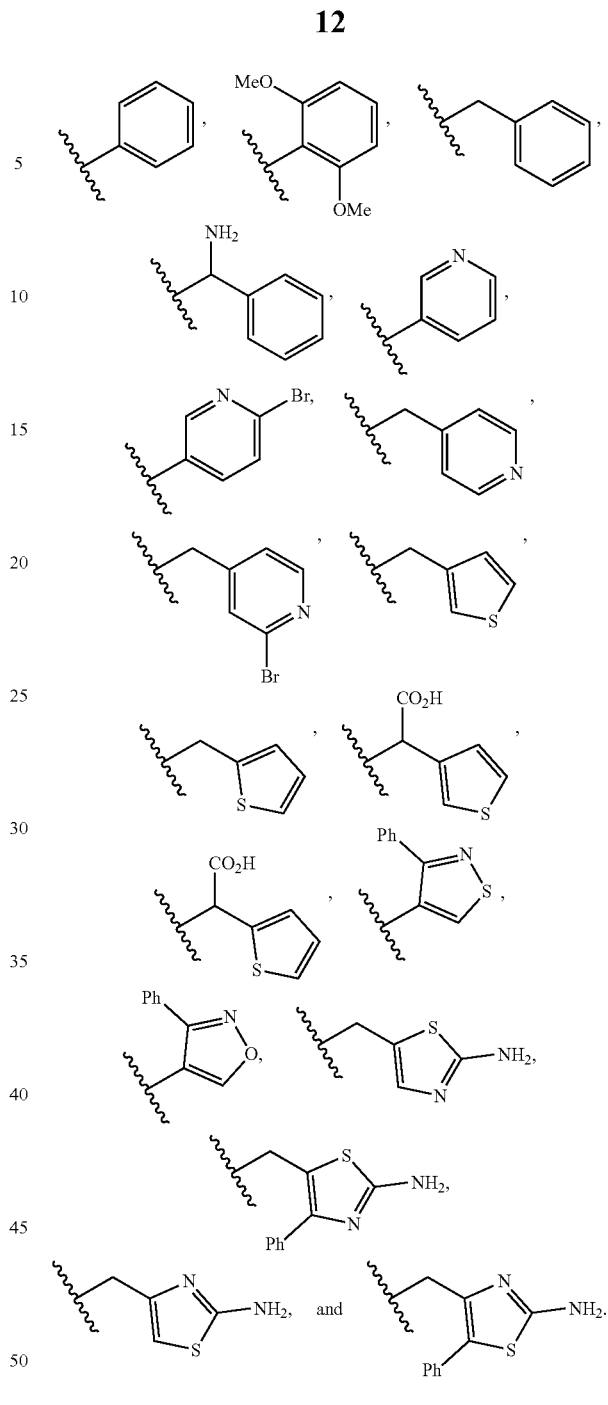

In some cases, $R^2$ is $C_{0-4}$alkylene-$NR^3R^4$. For example, $R^2$ can be selected from the group consisting of:

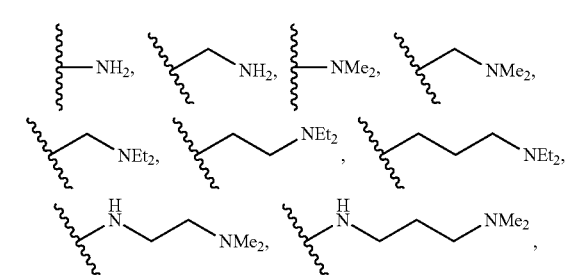

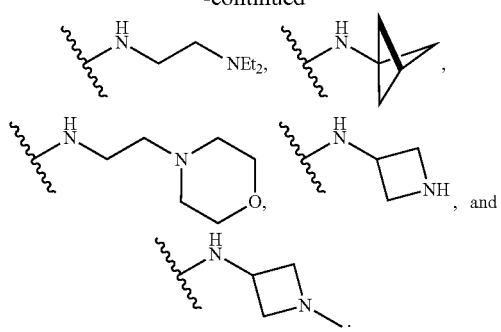
In various cases, $R^2$ is $C_{0-4}$alkylene-$OR^5$ or $C_{1-4}$alkylene-$SO_2R^5$. For example, $R^2$ can be selected from the group consisting of:
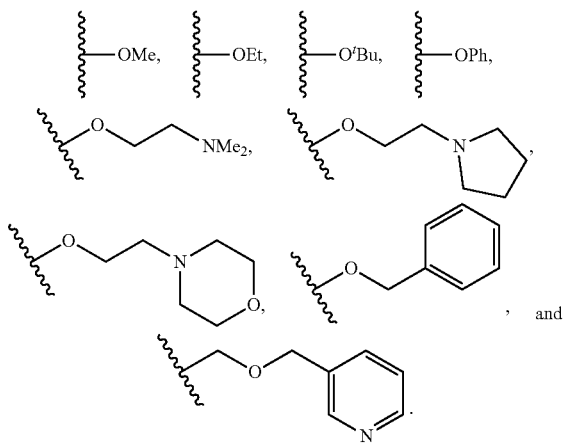
In some embodiments, the compound of Formula (I) has a structure selected from the group consisting of:
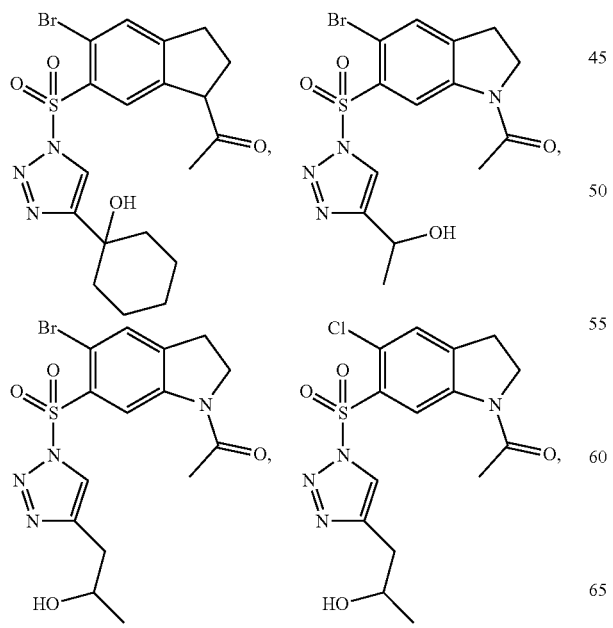
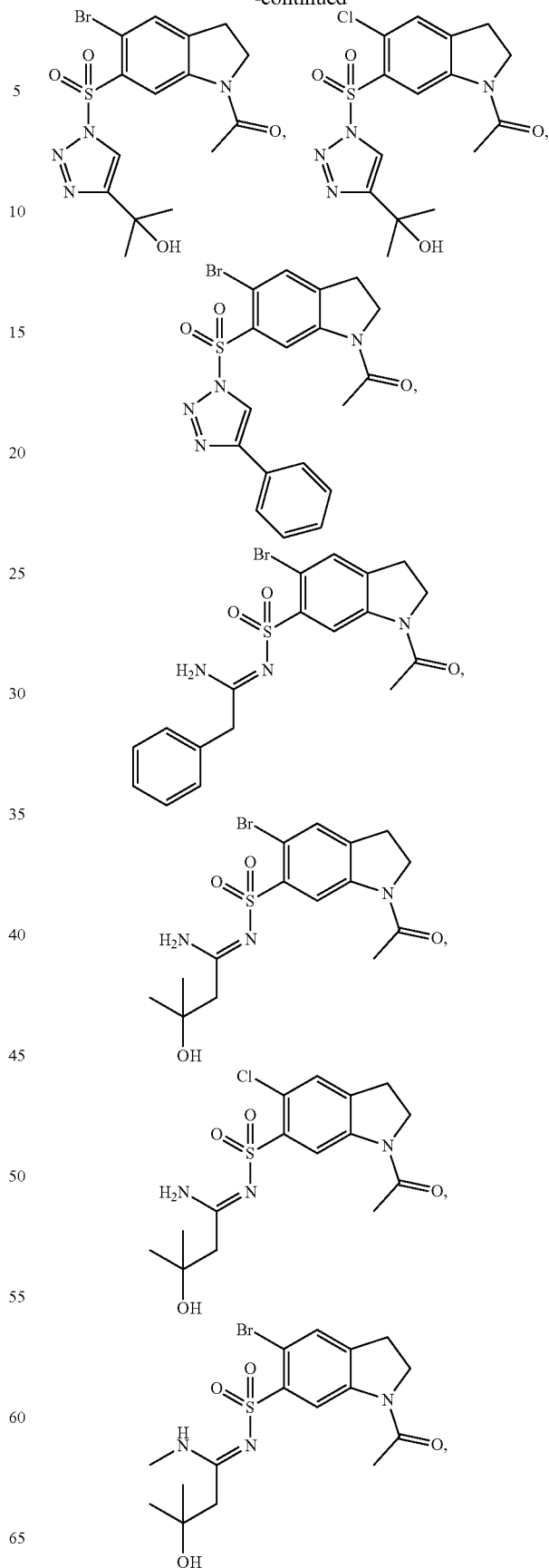

15
-continued
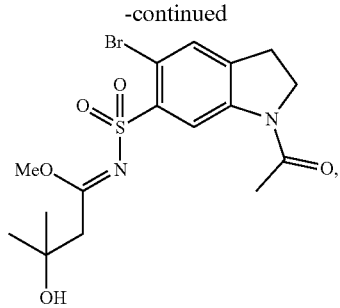
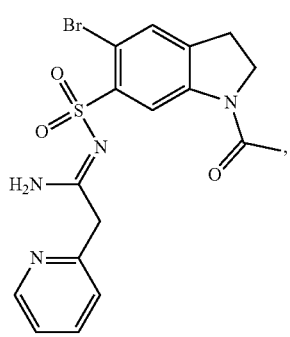
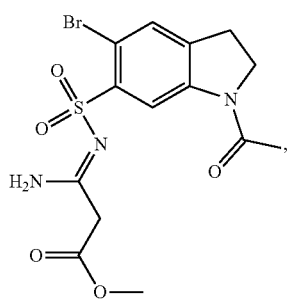
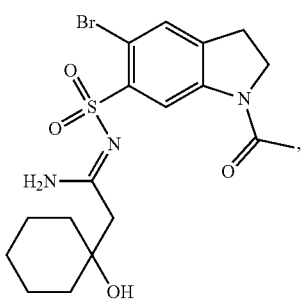
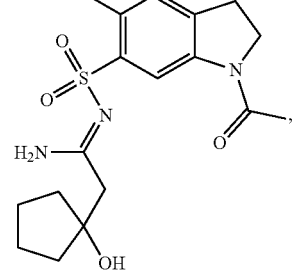
16
-continued
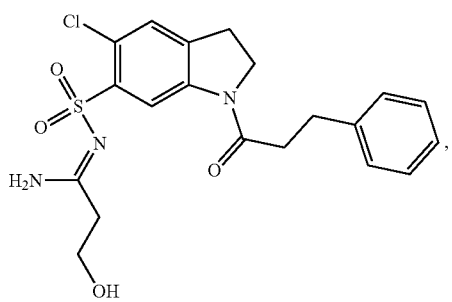
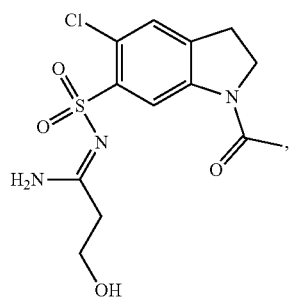
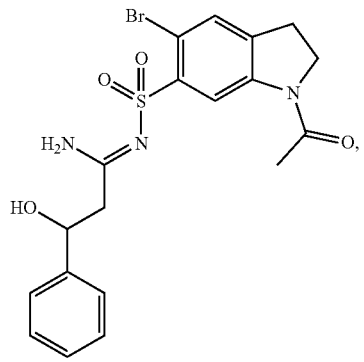
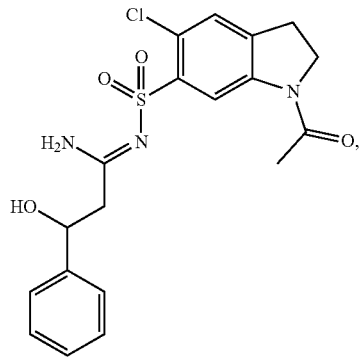

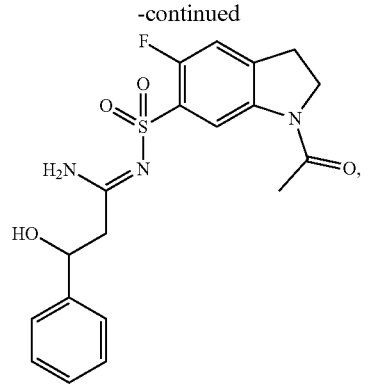
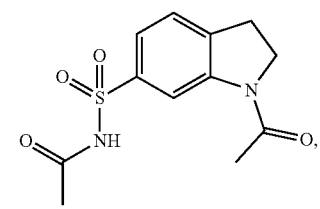
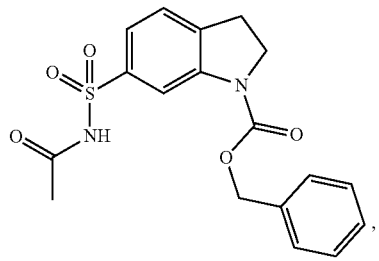
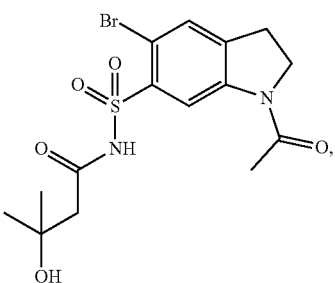
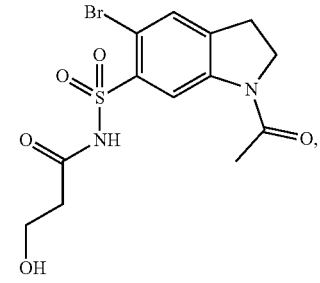
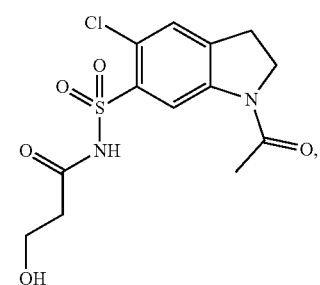
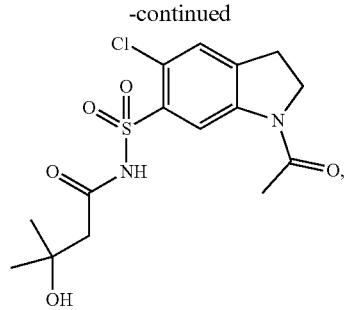
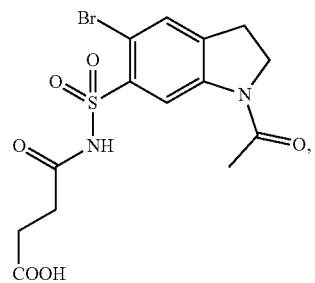
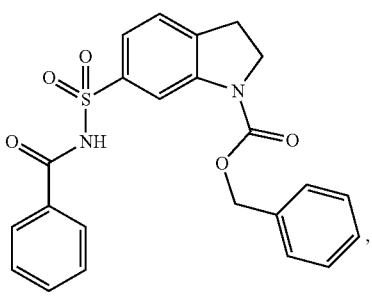
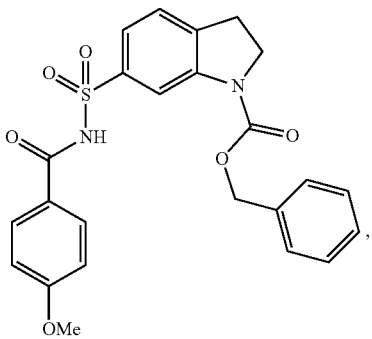
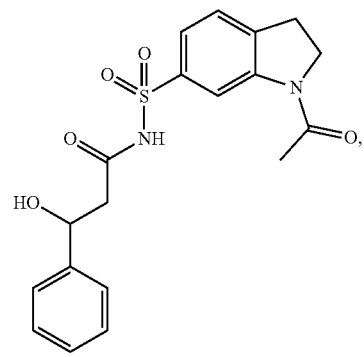

-continued

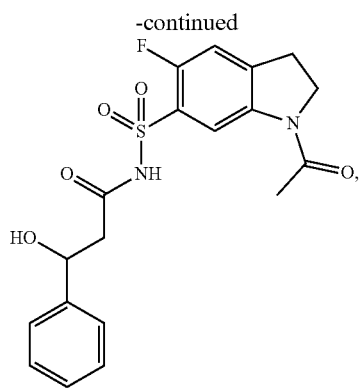

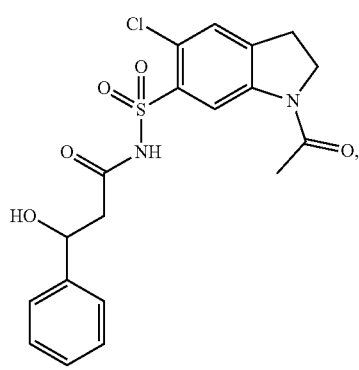

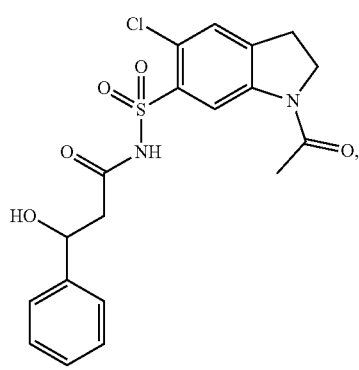

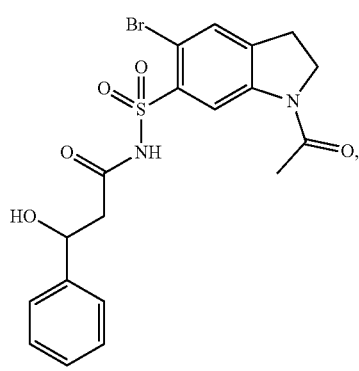

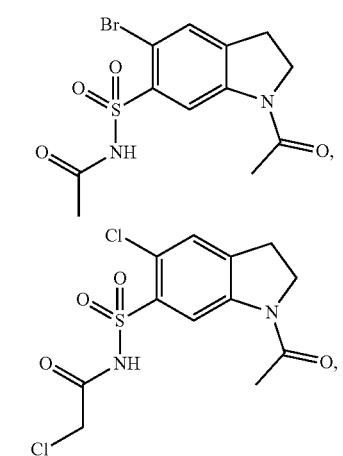

-continued

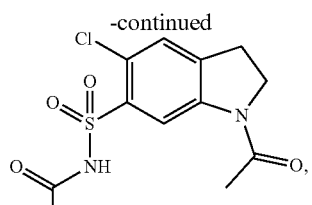

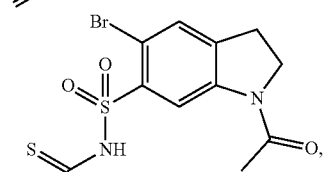

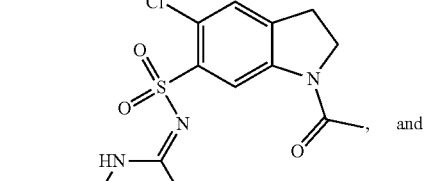

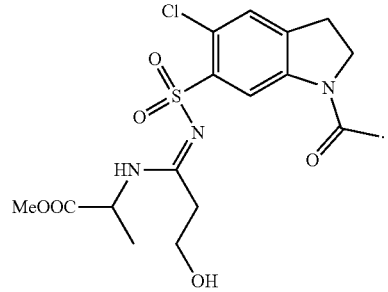

Another aspect of the disclosure provides a pharmaceutical composition comprising a compound described herein and a pharmaceutically acceptable carrier or vehicle.

Yet another aspect of the disclosure provides a method of inhibiting a bacterial metallo-β-lactamase (MBL) in a cell comprising contacting the cell with a compound described herein or a pharmaceutical composition described herein. In some embodiments, the MBL is selected from the group consisting of NDM-1, IMP-1, and VIM-2. For example, the MBL can be NDM-1.

Another aspect of the disclosure provides a method of inhibiting DapE in a cell comprising contacting the cell with a compound described herein or a pharmaceutical composition described herein. In some embodiments, the contacting occurs in vivo. In various embodiments, the contacting comprises administering to a subject in need thereof. In some cases, the subject suffers from bacterial infection.

Yet another aspect of the disclosure provides a method of treating a disease or condition wherein inhibition of a MBL of DapE provides a benefit comprising administering to an individual in need thereof a therapeutically effective amount of a compound described herein or a pharmaceutical composition described herein. In some embodiments, the MBL is selected from the group consisting of NDM-1, IMP-1, and VIM-2. For example, the MBL can be NDM-1. In some cases, the disease or condition is a bacterial infection. In some cases, the method further includes administering a therapeutically effective amount of a second therapeutic agent useful in the treatment of the disease or condition. In various cases, the compound and the second therapeutic agent are administered simultaneously. In some embodiments, the compound and the second therapeutic agent are administered separately. In various embodiments, the second therapeutic agent is a β-lactam antibiotic.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the disclosure to the specific embodiments described herein.

BRIEF DESCRIPTION OF THE DRAWINGS

FIG. 1 depicts molecular docking studies, demonstrating that the indoline and tetrahydroquinoline sulfonyl compounds described herein are capable of bridging two active zinc atoms of MBLs.

DETAILED DESCRIPTION

Disclosed herein are indoline and tetrahydroquinoline compounds having a sulfonyl amidine moiety, an acyl sulfonamide moiety, or a sulfonyl triazole moiety. The indoline and tetrahydroquinoline sulfonyl compounds described herein can inhibit DapE, bacterial metallo-β-lactamases ("MBL") such as New Delhi metallo-β-lactamase 1 ("NDM-1"), or both, and are useful against a wide variety of microorganisms. The present indoline and tetrahydroquinoline sulfonyl compounds are advantageous over traditional inhibitors of DapE and NDM-1 because they do not rely on a thiol (SH) group for their inhibitory activity. Therefore, they avoid the instability and lack of selectivity of traditional thiol-containing inhibitors of DapE and MBLs, which tend to tightly bind to any zinc-containing enzyme.

The compounds disclosed herein can act as inhibitors of DapE. For example, the compounds disclosed herein can have $IC_{50}$ values in a range of about 1 nM to about 1000 µM. In various cases, the compounds described herein inhibit DapE with an $IC_{50}$ up to about 100 µM. In some embodiments, the compounds disclosed herein have an $IC_{50}$ value for DapE of less than about 100 µM, or less than about 75 µM, or less than about 50 µM, or less than about 25 µM, or less than about 10 µM, or less than about 5 µM, or less than about 1 µM, or less than about 0.5 µM, or less than about 0.1 µM, or less than about 0.05 µM, or less than about 0.01 µM. In some embodiments, the compounds disclosed herein can have $IC_{50}$ values in a range of about 1 nM to about 200 µM, or about 0.05 µM to about 150 µM, or about 1 µM to about 100 µM, or about 0.5 µM to about 150 µM, or about 0.5 µM to about 125 µM, or about 0.5 µM to about 100 µM, or about 0.5 µM to about 75 µM, or about 0.5 µM to about 50 µM, or about 0.5 µM to about 25 µM, or about 0.5 µM to about 15 µM, or about 0.5 µM to about 10 µM, or about 0.5 µM to about 5 µM.

The compounds disclosed herein can act as inhibitors of MBL, such as NDM-1. For example, the compounds disclosed herein can have $IC_{50}$ values in a range of about 1 nM to about 1000 µM. In various cases, the compounds described herein inhibit NDM-1 with an $IC_{50}$ up to about 100 µM. In some embodiments, the compounds disclosed herein have an $IC_{50}$ value for NDM-1 of less than about 100 µM, or less than about 75 µM, or less than about 50 µM, or less than about 25 µM, or less than about 10 µM, or less than about 5 µM, or less than about 1 µM, or less than about 0.5 µM, or less than about 0.1 µM, or less than about 0.05 µM, or less than about 0.01 µM. In some embodiments, the compounds disclosed herein can have $IC_{50}$ values in a range of about 1 nM to about 200 µM, or about 0.05 µM to about 150 µM, or about 1 µM to about 100 µM, or about 0.5 µM to about 150 µM, or about 0.5 µM to about 125 µM, or about 0.5 µM to about 100 µM, or about 0.5 µM to about 75 µM, or about 0.5 µM to about 50 µM, or about 0.5 µM to about 25 µM, or about 0.5 µM to about 15 µM, or about 0.5 µM to about 10 µM, or about 0.5 µM to about 5 µM.

Definitions

The term "a disease or condition wherein inhibition of DapE provides a benefit" pertains to a condition in which DapE, and/or an action of DapE, is important or necessary, e.g., for the onset, progress, expression of that disease or condition, or a disease or a condition which is known to be treated by DapE inhibitor. An example of such a condition includes, but is not limited to, a bacterial infection. One of ordinary skill in the art is readily able to determine whether a compound treats a disease or condition mediated by DapE for any particular cell type, for example, by assays which conveniently can be used to assess the activity of particular compounds.

The term "a disease or condition wherein inhibition of a MBL provides a benefit" pertains to a condition in which a MBL, and/or an action of MBL, such as NDM-1, is important or necessary, e.g., for the onset, progress, expression of that disease or condition, or a disease or a condition which is known to be treated by a MBL inhibitor. An example of such a condition includes, but is not limited to, a bacterial infection and rescuing the efficacy of a β-lactam antibiotic when treating a resistant bacterial infection. One of ordinary skill in the art is readily able to determine whether a compound treats a disease or condition mediated by MBL for any particular cell type, for example, by assays which conveniently can be used to assess the activity of particular compounds.

The term "second therapeutic agent" refers to a therapeutic agent different from a DapE and/or MBL inhibitor of structural Formulae I, I', IA, IA', IA", IB, IB', IB", IC, IC', IC", ID, ID', ID", IE, IE', IE", IF, IF', IF", IG, IG', or IG" and that is known to treat the disease or condition of interest. For example when a bacterial infection is the disease or condition of interest, the second therapeutic agent can be a known antibiotic, such as a β-lactam antibiotic.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

As used herein, the term "therapeutically effective amount" means an amount of a compound or combination of therapeutically active compounds (e.g., a DapE and/or NDM-1 inhibitor) that ameliorates, attenuates or eliminates one or more symptoms of a particular disease or condition (e.g., bacterial infection), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable carrier" refers to a medium that does not interfere with the effectiveness of the biological activity of the active ingredient(s) and is not toxic to the host to which it is administered.

As used herein, the term "excipient" means any pharmaceutically acceptable additive, carrier, diluent, adjuvant, or other ingredient, other than the active pharmaceutical ingredient (API).

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to a bivalent saturated aliphatic radical. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "heterocycloalkyl" is defined similarly as cycloalkyl, except the ring contains one to three heteroatoms independently selected from oxygen, nitrogen, or sulfur. Nonlimiting examples of heterocycloalkyl groups include piperdine, piperazine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, and alkyleneheteroaryl.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_{2-7}$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group As used herein, the term "cycloalkenyl" is defined similarly to "cycloalkyl" except for containing at least one carbon-carbon double bond. The term $C_n$ means the cycloalkenyl group has "n" carbon atoms. For example, $C_5$ cycloalkenyl refers to a cycloalkenyl group that has 5 carbon atoms in the ring. $C_{5-8}$ cycloalkenyl refers to cycloalkenyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkenyl groups include cyclopropenyl, cyclobutenyl, cyclopentenyl, cyclohexenyl, cycloheptenyl, and cyclooctenyl. Unless otherwise indicated, a cycloalkenyl group can be an unsubstituted cycloalkenyl group or a substituted cycloalkenyl group.

As used herein, the term "alkynyl" is defined identically as "alkyl" except for containing at least one carbon-carbon triple bond, and having two to thirty carbon atoms, for example, two to twenty carbon atoms, or two to ten carbon atoms. The term $C_n$ means the alkynyl group has "n" carbon atoms. For example, $C_4$ alkynyl refers to an alkynyl group that has 4 carbon atoms. $C_{2-7}$ alkynyl refers to an alkynyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkynyl groups include ethynyl, 1-propynyl, 2-propynyl, and butynyl. Unless otherwise indicated, an alkynyl group can be an unsubstituted alkynyl group or a substituted alkynyl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include, but are not limited to, pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group.

The term "thiol" or "sulfhydryl" as used herein refers to a "—SH" group.

As used herein, the term "halo" is defined as fluoro, chloro, bromo, and iodo.

The term "hydroxy" or "hydroxyl" is defined as —OH.

The term "alkoxy" or "alkoxyl" is defined as —OR, wherein R is alkyl.

The term "ether" as used herein refers to an alkyl group that includes at least one oxygen atom inserted within the alkyl group.

As used herein, the term "carboxy" or "carboxyl" as used herein refers to a "—COOH" group.

The term "cyano" as used herein refers to a —C≡N group, also designated —CN.

The term "nitro" refers to a —NO$_2$ group.

The term "amino" as used herein refers to a —NH$_2$ or —NH— group, wherein each hydrogen in each Formula can be replaced with an alkyl, cycloalkyl, aryl, heteroaryl, or heterocycloalkyl group.

A "substituted" functional group (e.g., a substituted alkyl, alkyleneyl, cycloalkyl, aryl, or heteroaryl refers to an alkyl, alkyleneyl, cycloalkyl, aryl, or heteroaryl) is a functional, group having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, sulfhydryl, and halo. When a substituted alkyl group includes more than one non-hydrogen radical, the substituents can be bound to the same carbon or two or more different carbon atoms.

Indoline and Tetrahydroquinoline Sulfonyl Compounds

In one aspect, the indoline and tetrahydroquinoline sulfonyl compounds of the disclosure have a structure of Formula (I), or a pharmaceutically acceptable salt thereof:

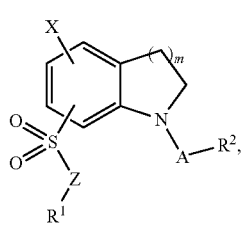

(I)

wherein m is 1 or 2;

A is C=O or SO$_2$;

X is H, C$_{1-6}$alkyl, halo, OH, C$_{1-6}$alkoxy, aryl, or heteroaryl having 1, 2, 3, or 4 heteroatoms selected from N, O, and S;

Z is

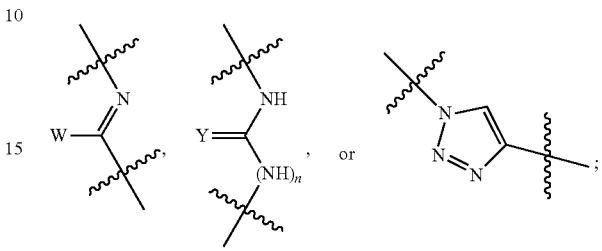

n is 0 or 1;

W is NR$^3$R$^4$ or OR$^7$;

Y is O, S, or NR$^6$;

R$^1$ is C$_{1-6}$alkyl, C$_{2-6}$alkenyl, C$_{1-4}$alkylene-OH, C$_{1-4}$alkylene-CN, C$_{1-4}$alkylene-halo, C$_{1-4}$alkylene-NR$^6{}_2$, C$_{0-4}$alkylene-R$^5$, C$_{1-4}$alkylene-C(=O)R$^5$, C$_{1-4}$alkylene-C(=O)OR$^5$, C$_{1-4}$alkylene-NHC(O)R$^5$, C$_{1-4}$alkylene-NHC(O)OR$_5$, C$_{1-4}$alkylene-C(=NOR$^6$)R$^5$, or C$_{1-4}$alkylene-OSO$_2$R$^5$;

R$^2$ is C$_{1-6}$alkyl, C$_{2-6}$alkenyl, C$_{1-4}$alkylene-CN, C$_{1-4}$alkylene-halo, C$_{0-4}$alkylene-R$^5$, C$_{0-4}$alkylene-OR$^5$, or C$_{1-4}$alkylene-SO$_2$R$^5$;

R$^3$ and R$^4$ are each independently H, C$_{1-4}$alkyl, C$_{0-4}$alkylene-C(O)C$_{1-4}$alkyl, C$_{0-4}$alkylene-CO$_2$R$^6$, C$_{0-4}$alkylene-NR$^6{}_2$, C$_{0-4}$alkylene-C$_{3-6}$cycloalkyl, C$_{0-4}$alkylene-C$_{3-6}$heterocycloalkyl having 1, 2, or 3 heteroatoms selected from N, O and S, or C$_{0-4}$alkylene-C$_{6-10}$aryl, or R$^3$ and R$^4$ are taken together with the nitrogen to which they are attached to form a 5-7 membered ring;

R$^5$ is H, C$_{1-6}$alkyl, C$_{2-6}$alkenyl, C$_{0-4}$alkylene-C$_{3-6}$cycloalkyl, C$_{0-4}$alkylene-C$_{3-6}$heterocycloalkyl having 1, 2, or 3 heteroatoms selected from N, O and S, C$_{0-4}$alkylene-C$_{6-10}$aryl, C$_{2-4}$alkenylene-C$_{6-10}$aryl, C$_{0-4}$alkylene-C$_{5-10}$heteroaryl having 1, 2, 3, or 4 heteroatoms selected from N, O, and S, or NR$^3$R$^4$;

each R$^6$ independently is H or C$_{1-3}$alkyl; and

R$^7$ is H, C$_{1-6}$alkyl, C$_{0-4}$alkylene-C$_{6-10}$aryl, or C$_{0-4}$alkylene-C(O)—C$_{1-4}$alkylene-NR$^6{}_2$.

In some embodiments, the compound of Formula (I) comprises Formula (I'):

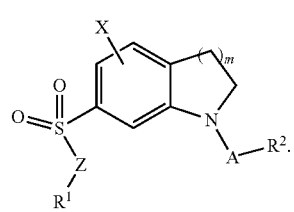

(I')

In some cases, m is 1. In various cases m is 2.

In some embodiments, A is C=O. In various cases, A is SO$_2$.

In various embodiments, Z is

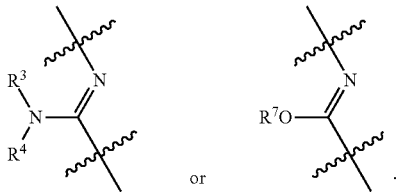

or

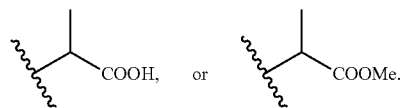

For example, the compound of Formula (I) can have a structure selected from the group consisting of:

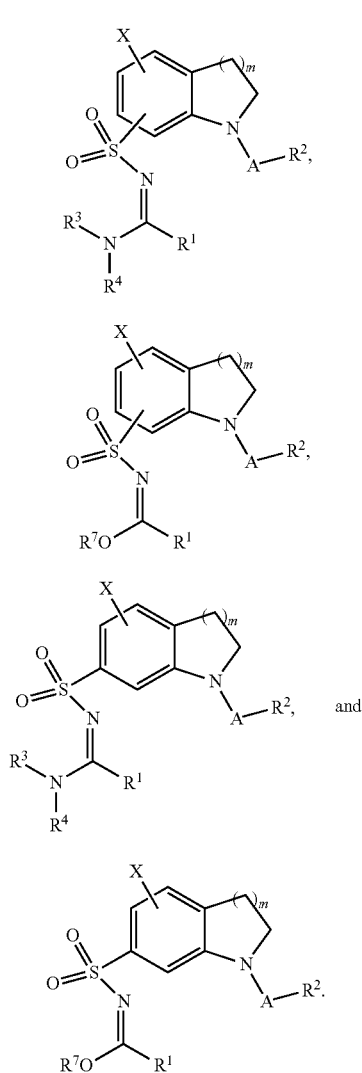

In some cases, $R^3$ and $R^4$ are each independently selected from the group consisting of H, $C_{1-4}$alkyl (e.g., methyl, ethyl, propyl, isopropyl), and $C_{0-4}$alkylene-C(O)$C_{1-4}$alkyl, $C_{0-4}$alkylene-CO$_2$R$^6$ (e.g., derived from an amino acid, wherein the N-terminus of the amino acid is bonded to Z), $C_{0-4}$alkylene-NR$^6{}_2$, or $R^3$ and $R^4$ are taken together with the nitrogen to which they are attached to form a 5-7 membered ring. For example, $R^3$ and $R^4$ can each be H, In some embodiments, each of $R^3$ and $R^4$ is H. In some embodiments, $R^7$ is H, $C_{1-3}$alkyl (e.g., methyl, ethyl, propyl, and isopropyl), $C_{0-4}$alkylene-$C_{6-10}$aryl (e.g., phenyl), or C(O)—$C_{1-2}$alkylene-NR$^6{}_2$ (e.g., derived from an amino acid, wherein the C-terminus of the amino acid is bonded to the oxygen atom and the alkylene is substituted with a side chain of the amino acid). In some embodiments $R^7$ is H.

In various cases, Z is

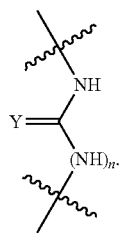

In some cases, Y is O, and Z is

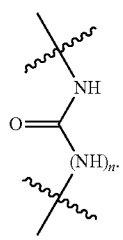

In various embodiments, Y is S and Z is

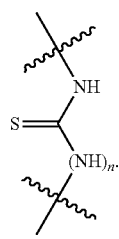

In some embodiments, n is 0 and Z is

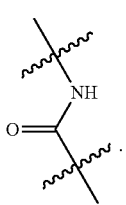

In various embodiments, n is 1 and Z is

In some embodiments, Y is NR⁶ (e.g., NH), n is 0, and Z is (e.g., ).

In some cases, the compound of Formula (I) includes a structure selected from the following:

(IC)

(ID)

(IE)

(IF)

(IC')

(ID')

(IE')

and (IF')

In some embodiments, Z is and the compound of Formula (I) includes a structure:

(IG)

or

In some embodiments, X is ortho to the sulfonyl group. In these embodiments, the compound of Formula (I) can have a structure selected from

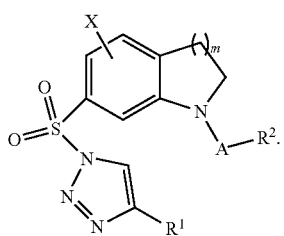
(IA″)

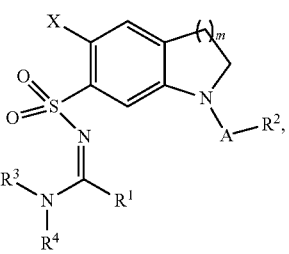
(IB″)

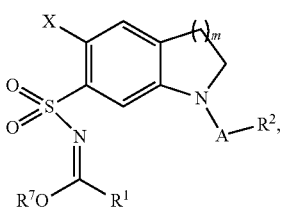
(IC″)

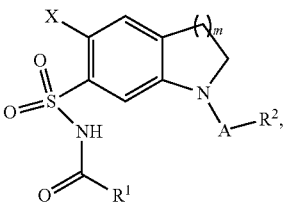
(ID″)

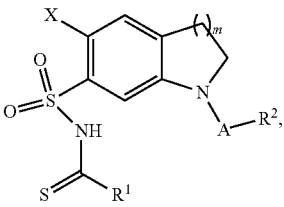
(IE″)

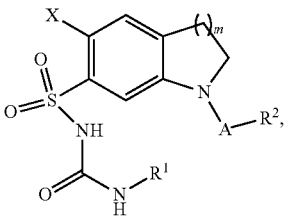
(IF″)

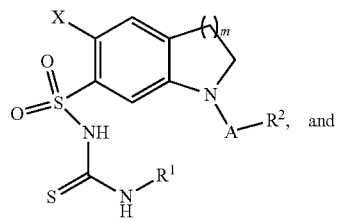

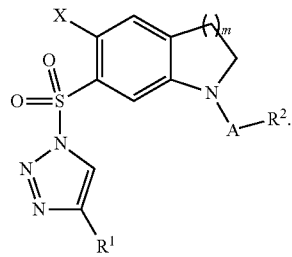
(IG″)

In some cases, X is H, $C_{1-6}$alkyl (e.g., methyl), halo (e.g., F, Cl, Br, I), or $C_{1-6}$alkoxy (e.g., $OCH_3$ or $OCF_3$). For example, X can be H, F, Cl, or Br.

In some embodiments, $R^1$ is $C_{1-6}$alkyl (e.g., methyl, ethyl, propyl, isopropyl, butyl, isobutyl, sec-butyl, tert-butyl, pentyl, and hexyl), $C_{2-6}$alkenyl (e.g., a terminal alkene), $C_{1-4}$alkylene-OH (e.g., $C(CH_3)_2OH$, $CH_2C(CH_3)_2OH$, $CH_2OH$, and $CH_2CH_2OH$) $C_{1-4}$alkylene-CN (e.g., $C_1$-, $C_2$-, or $C_3$-alkylene-CN), $C_{1-4}$alkylene-halo (e.g., $C_1$-, $C_2$-, or $C_3$-alkylene-halo), or $C_{1-4}$alkylene-$CO_2H$ (e.g., $C_1$-, $C_2$-, or $C_3$-alkylene-COOH, or derived from an amino acid wherein the N-terminus of the amino acid is bonded to Z and the alkylene is substituted with the amino acid side chain). For example, $R^1$ can be selected from the group consisting of:

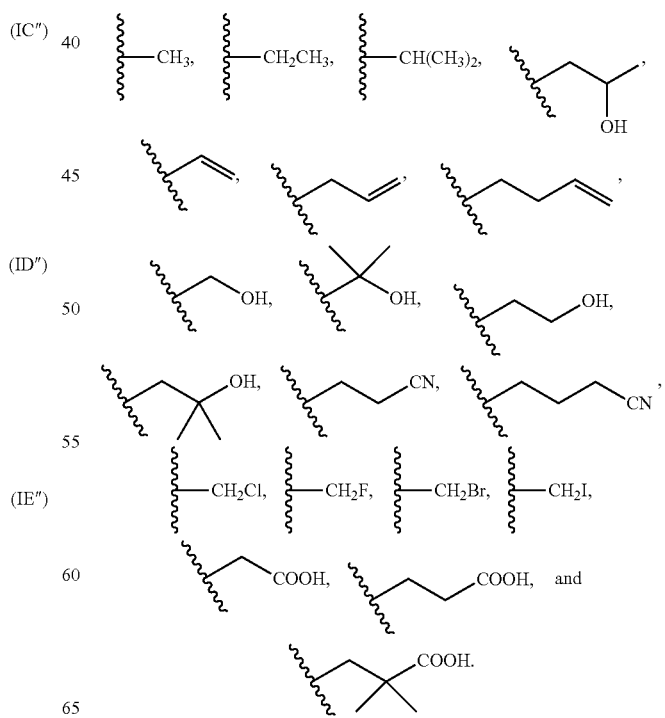

The alkylene, alkyl, and/or alkenyl group can be substituted or unsubstituted in any of these embodiments. In some cases, $R^1$ is $C_{0-4}$alkylene-$C_{3-6}$cycloalkyl or $C_{0-4}$alkylene-heterocycloalkyl having 1, 2, or 3 heteroatoms selected from N, O and S. In some cases, the cycloalkyl group is cyclopropyl, cyclobutyl, cyclopentyl, or cyclohexyl. In various cases, the heterocycloalkyl group is an epoxide. In any of these cases, the alkylene group and/or the cycloalkyl or heterocycloalkyl group can be unsubstituted or substituted. For example, $R^1$ can be selected from the group consisting of:

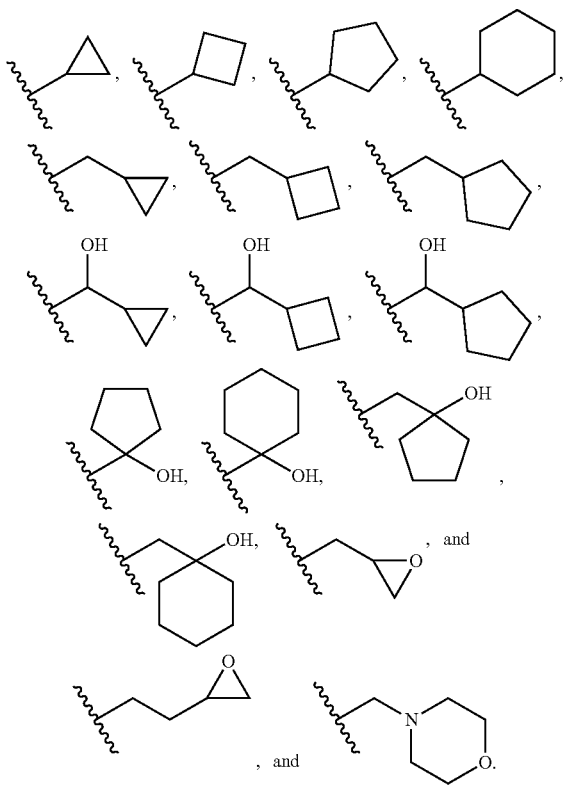

In various embodiments, $R^1$ is $C_{0-4}$alkylene-$C_{6-10}$aryl (e.g., phenyl). In these embodiments, the alkylene group and/or the aryl group can be unsubstituted or substituted. For example, $R^1$ can be selected from the group consisting of:

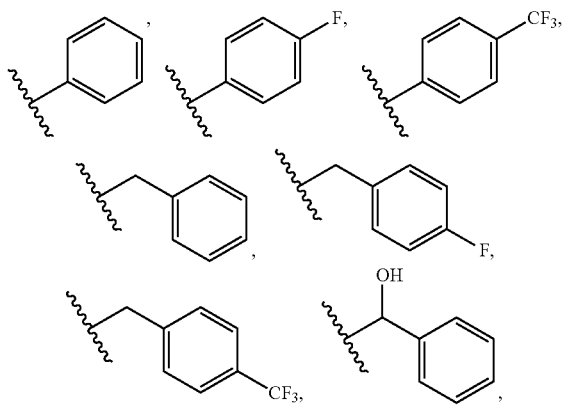

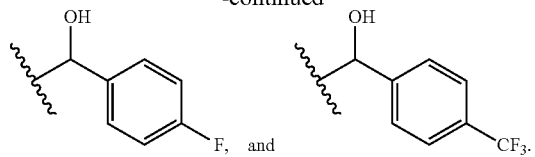

In various cases, $R^1$ is $C_{0-4}$alkylene-$C_{5-10}$heteroaryl having 1, 2, 3, or 4 heteroatoms selected from N, O, and S, such as $C_{0-1}$alkylene-$C_{5-6}$heteroaryl having 1 or 2 heteroatoms (e.g., pyridinyl, pyrimidinyl, oxazolyl, thiazolyl, and imidazolyl). In any of these cases, the alkylene and/or the heteroaryl group can be substituted or unsubstituted. For example, $R^1$ can be selected from the group consisting of:

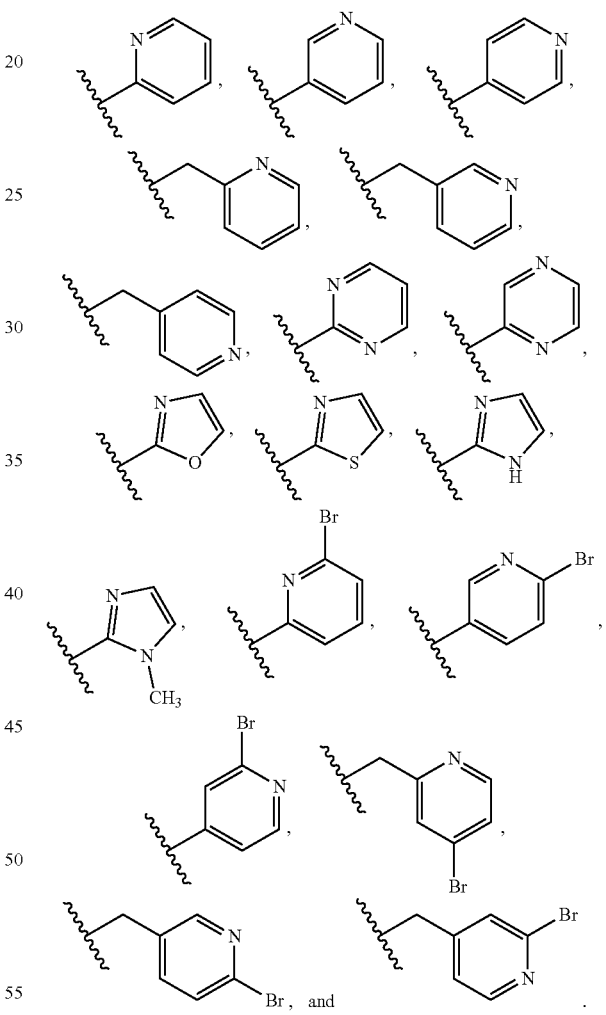

In some embodiments, $R^1$ is $C_{1-4}$alkylene-$NR^6_2$ (e.g., derived from an amino acid wherein the C-terminus of the amino acid is bonded to Z and the alkylene is substituted with the amino acid side chain), $C_{1-4}$alkyleneC(=O)$R^5$, $C_{1-4}$alkyleneC(=O)O$R^5$, $C_{1-4}$alkylene-NHC(O)$R^5$, $C_{1-4}$alkylene-NHC(O)O$R_5$, or $C_{1-4}$alkylene-C(=NO$R^6$)$R^5$, and $R^5$ is $C_{1-3}$alkyl, $C_{0-1}$alkylene-phenyl, or $NR^3R^4$. In any of these embodiments, the alkylene group, alkyl group, and/or phenyl group can be unsubstituted or substituted. For example, $R^1$ can be selected from the group consisting of:

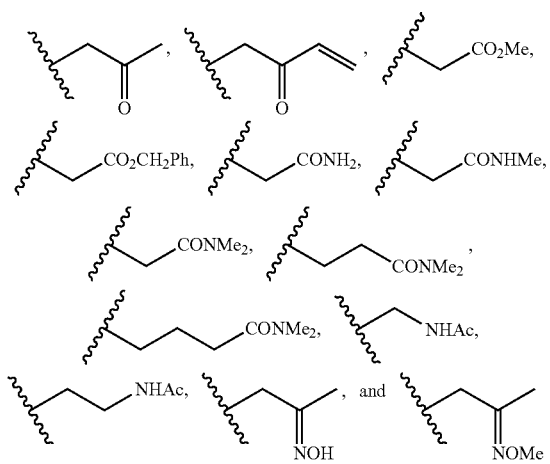

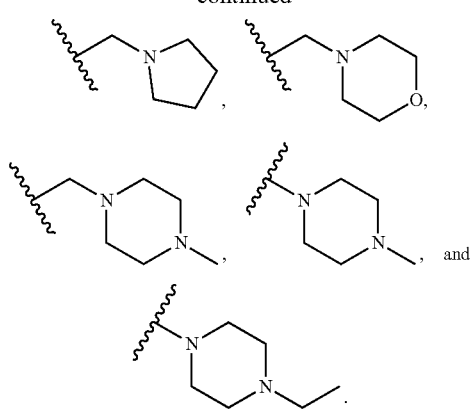

In various embodiments, $R^2$ is $C_{0-4}$alkylene-$C_{6-10}$aryl or $C_{0-4}$alkylene-$C_{5-10}$heteroaryl having 1, 2, 3, or 4 heteroatoms selected from N, O, and S. In some embodiments, the aryl group can be phenyl. In various embodiments, the heteroaryl group can be pyridinyl, thiophenyl, thiazolyl, or isooxazolyl. In any of these embodiments, the alkylene, aryl, and/or heteroaryl group can be substituted or unsubstituted. For example, $R^2$ can be selected from the group consisting of In various embodiments, $R^1$ is $C_{1-4}$alkylene-$OSO_2R^5$, and $R^5$ is $C_{1-3}$alkyl (e.g., methyl, ethyl, propyl, or isopropyl) or phenyl. In any of these embodiments, the alkylene, alkyl, and/or phenyl groups can be substituted or unsubstituted. For example, $R^1$ can be selected from the group consisting of $CH_2OSO_2CH_3$, $CH_2OSO_2CF_3$, $CH_2OSO_2Ph$, and $CH_2OSO_2PhCH_3$. In any of the foregoing, an amino group of $R^1$ can be protected with a protecting group. Some protecting groups contemplated include a Cbz, Boc, or Fmoc group. In some embodiments, $R^1$ includes an alkylating moiety that can covalently bond with, e.g., NDM-1 (such as through Cys-208 or Lys-211) via an $S_N2$ alkylation reaction or a Michael addition.

In some embodiments, $R^2$ is $C_{1-6}$alkyl (e.g., methyl, ethyl, propyl, isopropyl, butyl), $C_{2-6}$alkenyl (e.g., ethylene, propylene), $C_{1-4}$alkylene-OH, $C_{1-4}$alkylene-CN, or $C_{1-4}$alkylene-halo. In any of these embodiments, the alkyl, alkenyl, and/or alkylene group can be substituted or unsubstituted. For example, $R^2$ can be selected from the group consisting of

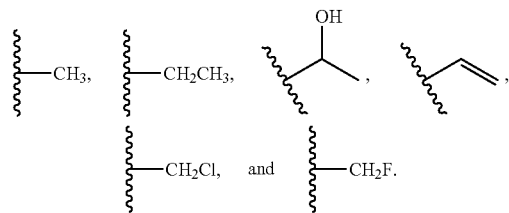

In some cases, $R^2$ is $C_{0-4}$alkylene-$C_{3-6}$cycloalkyl or $C_{0-4}$alkylene-$C_{3-6}$heterocycloalkyl having 1, 2, or 3 heteroatoms selected from N, O and S. In some embodiments, the cycloalkyl group is cyclopropyl, cyclobutyl, cyclopentyl, or cyclohexyl. In some embodiments, the heterocycloalkyl group is piperazinyl or pyrrolidinyl. In any of these embodiments, the alkylene, cycloalkyl, and/or heterocycloalkyl group can be substituted or unsubstituted. For example, $R^2$ can be selected from the group consisting of

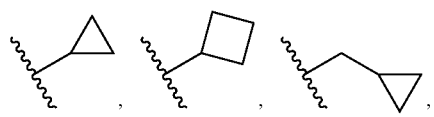

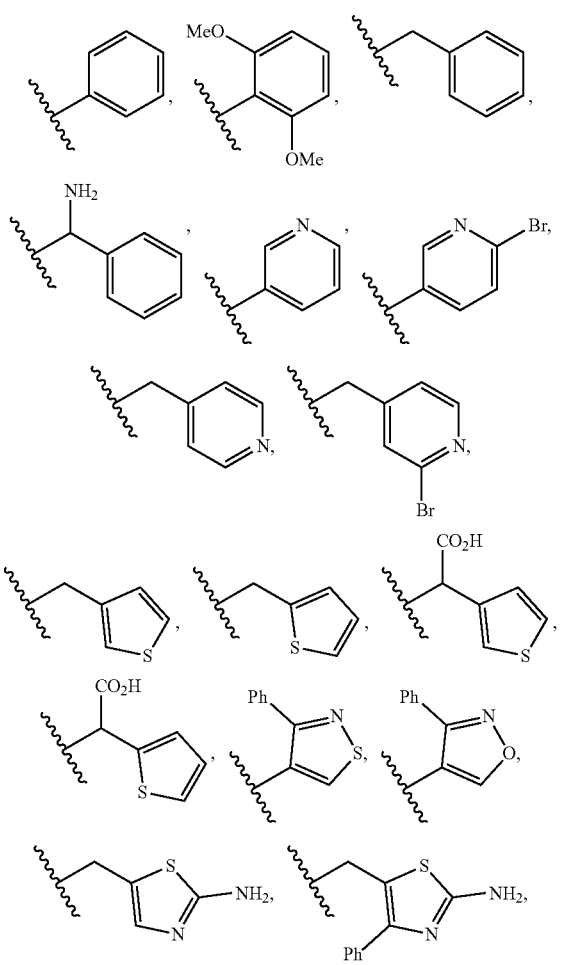

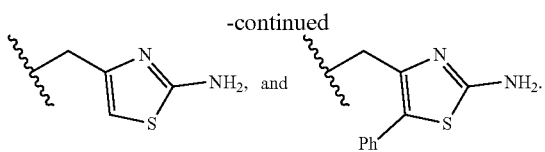

In some cases, $R^2$ is $C_{0-4}$alkylene-$NR^3R^4$. In these embodiments, the alkylene group, $R^3$, and/or $R^4$ can be substituted or unsubstituted. For example, $R^2$ can be selected from the group consisting of

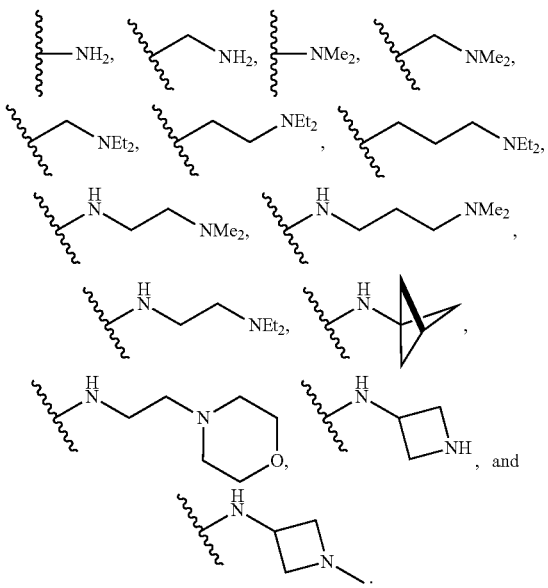

In some embodiments, $R^2$ is $C_{0-4}$alkylene-$OR^5$ or $C_{1-4}$alkylene-$SO_2R^5$. In these embodiments, the alkylene group can be substituted or unsubstituted. For example, $R^2$ can be selected from the group consisting of

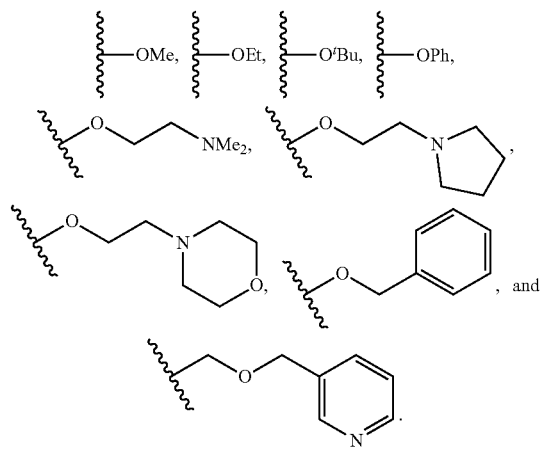

In any of the foregoing, an amino group of $R^2$ can be protected, such as with a Cbz, Boc, or Fmoc group.

In any of the foregoing embodiments in which $R^1$, $R^2$, $R^3$, or $R^4$ can be derived from an amino acid, the amino acid can be, for example, Ala, Arg, Asn, Asp, Cys, Gln, Glu, Gly, His, Ile, Leu, Lys, Met, Phe, Pro, Ser, Thr, Trp, Tyr, or Val. In some embodiments, the amino acid can be Ala, Asp, Glu, Gly, Ile, Leu, Phe, Trp, or Val. In some cases, the amino acid is Ala.

Examples of the compound of Formula (I) include, but are not limited to:

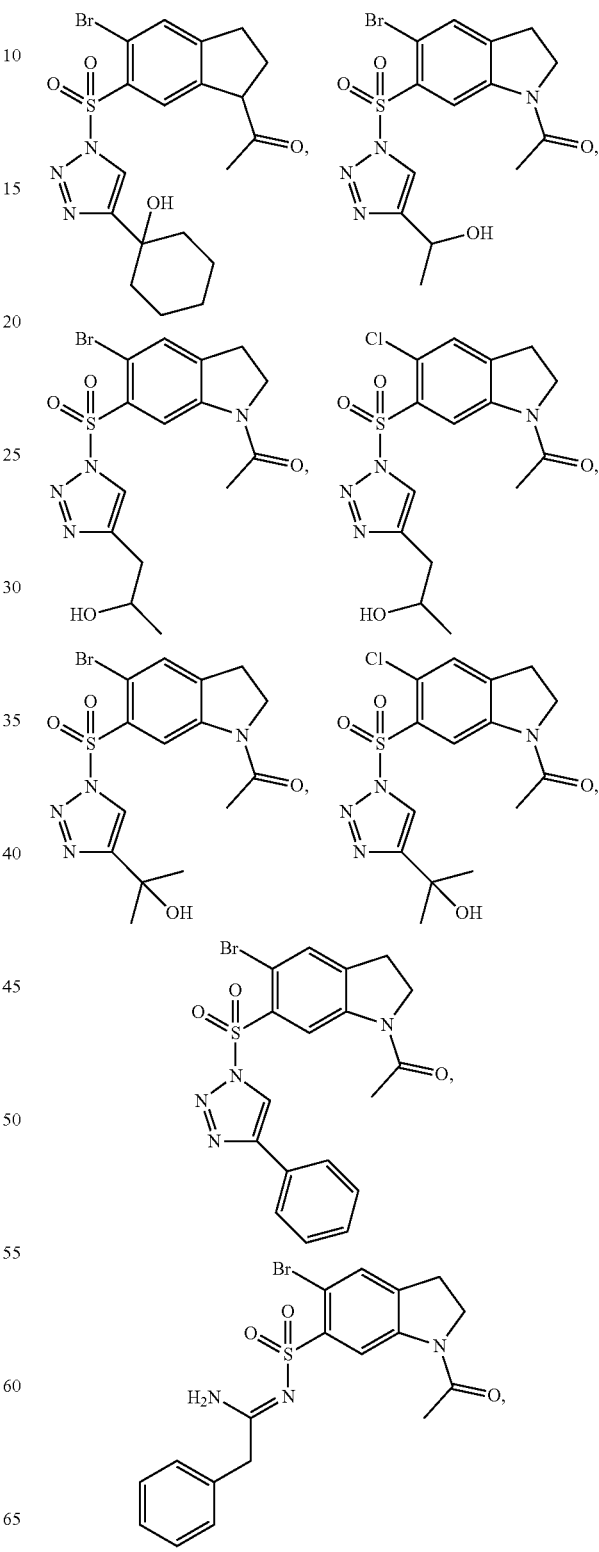

-continued
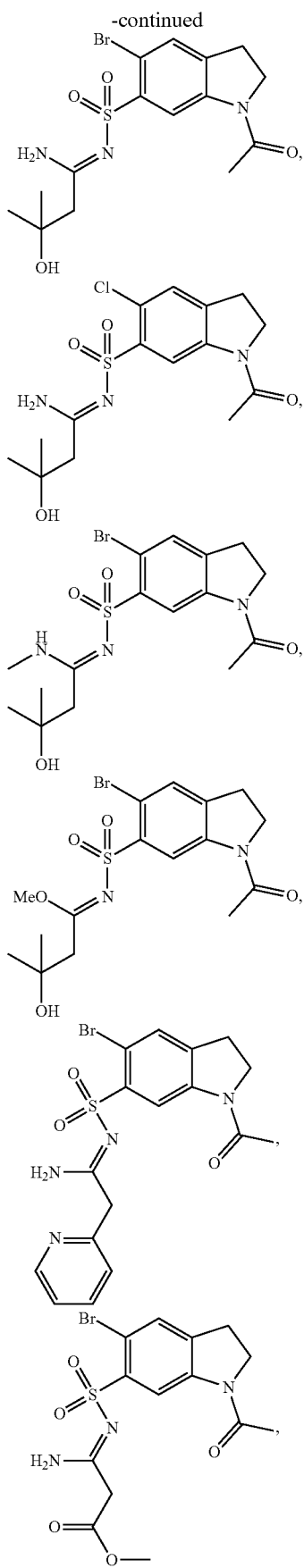
-continued
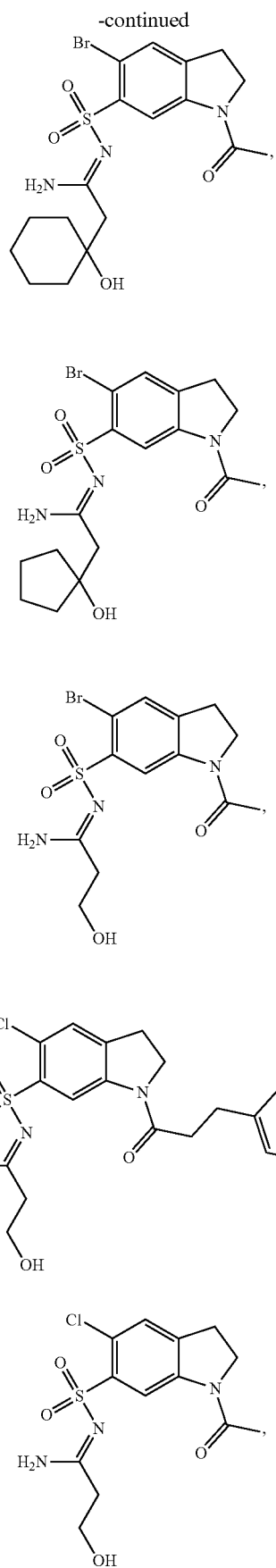

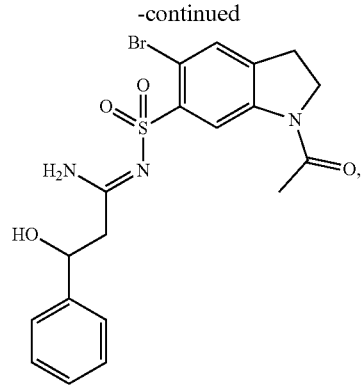
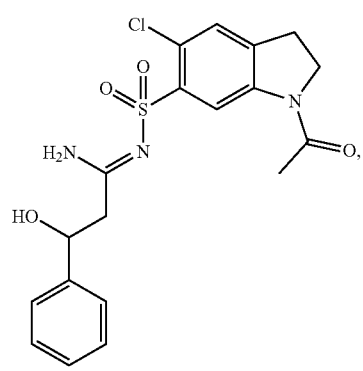
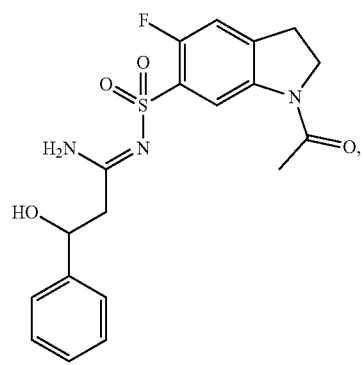
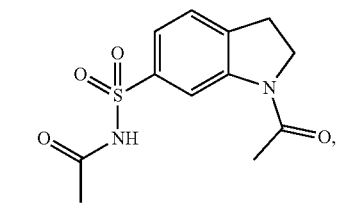
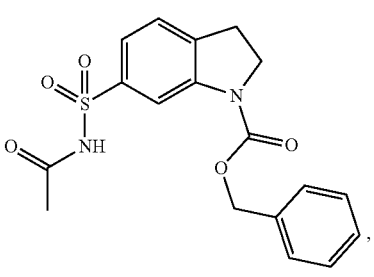
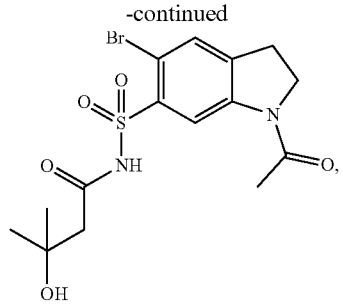
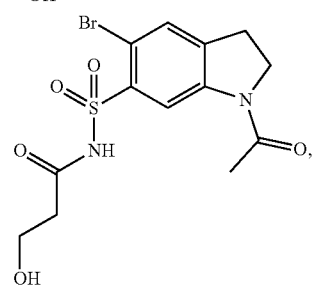
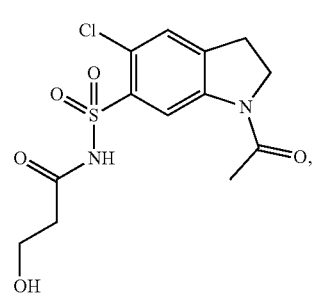
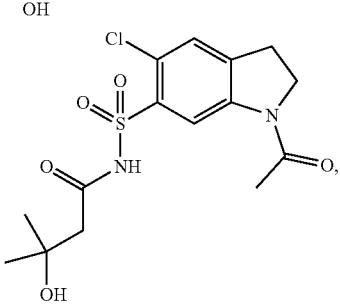
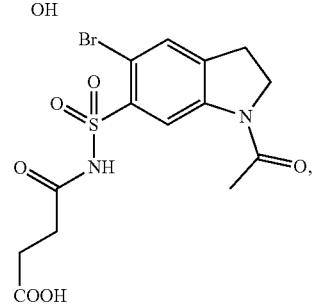
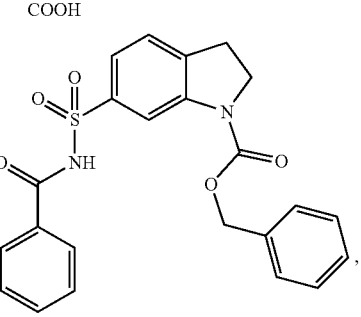

-continued
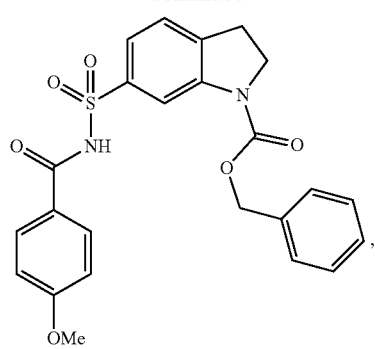
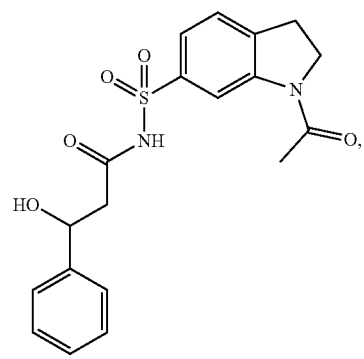
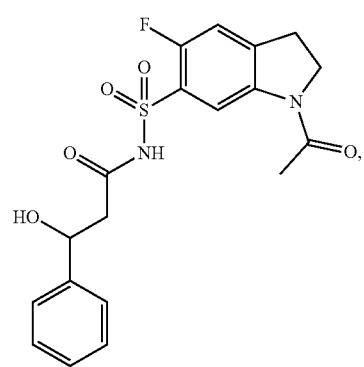
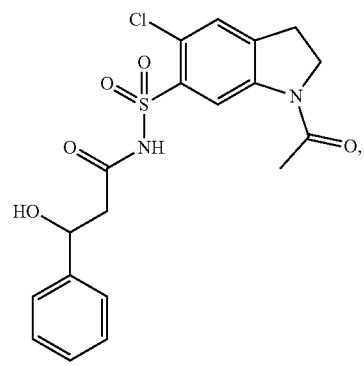
-continued
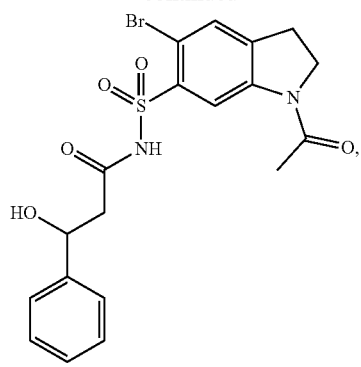 [SMILES: CC(=O)N1CCc2cc(Br)c(S(=O)(=O)NC(=O)CC(O)c3ccccc3)cc21]
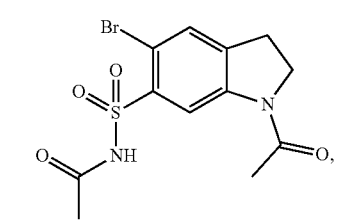
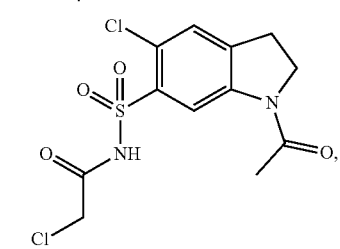
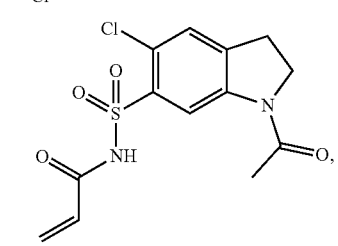
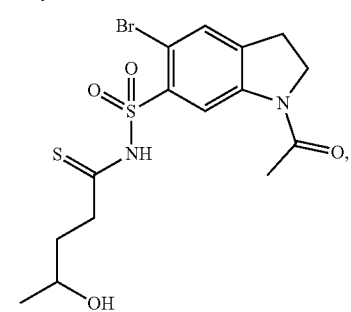
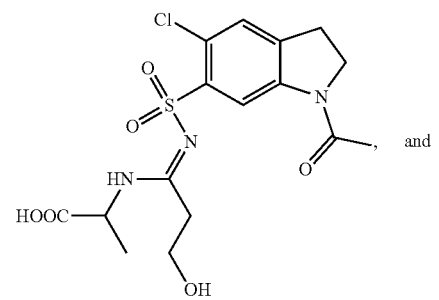, and

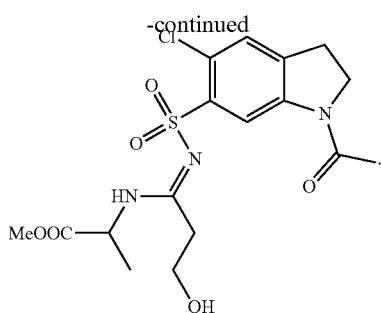

Additionally, salts, hydrates, solvates, and prodrugs of the present compounds also are included in the present disclosure and can be used in the methods disclosed herein. The present disclosure further includes all possible stereoisomers and geometric isomers of the compounds of structural Formulae I, I', IA, IA', IA'', IB, IB', IB'', IC, IC', IC'', ID, ID', ID'', IE, IE', IE'', IF, IF', IF'', IG, IG', and IG''. The present disclosure includes both racemic compounds and optically active isomers. When a compound of structural Formulae I, I', IA, IA', IA'', IB, IB', IB'', IC, IC', IC'', ID, ID', ID'', IE, IE', IE'', IF, IF', IF'', IG, IG', or IG'' is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds disclosed herein are possible, the present disclosure is intended to include all tautomeric forms of the compounds.

Compounds of the disclosure can exist as salts. Pharmaceutically acceptable salts of the compounds of the disclosure can be used in the methods of the disclosure. The term "pharmaceutically acceptable salt," as used herein, refers to any salt (e.g., obtained by reaction with an acid or a base) of a compound of the present disclosure that is physiologically tolerated in the target animal (e.g., a mammal). Salts of the compounds of the present disclosure may be derived from inorganic or organic acids and bases. The term "pharmaceutically acceptable salts" also refers to zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

Compounds of the disclosure may employ deuterium as an isotopic substitution for hydrogen as deuterium is known to modulate metabolism and enhance bioavailability and oral exposure.

Indoline and Tetrahydroquinoline Sulfonyl Compounds as Inhibitors

The compounds disclosed herein can function as DapE and MBL (e.g., NDM-1) inhibitors, and can be tested for inhibition activity by methods well known to those skilled in the art, such as the methods disclosed in the Examples section. The assays indicate that the compounds disclosed herein can have $IC_{50}$ values in ranges described above, such as in a range of about 1 μM to about 300 μM, or about 1 μM to about 125 μM. See the Examples section.

Without being bound by any particular theory, the indoline and tetrahydroquinoline sulfonyl compounds described herein are capable for bridging two active zinc atoms of MBLs (e.g., NDM-1), as shown in FIG. 1, suggesting a common dizinc-binding mode, as shown below.

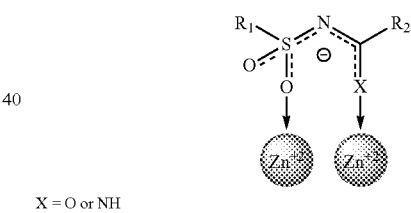

X = O or NH

In some embodiments, tosyl derivatives of the compounds disclosed herein exhibited decreased NDM-1 inhibitory activity, as shown below. Therefore, without being bound by any particular theory, the indoline scaffold contributes to NDM-1 inhibition.

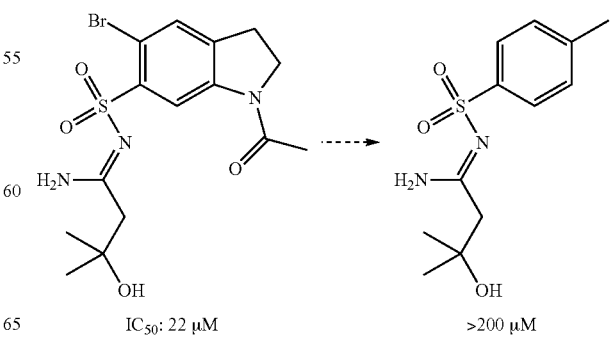

$IC_{50}$: 22 μM         >200 μM

Also without being bound by any particular theory, the presence of a group with a free lone pair (a lone pair donor) positioned β- to the sulfonyl amidine can improve potency (i.e., NDM-1 or DapE inhibition).

Also without being bound by any particular theory, the degree and bulk of symmetrical alkyl substitution β to the sulfonyl amidine can be inversely related to potency for alcohol derivatives, as shown below.

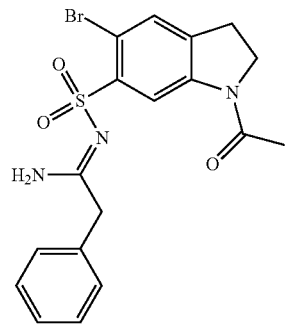

IC50: 110 µM

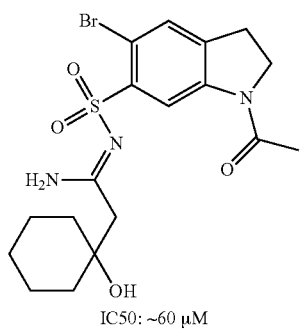

IC50: ~60 µM

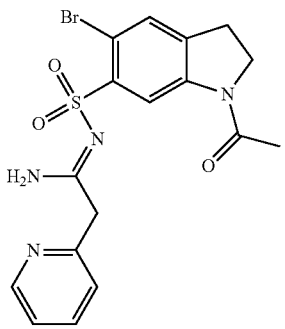

~15 µM

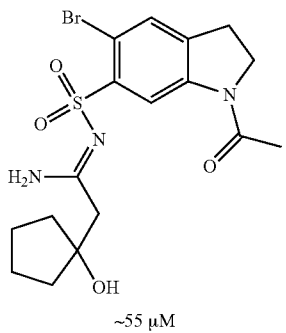

~55 µM

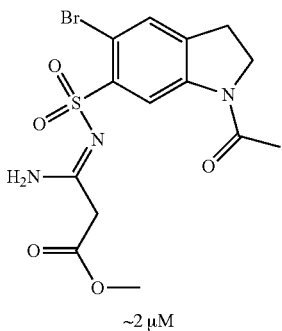

~2 µM

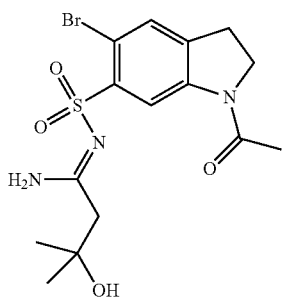

22.0 +/− 1 µM

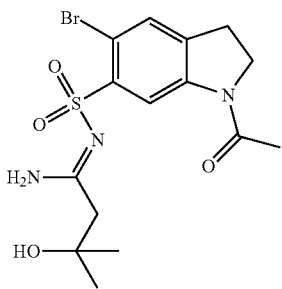

22 +/− 1 µM

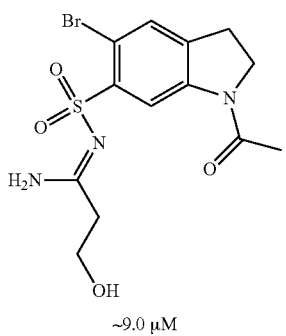

~9.0 µM

In some embodiments, N-acylsulfonamide shows improved inhibition over its sulfonyl amidine counterpart, as shown below, likely owing to ionization of the N-acylsulfonamide moiety at neutral pH (pKa ~5.0) leading to better zinc-binding.

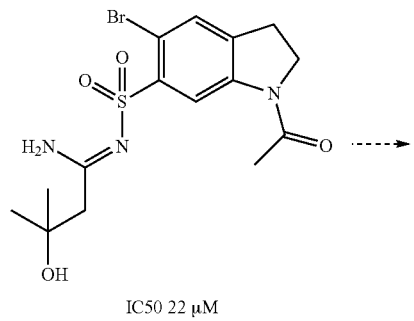

IC50 22 µM

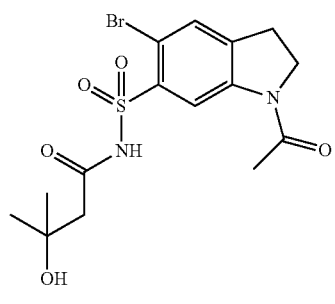

8.7 µM

Preparation of the Indoline and Tetrahydroquinoline Sulfonyl Compounds

The schemes that depict indolines also are applicable to tetrahydroquinolines and vice versa.

Compounds of the present disclosure can be prepared by any method known in the art, such as, for example, by copper(I)-catalyzed couplings of sulfonyl azides and alkynes. Like alkyl azides, sulfonyl azides and alkynes undergo a 3+2 cycloaddition in the presence of a copper(I) catalyst to yield the corresponding triazole. See Raushel, J.; Fokin, V. V. *Organic Letters* 2010, 12, 4952-4955. Evidence that this reaction proceeds through a cuprated triazole intermediate is found in Yoo, E. J.; Ahlquist, M.; Bae, I.; Sharpless, B. K.; Fokin, V. V.; Chang, S. *The Journal of Organic Chemistry* 2008, 73, 5520-5528, as depicted in Scheme 1 Scheme 1.

Scheme 1. Copper(I)-Catalyzed Coupling of Sulfonyl Azides and Alkynes

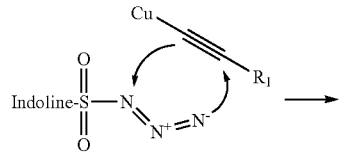

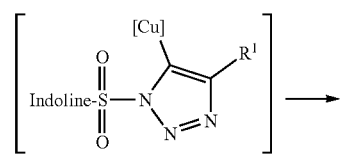

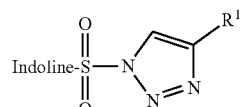

Under slightly modified conditions, the cuprated triazole intermediate eliminates dinitrogen to yield a highly electrophilic ketenimine, which reacts readily with amines, alcohols, or water to form N-sulfonylamidines, N-sulfonylimidates, or N-acylsulfonamides (respectively), as shown in Scheme 2, below, and described in Yoo et al.

Scheme 2. Three-component couplings of sulfonyl azides, alkynes, and nucleophiles occur via a ketenimine intermediate, for example where Nu—H is H$_2$N—H (i.e., ammonia).

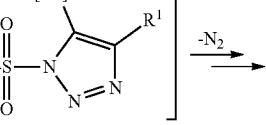

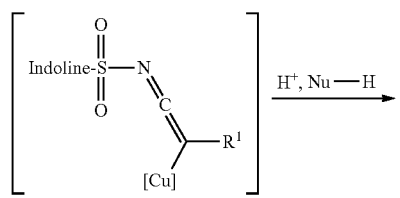

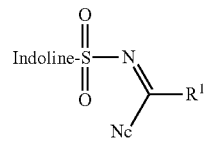

Sulfonyl azides can be prepared by reacting a sulfonyl chloride with an azide (e.g., sodium azide) or a primary sulfonamide with a diazo transfer agent, such as imidazole-1-sulfonyl azide. Acyl sulfonamides also can be prepared by reacting sulfonamide starting materials with acyl chlorides. Scheme 3, below, provides an overview of reaction pathways that result in the compounds of the disclosure.

Scheme 3. Overview of Reaction Pathways
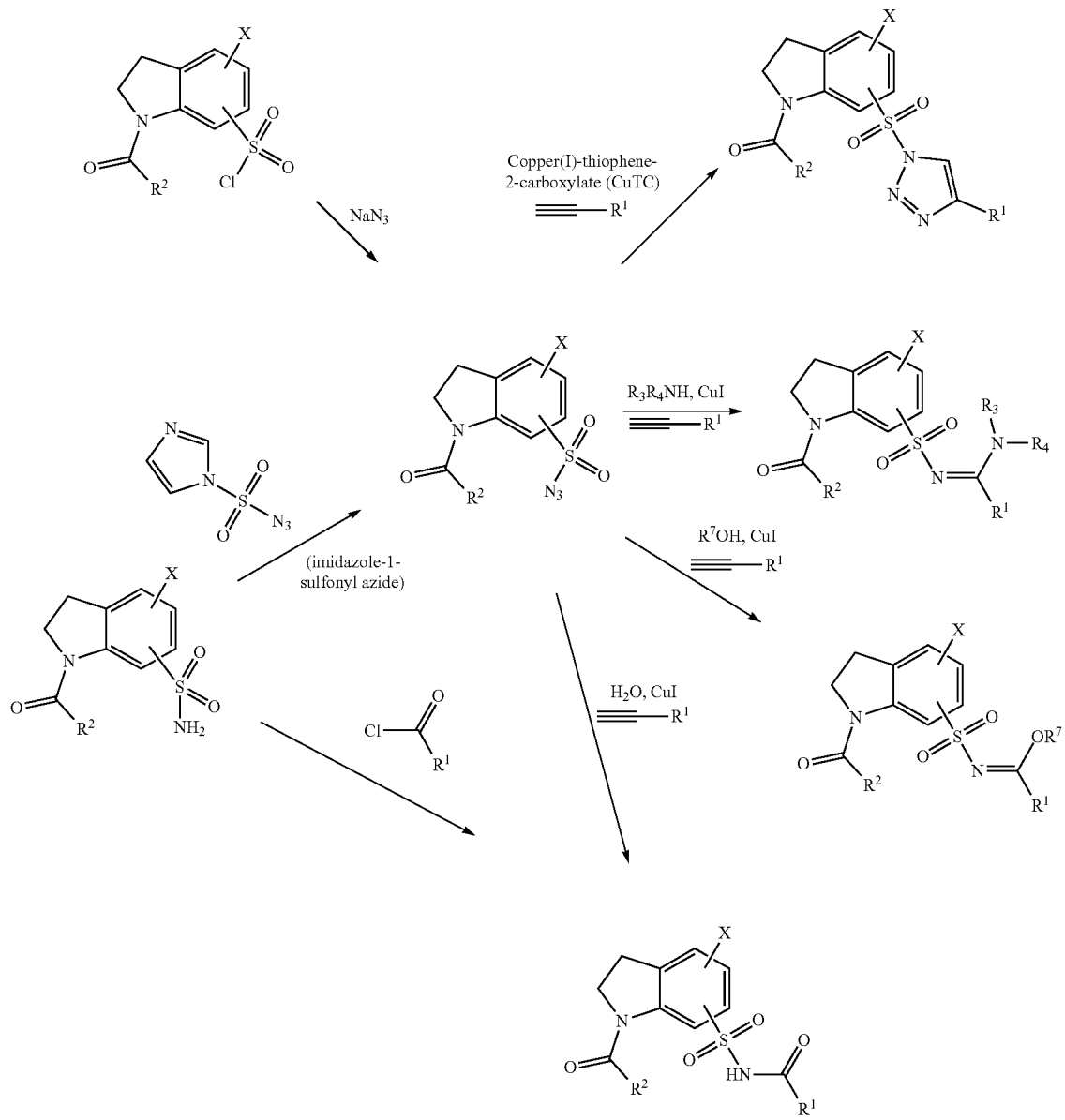
In some embodiments, the nitrogen of the indoline can be protected, such as by reacting it with benzyl chloroformate ("CbzCl") before the copper (I) coupling reaction, and then reducing the protected group to form an acyl group, as shown in Scheme 4, below.
Scheme 4. Protection/Reduction of Indoline Nitrogen
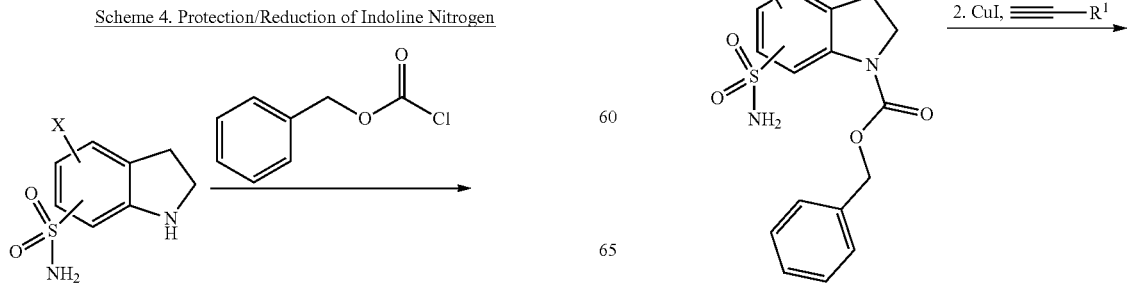

53

-continued

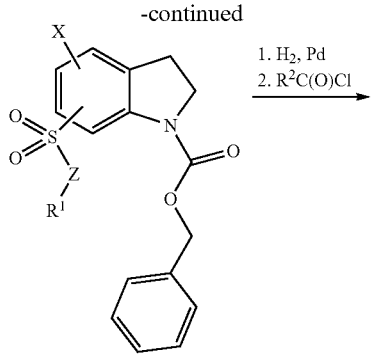

1. H₂, Pd
2. R²C(O)Cl

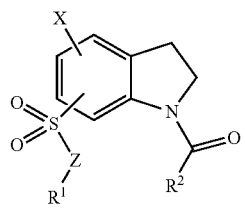

In some embodiments, the nitrogen of the indoline can be protected with, for example, a tert-butyl carbamate group before the sulfonating the indoline, and then subsequently deprotecting it, as shown in Scheme 5, below.

54

-continued

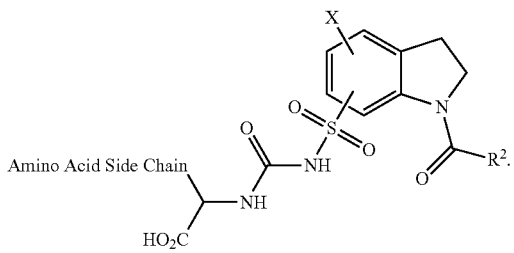

In some of these embodiments, the indoline sulfonyl compound of the disclosure can be prepared by coupling the amino group of a sulfonamide with the carboxyl group of an N-protected amino acid, using any coupling agent known in the art (e.g., carbodiimide such as DCC, DIC, EDC, or CIC; phosphonium such as BOP or PyBOP; uronium reagent such as HATU or HBTU; imidazolium such as CDI; organophosphorus; acid chloride such as pivaloyl chloride or 2, 4, 6-trimethylbenzoyl chloride; chloroformate, or pyridinium reagent), and then deprotecting the protected nitrogen of the amino acid, as shown in Scheme 6, below.

Scheme 5. Acylation of Indoline

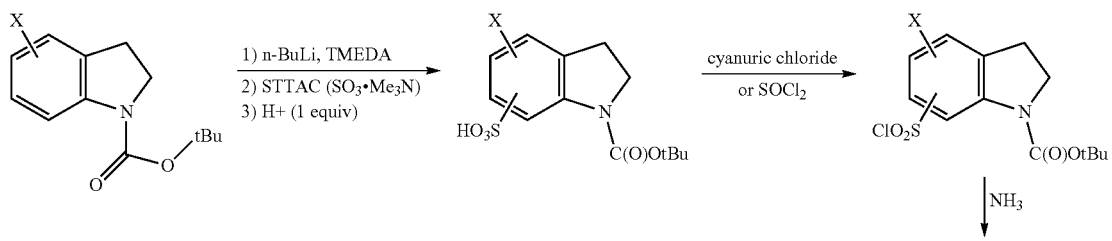

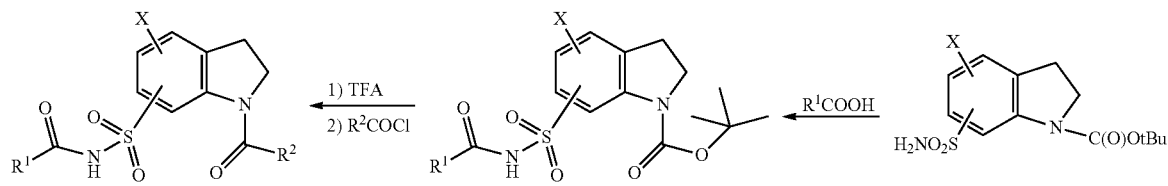

In some embodiments, R¹ is derived from an amino acid:

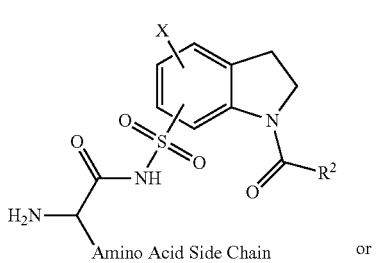

or

Scheme 6. Coupling the C-Terminus of an Amino Acid to a Sulfonamide

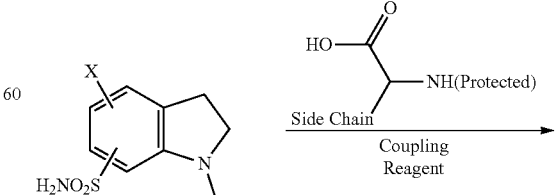

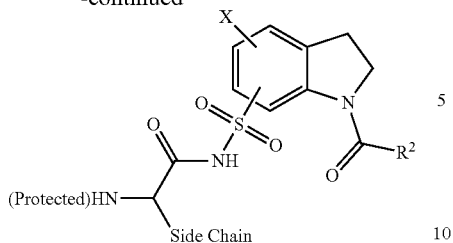

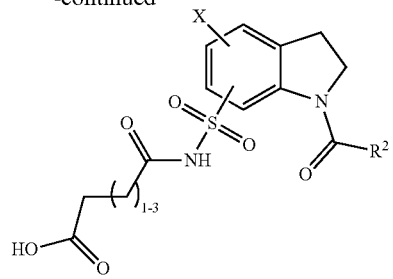

In cases wherein Z is a thioamide, the thioamide can be prepared by reacting a sulfonyl azide with a thiol and an alkyne with the desired R-group, as shown in Scheme 9, below.

Scheme 9. Preparation of Thioamides

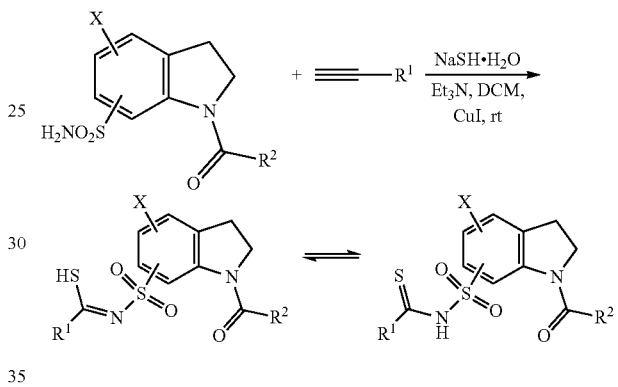

In various of these embodiments, the indoline sulfonyl compound of the disclosure can be prepared by coupling the amino group of a sulfonamide with phosgene, and then the amino group of an amino acid, as shown in Scheme 7, below.

Scheme 7. Coupling the N-Terminus of an Amino Acid to a Sulfonamide

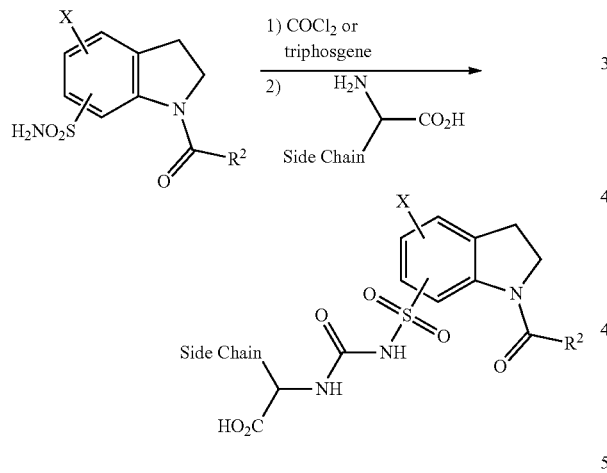

In embodiments, wherein the compound is a sulfonyl urea or a sulfonyl thiourea, the compound can be prepared by coupling a sulfonamide with an isocyanate or an isothiocyanate, as shown in Scheme 610, below.

Scheme 610. Preparation of Sulfonyl Ureas and Sulfonyl Thioureas

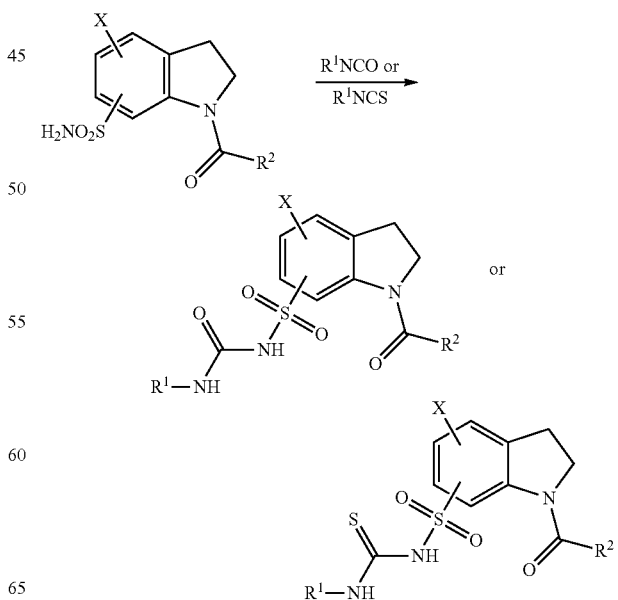

In various embodiments when $R^1$ is a carboxylic acid, the indoline sulfonyl compound can be prepared by reacting a sulfonamide with a cyclic anhydride, as shown in Scheme 8, below.

Scheme 8. Coupling a Cyclic Anhydride to a Sulfonamide

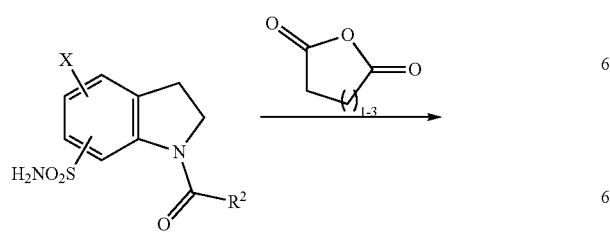

In any of the foregoing Schemes that include an amino acid side chain, the side chain can be from, for example, Ala, Arg, Asn, Asp, Cys, Gln, Glu, Gly, His, Ile, Leu, Lys, Met, Phe, Pro, Ser, Thr, Trp, Tyr, or Val. In some embodiments the side chain can be from Ala, Asp, Glu, Gly, Ile, Leu, Phe, Trp, or Val (e.g., Ala).

Additional synthetic procedures for preparing the inhibitors disclosed herein can be found in the Examples section.

Methods

The compounds of structural Formulae I, I', IA, IA', IA", IB, IB', IB", IC, IC', IC", ID, ID', ID", IE, IE', IE", IF, IF', IF"', IG, IG', and IG" inhibit DapE and/or MBLs, such as NDM-1, IMP-1, and VIM-2, and are useful in the treatment of a variety of diseases and conditions. In particular, the compounds disclosed herein are used in methods of treating a disease or condition wherein inhibition of DapE and/or a MBL, such as NDM-1, provides a benefit, for example, a bacterial infection.

The methods comprise administering a therapeutically effective amount of a compound of structural Formulae I, I', IA, IA', IA", IB, IB', IB", IC, IC', IC", ID, ID', ID", IE, IE', IE", IF, IF', IF"', IG, IG', and/or IG" to an individual in need thereof. The present methods also encompass administering a second therapeutic agent to the individual in addition to the compound of structural Formulae (I, I', IA, IA', IA", IB, IB', IB", IC, IC', IC", ID, ID', ID", IE, IE', IE", IF, IF', IF"', IG, IG', and IG". The second therapeutic agent is selected from drugs known as useful in treating the disease or condition afflicting the individual in need thereof, e.g., an antibiotic known as useful in treating a particular bacterial infection. In some particular embodiments, the compounds disclosed herein are administered with a β-lactam antibiotic drug. Co-administration of the compounds disclosed herein with a β-lactam antibiotic drug maintains and/or enhances the effectiveness of the β-lactam antibiotic drug by preventing destruction of the β-lactam antibiotic drug by MBLs, such as NDM-1, IMP-1, and VIM-2. In some embodiments, the compound disclosed herein is administered simultaneously with the second therapeutic agent. In various embodiments, the compound disclosed herein and the second therapeutic agent are administered separately.

Thus, one aspect of the disclosure relates to a method of inhibiting DapE comprising contacting DapE with a compound of Formulae I, I', IA, IA', IA", IB, IB', IB", IC, IC', IC", ID, ID', ID", IE, IE', IE", IF, IF', IF"', IG, IG', and/or IG" in an amount effective to inhibit DapE. For example, DapE can be inhibited in a cell by contacting the cell with a compound of Formulae I, I', IA, IA', IA", IB, IB', IB", IC, IC', IC", ID, ID', ID", IE, IE', IE", IF, IF', IF"', IG, IG', and/or IG". The contacting of the cell can occur in vitro or in vivo. In some cases, contacting of the cell occurs in vitro. In other cases, contacting of the cell occurs in vivo. The compounds disclosed herein can contact a cell in vivo by administering the compound to a subject in need of DapE inhibition. Therefore, the disclosure includes administering one or more compounds of Formulae I, I', IA, IA', IA", IB, IB', IB", IC, IC', IC", ID, ID', ID", IE, IE', IE", IF, IF', IF"', IG, IG', and/or IG" described herein to a subject, such as a human, in need thereof. In some embodiments, the subject suffers from a bacterial infection.

Another aspect of the disclosure relates to a method of inhibiting MBLs, such as NDM-1, IMP-1, and VIM-2, comprising contacting the MBL (e.g., NDM-1, IMP-1, and/or VIM-2) with a compound of Formulae I, I', IA, IA', IA", IB, IB', IB", IC, IC', IC", ID, ID', ID", IE, IE', IE", IF, IF', IF"', IG, IG', and/or IG" in an amount effective to inhibit the MBL. For example, a MBL (e.g., NDM-1) can be inhibited in a cell by contacting the cell with a compound of Formulae I, I', IA, IA', IA", IB, IB', IB", IC, IC', IC", ID, ID', ID", IE, IE', IE", IF, IF', IF"', IG, IG', and/or IG". The contacting of the cell can occur in vitro or in vivo. In some cases, contacting of the cell occurs in vitro. In other cases, contacting of the cell occurs in vivo. The compounds disclosed herein can contact a cell in vivo by administering the compound to a subject in need of MBL (e.g., NDM-1) inhibition. Therefore, the disclosure includes administering one or more compounds of Formulae I, I', IA, IA', IA", IB, IB', IB", IC, IC', IC", ID, ID', ID", IE, IE', IE", IF, IF', IF"', IG, IG', and/or IG" described herein to a subject, such as a human, in need thereof. In some embodiments, the subject suffers from a bacterial infection.

Further guidance for using compounds of Formulae I, I', IA, IA', IA", IB, IB', IB", IC, IC', IC", ID, ID', ID", IE, IE', IE", IF, IF', IF"', IG, IG', and/or IG" for inhibiting DapE and/or MBL can be found in the Examples section, below.

Administration of the Inhibitors

The methods disclosed herein can be accomplished by administering a compound of structural Formulae I, I', IA, IA', IA", IB, IB', IB", IC, IC', IC", ID, ID', ID", IE, IE', IE", IF, IF', IF"', IG, IG', and/or IG" as the neat compound or as a pharmaceutical composition. In some embodiments, the pharmaceutical composition include a compound disclosed herein and a pharmaceutically acceptable carrier or vehicle. Administration of a pharmaceutical composition, or neat compound, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising the compounds disclosed herein and, optionally, a second therapeutic agent useful in the treatment of diseases and conditions wherein inhibition of DapE and/or MBL provides a benefit, packaged separately or together, and an insert having instructions for using these active agents.

In many embodiments, the compounds disclosed herein are administered in conjunction with a second therapeutic agent useful in the treatment of a disease or condition wherein inhibition of DapE and/or MBL (e.g., NDM-1) provides a benefit (e.g., β-lactam antibiotic drug). The second therapeutic agent is different from the compounds disclosed herein, and can be small molecules or macromolecules, such as a proteins, antibodies, peptibodies, DNA, RNA, or fragments of such macromolecules.

The second therapeutic agent is administered in an amount to provide its desired therapeutic effect. The effective dosage range for each second therapeutic agent is known in the art, and the second therapeutic agent is administered to an individual in need thereof within such established ranges.

In the present method, a therapeutically effective amount of one or more of a compound disclosed herein, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

Thus, also provided herein are pharmaceutical formulations that include a compound of Formulae I, I', IA, IA', IA'', IB, IB', IB'', IC, IC', IC'', ID, ID', ID'', IE, IE', IE'', IF, IF', IF'', IG, IG', and/or IG'', or a pharmaceutically acceptable salt, as previously described herein, and one or more pharmaceutically acceptable excipients.

The compounds disclosed herein and other pharmaceutically active compounds, if desired, can be administered to a patient or subject by any suitable route, e.g. orally, rectally, parenterally, (for example, intravenously, intramuscularly, or subcutaneously, also including, intracoronary, intradermal, intramammary, intraperitoneal, intraarticular, intrathecal, retrobulbar, intrapulmonary injection and/or surgical implantation at a particular site) intracisternally, intravaginally, intraperitoneally, intravesically, sublingually, rectally, intrathecally through lumbar puncture, transurethrally, percutaneous, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quatemary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Pharmaceutical compositions include those wherein a compound disclosed herein is administered in an effective amount to achieve its intended purpose. The exact formulation, route of administration, and dosage is determined by an individual physician in view of the diagnosed condition or disease. Dosage amount and interval can be adjusted individually to provide levels of a compound disclosed herein that is sufficient to maintain therapeutic effects.

Toxicity and therapeutic efficacy of the compounds disclosed herein can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound disclosed herein required for use in therapy varies with the nature of the condition being treated, the length of time that activity is desired, and the age and the condition of the patient, and ultimately is determined by the attendant physician. Dosage amounts and intervals can be adjusted individually to provide plasma levels of the inhibitors that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present TAP protein inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formulae I, I', IA, IA', IA", IB, IB', IB", IC, IC', IC", ID, ID', ID", IE, IE', IE", IF, IF', IF", IG, IG', and/or IG" used in a method of the present invention can be administered in an amount of about 0.005 to about 500 milligrams per dose, about 0.05 to about 250 milligrams per dose, or about 0.5 to about 100 milligrams per dose. For example, a compound disclosed herein can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a compound disclosed herein, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

Example 1

Preparation of Sulfonyl Indoline Compounds Using Methylbutynol

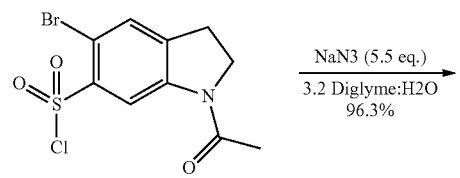

-continued

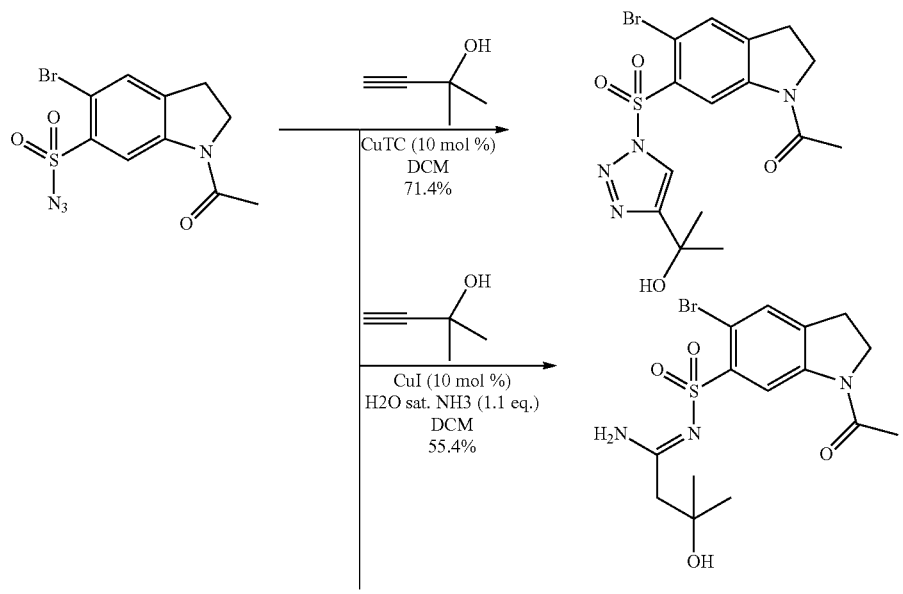

Example 2

Preparation of Sulfonyl Azide

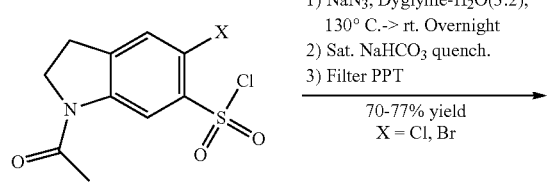

1) NaN$_3$, Dyglyme-H$_2$O(3:2), 130° C.-> rt. Overnight
2) Sat. NaHCO$_3$ quench.
3) Filter PPT 70-77% yield
X = Cl, Br -continued

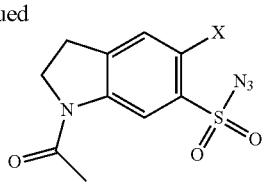

Sulfonyl chloride and NaN$_3$ were added to a three neck round bottom equipped with an addition funnel and long neck under argon. Then, freshly purchased anhydrous diglyme was added to the reaction vessel at room temperature and then lowered onto a heating mantle set to 130° C. with vigorous stirring. After 5 minutes when the starting material had dissolved, 20 mL of deionized H$_2$O was added to the addition funnel and slowly dripped into the reaction vessel over 10 minutes. The reaction was heated for an hour afterwards, then allowed to cool to room temperature with stirring overnight. The reaction was monitored by TLC and HPLC. Upon completion, the reaction mixture was dripped into saturated bicarbonate, producing a tan precipitate. The product slurring was then dissolved in ethyl acetate and the organic layer was collected. The aqueous layer was then extracted 3× with ethyl acetate and all the organic layers were combined and dried over sodium sulfate. The organic layer was concentrated to a brown syrup containing residual diglyme. The product was crystallized from the syrup by dilution was petroleum ether to produce a white fluffy powder at in high purity. The product was collected by filtration and used without further purification.

Example 3

Deprotection of 6-Substituted N-Cbz-Sulfonamide

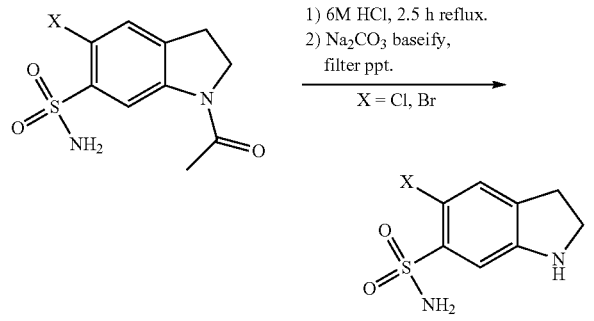

Sulfonamide starting material was heated at 110° C. in 3 mL of 6N HCl for 2.5 h or until HPLC indicated consumption of the starting material. Then, the homogenous reaction was dripped into a small Erlenmeyer flask with 5 mL of saturated bicarbonate to neutralize and cause the product to precipitate. The product was filtered and washed with petroleum ether and used without further purification.

Example 4

Carboxybenzyl Protection of Sulfonamide Indoline Aniline Nitrogen

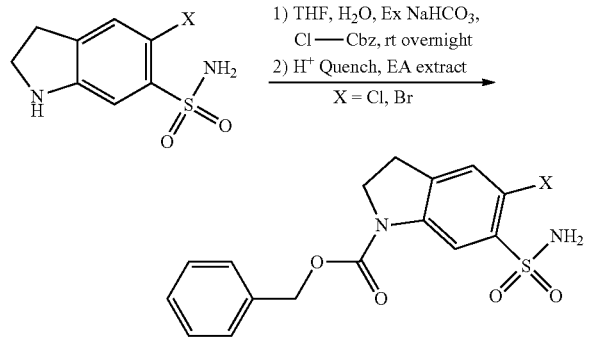

A 6- or 7-sulfonamide indoline was combined in a three-neck round bottom flask with THF followed by 11 equiva-lents of sodium bicarbonate and H$_2$O under inert atmosphere. Then, benzylchloroformate was added via syringe over 7 minutes and the reaction was left to stir overnight. The reaction was monitored using HPLC. Upon workup, the excess HCO$_3$ was removed via filtration and the filtrate was acidified. The product was then extracted from the aqueous layer 3-4.∴ with ethyl acetate. The organic fractions were combined, washed once with brine, and dried with magnesium sulfate. The organic layer was filtered through a cotton plug and the product concentrated to minimal solvent. The product was triturated with ether and product was collected via vacuum filtration to yield an off white solid in moderate yield.

Example 5

General Procedure for Preparation of Sulfonyl Amidine Compounds

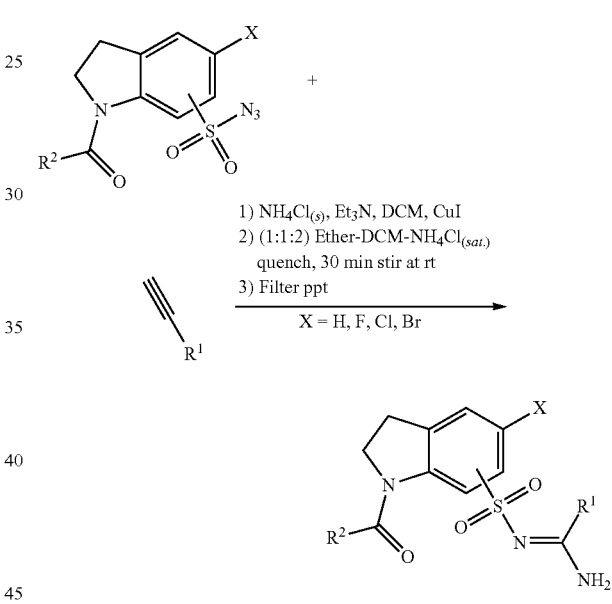

Sulfonyl azide starting material was combined with NH$_4$Cl, and copper iodide, followed by CH$_2$Cl$_2$, Et$_3$N and the alkyne. The reaction was allowed to react under positive pressure inert gas over 2-3 hours or until effervescence ceased. The reaction was monitored with TLC and HPLC. The reaction was quenched with by diluting with 2 mL DCM and 2 mL ammonium chloride, and then stirred at room temperature under N$_2$ for 30 minutes. If a precipitate formed, it was collected with vacuum filtration and washed with saturated NH$_4$Cl, 10% citric acid, deionized H2O, and petroleum ether. Otherwise the organic layer was collected and concentrated to dryness. The crude product was dissolved in minimal MeOH-acetonitrile-DMF, passed through an activated carbon/cotton plug, dripped into cold either, and left to stir for 30 min. The product precipitate was then collected via vacuum filtration, washed with ether and petroleum ether, and all collected final products were analyzed with HPLC to verify purities that can be above 95%.

Example 6

General Procedure for Preparation of Sulfonamide Compounds

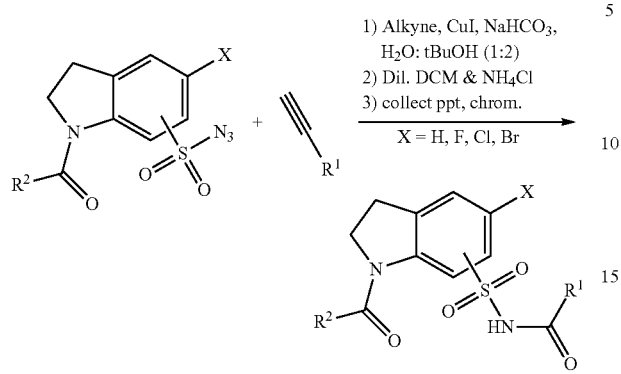

1) Alkyne, CuI, NaHCO$_3$,
   H$_2$O: tBuOH (1:2)
2) Dil. DCM & NH$_4$Cl
3) collect ppt, chrom.

X = H, F, Cl, Br

To a mixture of sulfonyl azide and CuI, was added a mixture of 2:1 tBuOH:H$_2$O and trimethylamine, before adding the alkyne. The reaction mixture was stirred under positive pressure inert atmosphere. The reaction was monitored with TLC and HPLC. Upon completion, the reaction was quenched by diluting with 2 mL DCM and 2 mL ammonium chloride and stirred at room temperature under N$_2$ for 30 minutes. If a precipitate did not form at room temperature, then the reaction was cooled in an ice bath to form the precipitate. The precipitate was then collected with vacuum filtration and washed with saturated 10% citric acid, deionized H$_2$O, and petroleum ether. The crude product was dissolved in minimal MeOH and acetonitrile, passed through an activated carbon/cotton plug, dripped into cold either, and left to stir for 30 min. The product precipitate was then collected via vacuum filtration and washed with ether and petroleum ether. All collected final products were analyzed with HPLC to verify purities at above 95%.

Example 7

Preparation of 1-(5-chloro-6-((4-(2-hydroxypropyl)-1H-1,2,3-triazol-1-yl)sulfonyl)indolin-1-yl)ethan-1-one

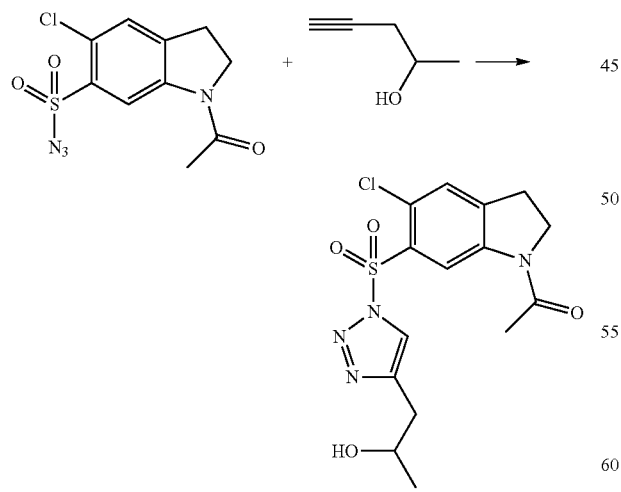

A solution of copper(I)-thiophene-2-carboxylate (CuTC, 9.4 mg, 0.0498 mmol), 4-pentyn-2-ol (36.3 μL, 0.415 mmol), and 1-acetyl-5-chloroindoline-6-sulfonyl azide (100 mg, 0.332 mmol) in DCM (1.14 mL) was stirred at room temperature for 2.5 h, and then for 15 minutes at 55° C. The reaction was then diluted with NH$_4$Cl (2 mL) and left to stir for 30 minutes. 2 mL of petroleum ether were then added, and product was vacuum filtered and washed with petroleum ether. 49.3 mg crude fine blue powder were collected, which was found to possess NH$_4$Cl. Product was then washed with 10% citric acid and water and dried overnight, which yielded a beige powder (21.0 mg, 16.5%). $^1$H NMR (500 MHz, DMSO) δ 8.922 (s, 1H), 8.922 (s, 1H), 8.647 (s, 1H), 7.635 (s, 1H), 4.754 (d, 1H, J=3.5), 4.193 (t, 2H, J=8.49), 3.942-3.897 (m, 1H), 3.259 (t, 2H, J=8.5), 2.751 (d, 2H, J=6.0), 2.206 (s, 3H). 1.055 (d. 3H, J=5.0) MP: decomposes 139.9-146.5° C. HPLC purity: 98.1% at 220.

Example 8

Preparation of 1-(5-chloro-6-((4-(2-hydroxypropan-2-yl)-1H-1,2,3-triazol-1-yl)sulfonyl)indolin-1-yl)ethan-1-one

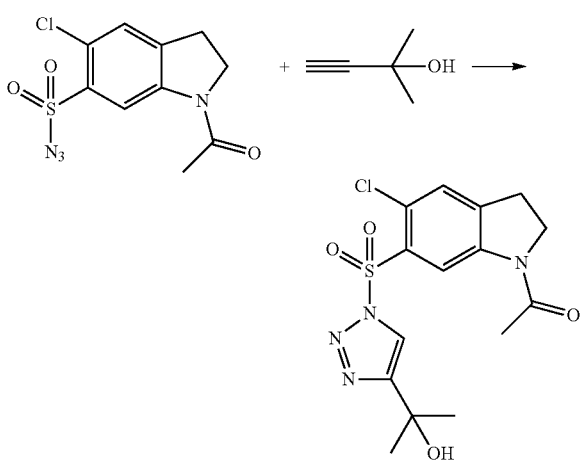

A solution of CuTC (9.4 mg, 0.0498 mmol), 2-methyl but-3-yn-2-ol (40.2 μL, 0.415 mmol), and 1-acetyl-5-chloroindoline-6-sulfonyl azide (100 mg, 0.332 mmol) in DCM (1.14 mL) was stirred at room temperature for 2 h. The reaction was then diluted with NH$_4$Cl (2 mL) and left to stir for 30 minutes, with N$_2$ blowing over the vial to remove DCM. 3 mL of ethyl ether were then added, and product was vacuum filtered and washed with petroleum ether. 74.4 mg white powder was collected (58.1%). $^1$H NMR (500 MHz, DMSO) δ 8.924 (s, 1H), 8.583 (s, 1H), 7.646 (s, 1H), 5.379 (s, 1H), 4.196 (t, 2H, J=8.7), 3.261 (t, 2H, J=8.5), 2.507-2.493 (m, 2H), 2.207 (s, 2H), 1.479 (s, 6H) MP: decomposes 145.3-147.5° C. [13C] 169.802, 155.645, 143.415, 142.770, 131.039, 128.830, 125.843, 121.636, 117.439, 66.832, 48.631, 30.137, 27.596, 23.759 HPLC purity: 95.5% at 220.

Example 8

Preparation of 1-(5-chloro-6-((4-(2-hydroxypropan-2-yl)-1H-1,2,3-triazol-1-yl)sulfonyl)indolin-1-yl)ethan-1-one

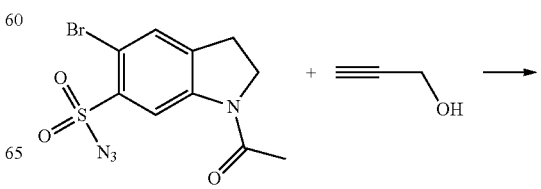

-continued

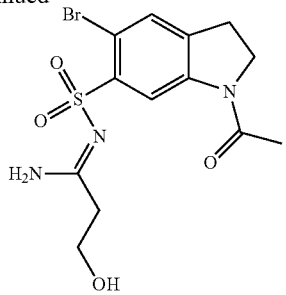

NH₄Cl (23.2 mg, 0.435 mmol), CH₂Cl₂ (970 µL), Et₃N (60.6 µL, 0.435 mmol), CuI (16.6 mg, 0.087 mmol), and propargyl alcohol (20.2 µL, 0.348 mmol) were added to 1-acetyl-5-bromoindoline-6-sulfonyl azide (100 mg, 0.290 mmol) and left to stir under N₂ for 3 h. The reaction was then diluted with 2 mL DCM and 2 mL ammonium chloride, and then stirred at room temperature under N₂ for 30 minutes. A yellow precipitate formed, which was vacuum filtered and washed with petroleum ether. About 87 mg of fine yellow (crude) powder was collected. To purify, the product was dissolved in 1.75 mL MeOH and 150 µL DMF, which was filtered into 100 mL of cold ethyl ether. Recrystallization yielded a white powder (58.6 mg, 51.8%). ¹H NMR (500 MHz, DMSO-d₆) δ 8.704 (s, 1H), 8.614 (s, 1H), 7.959 (s, 1H), 7.601 (s, 1H), 4.767 (d, 1H, J=5.0 Hz), 4.132 (t, 2H, J=8.5), 3.636 (d, 2H, J=5.0 Hz), 3.183 (t, 2H, J=8.2 Hz) 2.450 (t, 2H, J=6.2), 2.161 (s, 3H) MP: 213-218° C. HPLC purity: 94.5% at 220.

Example 9

Preparation of N-CBz-(N-Acyl)-7-Sulfonamide Indolines

To a solution of chlorosulfonyl isocyanate (1.80 mL, 18.4 mmol) in nitroethane (32 mL) cooled to −42° C. was added indoline 1 slowly drop wise with stirring. The intermediate precipitated and turned cloudy and white, and the mixture was slowly warmed to room temperature over one hour with continued stirring. Aluminum chloride (2.45 g, 18.4 mmol) was added in one portion and allowed to stir for 15 minutes at room temperature. The solution went from cloudy and white to a clear, pale yellow solution to a light purple to a dark purple over this time period. The reaction was then heated to 110° C. for one hour. The mixture was cooled to room temperature and quenched by pouring into ice water slowly where a black precipitate formed. The solid was isolated by filtering via vacuum filtration. A dark gray clay-like substance was obtained and dried overnight via vacuum yielding the cyclic sulfonyl urea indoline 3 (58-83%) as a dark gray solid compound. The solid was not purified and taken into the next reaction. ¹H NMR (300 MHz, DMSO D₆) δ 7.55 (2H, t), 7.22 (1H, t), 4.18 (2H, t), 3.35 (2H, t). See Phillips, D.; Sonnenberg, J.; Arai, A. C.; Vaswani, R.; Krutzik, P. O.; Kleisli, T.; Kessler, M.; Granger, R.; Lynch, G.; Chamberlin, A. R. *Bioorg. Med. Chem.* 2002, 10, 1229-1248.

A solution of the cyclic sulfonyl urea indoline 3 in 50% sulfuric acid was heated to 135° C. for two hours. The reaction was cooled to room temperature and then neutralized carefully with a 10 N NaOH solution while over ice. The aqueous layer was extracted with ethyl acetate three times and the organic fractions were combined and dried over magnesium sulfate and concentrated in vacuum yielding the hydrolyzed 7-sulfonamide indoline 4 as a light brown needle like solid (50%). Id.

To a round bottom flask was added 7-sulfonamide indoline 4 (1 eq) in THF (0.17M), followed by NaHCO₃ (11 eq)

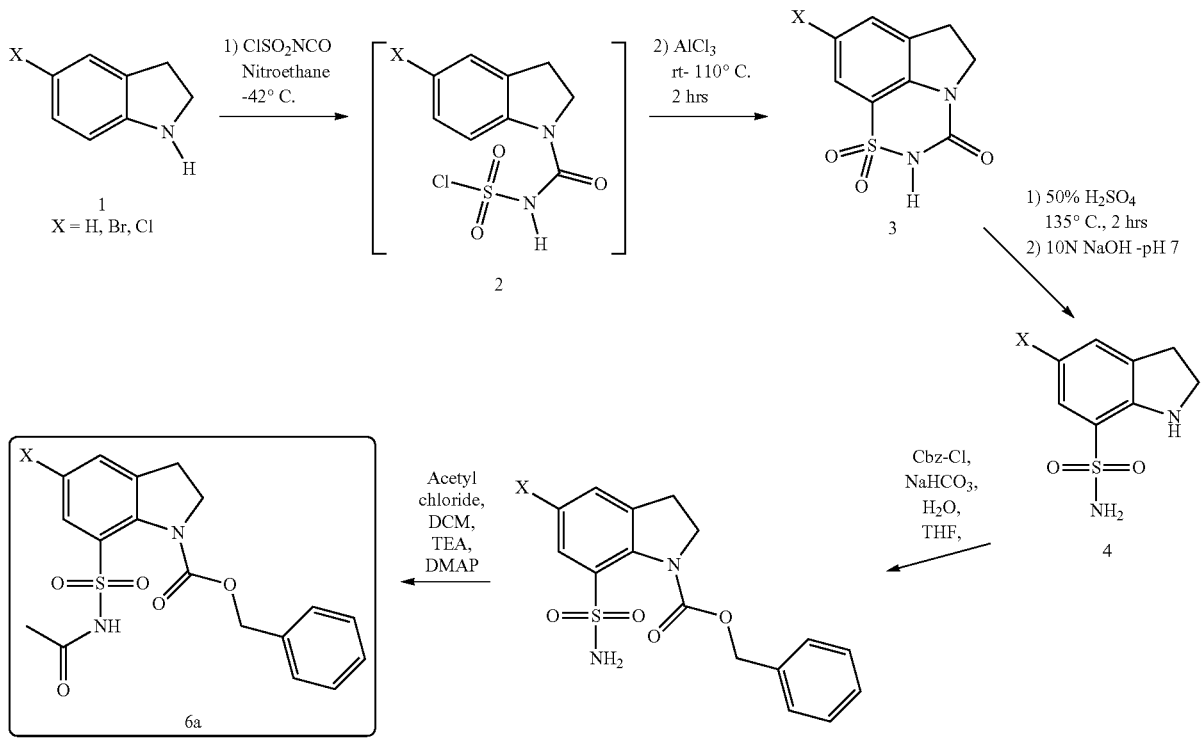

and water (1.76M). The round bottom flask was sealed and flushed with N₂ gas. To this sealed mixture was added benzyl chloroformate (3.8 eq) slowly over a few minutes by syringe. After complete addition the reaction was allowed to stir at room temperature overnight. The reaction was diluted with ethyl acetate and filtered to remove undissolved excess NaHCO₃. The organic portion was acidified with 6M HCl. The aqueous portions were further extracted with ethyl acetate two times. The organic fractions were combined and washed with brine and dried over NaSO₄ and concentrated giving a greasy off white solid. 4 mL of Et₂O was added along with 2 mL of petroleum ether, and the white solid was collected via vacuum filtration and further washed with pet ether and placed on high vac to fully dry. This reaction yields 62% white, light fluffy and pure white solid.

A solution of acetyl chloride (1.25 eq acid chloride) dissolved in dichloromethane was cooled to 0° C. To a separate solution of dichloromethane and trimethylamine (1.5 eq) was added the N-Cbz 7-sulfonamide indoline 5. The sulfonamide remained suspended in the solution until 10% mol of DMAP was added. The mixture was heated until all materials dissolved and then placed on ice to cool to 0° C. The first solution of the acid chloride was added to the sulfonamide solution slowly drop wise with stirring over 10 minutes making sure to keep the solution cool. After complete addition the reaction was allowed to warm to room temperature and stir until completion as determined by HPLC. The solution was then quenched with water and extracted with dichloromethane. The organic portions were washed one time with 1M HCl, once with water and once with brine. The solution was then dried over Na₂SO₄ and solvent was removed via rotovap (Yield 94.2%, 97% purity by HPLC). Product N-Carboxylbenzyl (N-acetyl) 7-sulfonamide indoline 6a was recrystallized in MeOH.

Examples of N-carboxybenzyl (N-acetyl) 7-sulfonamide indoline compounds synthesized by the above method include:

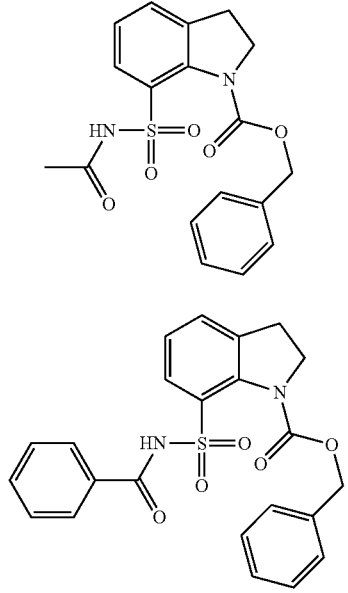

6a

6b

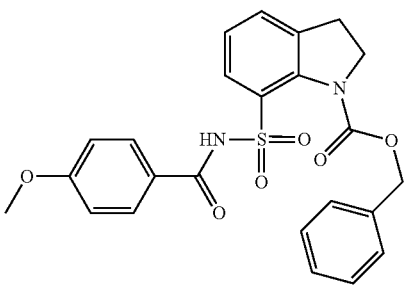

6c

Example 10

Preparation of 7-Sulfonamide Indolines by Direct Introduction of Sulfonamide

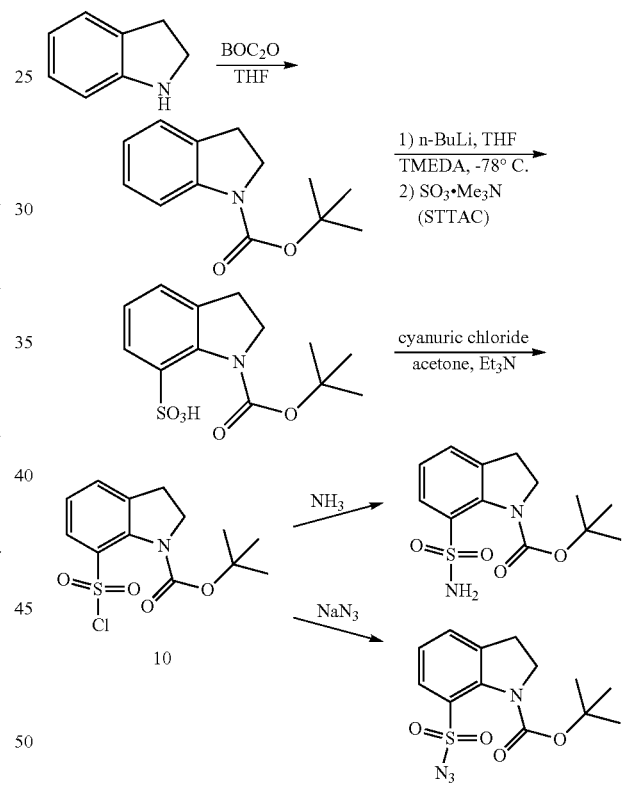

To a round bottom flask fitted with a magnetic stir bar and rubber septum was added indoline (1 eq, 16.8 mmol). The flask was flushed with N₂ gas for 3 minutes, and anhydrous THF (0.4M) was added via syringe. To this solution was added a mixture of 15 mL of anhydrous THF and ditertbutyl dicarbonate (1.1 eq, 18.5 mmol) slowly with continued stirring. A continuous evolution of gas CO₂ gas emerged. After every ¼ portion was added, the excess gas formed was removed via syringe to relieve pressure. After complete addition, the syringe was rinsed with 2 mL of THF and added to the flask. The reaction was allowed to stir 24 hours, after which it was quenched by addition of 20 mL of water. The aqueous layer was extracted with ethyl acetate. The organic portions were combined and washed with 2M HCl and brine and dried over Na$_2$SO$_4$. The solution was concentrated on the rotovap, which produced a light brown/yellow oil. The reaction was ran through a silica plug and concentrated on the rotovap producing a light brown/pink colored oil. This liquid was placed on a high vacuum where light pink/white crystals started to form. The liquid was pipetted off and crystals were washed with 50/50 Et$_2$O/ Petroleum ether. The remaining liquid was allowed to stand and evaporated over several days producing N-Boc indoline 7 as light pink/white crystals. See Iwao, M.; Kuraishi, T. *Org. Synth.* 1996, 73, 85-93.

Ortho Directed Lithiation of N-Boc Indoline.

In a multineck round bottom flask fitted with a stir bar was added N-Boc indoline (1 eq, 4.56 mmol) and sealed with a rubber septum and flushed with N$_2$ gas. TMEDA (1.2 eq, 5.47 mmol) was added via syringe followed by 15 mL of anhydrous THF. The solution turned clear and was submerged into a dry ice/acetone bath. After 10 minutes n-BuLi (1.2 eq, 5.47 mmol) was added slowly via syringe over 30 minutes. The transparent solution was an off light brown color. The reaction was allowed to stir for 2 hours while being kept at −78° C.

C-Li Insertion of STTAC (Sulfur Trioxide Trimethyl Amine Complex).

After 2 hours, a second round bottom flask was fitted with a stir bar and septum and was added STTAC (sulfur trioxide trimethyl amine complex 1 eq, 4.56 mmol) and anhydrous THF and placed in dry ice/acetone bath at −78° C. To this mixture was added the previous lithiated N-Boc indoline dropwise over 15 minutes. The mixture was allowed to stir another 2 hours at −78° C. and allowed to slowly warm to room temperature over 18 hours. The reaction was concentrated and water and 3M KOH (1 eq, 4.56 mmol) was added to the mixture, which was then extracted with Et$_2$O (2×) to remove unreacted material. The aqueous solution was evaporated to a light brown/off white solid. The solid was dissolved with 6M HCl (8 eq) and extracted 4 times with ethyl acetate and the organic fractions were combined and dried over MgSO$_4$. The solvent was evaporated producing a damp brown solid to which Et$_2$O was added. After addition of Et$_2$O, a white solid precipitated and was washed further with solvent. The combined solvent was concentrated to produce the desired N-Boc 7-sulfonic acid indoline 9 (44% yield). See Smith, K.; Hou, D. *J. Org. Chem.* 1996, 61, 1530-1532.

Synthesis of 7-Sulfonyl Chloride.

To a solution of N-Boc 7-sulfonic acid indoline 9 (1 eq) and triethyl amine (1 eq) in acetone (0.5 M) was added cyanuric chloride and the mixture was heated under reflux for 20 hours. After cooling the reaction was filtered through a celite pad and solvent was removed on the rotovap to produce the N-Boc 7-sulfonyl chloride indoline 10. See Blotny, G. *Tet. Lett.* 2003, 44, 1499-1501.

N-Boc 7-sulfonyl chloride indoline 10 can be reacted with ammonia to prepare the primary sulfonamide, which may be acylated as described herein to produce N-acyl sulfonamides. Alternatively, sulfonyl chloride 10 may be reacted with azide, such as sodium azide, yielding the sulfonyl azide, which can be converted to compounds of type IA and IB, wherein the sulfonyl substituent is on the indoline-7-position, again through previous methods described for 6-sulfonamide indolines. These 7-sulfonamide indolines 11 can be halogenated at the 5-position (compound 12) using NCS, NBS as previously described or through other known methods. The Boc group can be removed from the 1-position by treatment with acid such as trifluoroacetic acid, then known methods are employed to produced indoline-N-amides, ureas, and carbamates.

Examples of 7-sulfonamide indolines synthesized by ortho directed lithiation of N-Boc indoline and C-Li insertion of STTAC include:

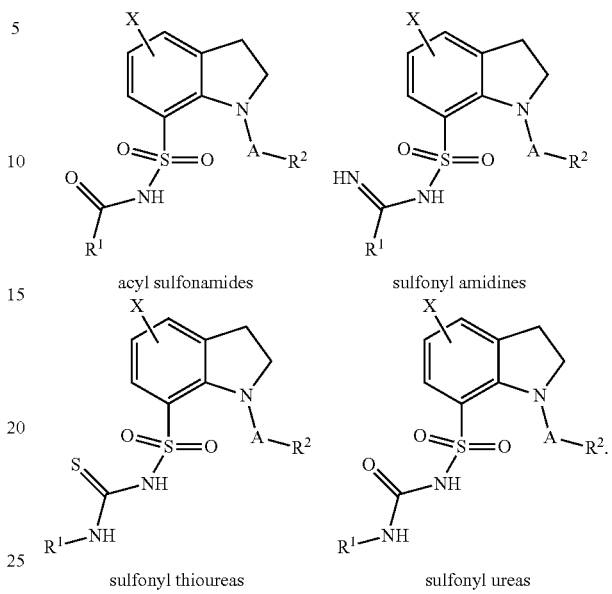

Example 11

Assay for DapE

The enzymatic activity of DapE was measured in triplicate at 570 nm by the Ruhemann's purple complex formed through the reaction of the cleaved primary amine and ninhydrin at 30° C. To 175 µL of 50 mM HEPES buffer at pH 7.5 with 5 µL of 1 µM DapE stock solution at 30° C. was added 20 µL of 10 mM monomethyl SDAP ((2S,6S)-2-(3-carboxypropanamido)-6-(methylamino)heptanedioic acid) TFA salt. The reaction was allowed to proceed for 10 minutes and quenched by heating at 100° C. for 1 minute and subsequently cooling on ice for 1 minute. To the cooled reaction was added 2% ninhydrin reagent in 100% DMSO (final volume 300 µL) and subsequently heated to 80° C. for 15 minutes. This was quenched by placing in ice water for 2 minutes, and the absorbance of 80 µL was read at 570 nm via a microplate reader. These reactions were set as 100% standard enzyme activity of DapE. Glutamic acid of concentrations 0 mM, 0.02 mM, 0.04 mM, 0.06 mM, 0.08 mM, 0.1 mM, 0.2 mM, 0.4 mM, 0.6 mM, 0.8 mM, 1.0 mM was used as a standard control of primary amine to compare enzyme activity. Results can be found in the table, below.

| Concentration (µM) | Absorbance |
| --- | --- |
| 0 | 0.1 |
| 50 | 0.283 |
| 100 | 0.48 |
| 200 | 0.82 |
| 400 | 1.644 |
| 600 | 2.454 |
| 800 | 3.154 |
| 1000 | 3.977 |
| 1500 | overflow |

The IC$_{50}$ of the inhibitors described herein can be determined using captopril as the standard. To a reaction mixture in 50 mM at pH 7.5 HEPES buffer, containing DapE (0.25

μM), a solution of the inhibitor is added. Next, the reaction mixture is allowed to incubate for 10 minutes. Following, 1 mM of alpha-N-monomethylated SDAP substrate, made by reductive amination of the SDAP substrate with aqueous formaldehyde and sodium cyanoborohydride, was added, and reaction was allowed to incubate for 40 min. Next, 0.33 mL of the reaction solution was transferred into another 1.7 mL Eppendorf tube, 0.166 mL of 2% Ninhydrin reagent was added to the reaction mixture, and the mixture was heated in a boiling water bath for 15 min. The water bath was cooled. The mixture was vigorously shaken and the absorbance was measured at 570 nm. The $IC_{50}$ for captopril (standard) is ca. 0.5 uM.

Example 12

Inhibition of NDM-1 Assay

The ability of the compounds described herein to inhibit NDM-1 was determined in the following way.

A Substrate Working Solution was prepared from CRHROMACEF (6 μM) and Tween-20 (0.02% v/v) in water. An Enzyme Working Solution was prepared with NDM-1 (0.5 μg/mL), Hepes (0.1 M), pH 7 and Tween-20 (0.02% v/v). An Inhibitor Working Solution was prepared from 50 mM of the inhibitor in DMSO. The final assay conditions were 1 mL, Hepes (50 mM), pH 7, Tween-20 (0.02% v/v), CHROMACEF (3 uM), Δ35 NDM-1 (0.25 μg/mL). Extra zinc was omitted from these assays because extra ZnSO4 interferes with the metal binding groups in inhibitors.

An aliquot of the Inhibitor Working Solution was added to a polystyrene disposable cuvette to achieve a final concentration of 0-50 μM (in 1 mL final). Supplemental DMSO was added to reach a final volume of 4 μL. NDM-1 Working Solution (0.05 mL) was added to the cuvette and the inhibitor and enzyme were allowed to incubate for about 20 minutes. The reaction was initiated by added 0.5 mL Substrate Working Solution. The solution was mixed quickly, but gently to avoid bubble formation. CHROMACEF 6 M was recorded to start the reaction. The reaction was mixed fast, but gently. The change in absorbance $\Delta\Delta Abs_{442nm/min}$ was measured for each inhibitor from the linear slope from each inhibitor concentration.

The activity for some of the compounds disclosed herein is provided below.

| Structure | Activity w/200 uM [I] | Activity w/100 uM [I] |
|---|---|---|
| (phthalimide-CH2-C6H4-COOH) | 38% | 54% |
| MM-86 | 46% | 63% |
| (HO-C(CH3)2-CH2-C(=N-SO2-indoline)-NH2 derivative) | 6.4% | 26% |
| (cyclohexanol-triazole-SO2-bromoindoline derivative) | 53% | 53% |

-continued

| Structure | Activity w/200 uM [I] | Activity w/100 uM [I] |
|---|---|---|
| MM-94 | 35% | 96% |

Example 13

Data for Select Compounds of the Disclosure

| Compound | $IC_{50}$ μM* | NDM-1 % Inhibition | NDM-1 $IC_{50}$ | DapE $IC_{50}$ |
|---|---|---|---|---|
| | 1 | 99.0% at 50 μM; 78.3% at 5 μM | | |
| | 2.0 | 77.78% at 5 μM | | |
| | 2.6 | 98.48% at 25 μM, 75.40% at 5 μM | 2.62 +/− 0.16; Hill = 1.455 +/− 0.12 | |

-continued

| Compound | IC$_{50}$ μM* | NDM-1 % Inhibition | NDM-1 IC$_{50}$ | DapE IC$_{50}$ |
|---|---|---|---|---|
| (5-chloro-indoline sulfonyl vinyl amine with phenyl hydroxyl substituent, N-acetyl) | 3 | 96.9% at 50 μM; 58.4% at 5 μM | | |
| (5-bromo-indoline sulfonyl amidine with hydroxypropyl, N-acetyl) | 9.0 | 90.27% at 50 uM, 53.97% at 10 μM | | |
| (5-bromo-indoline sulfonyl amidine with pyridylmethyl, N-acetyl) | 14.0 | 96.96% at 50 μM, 42.86% at 10 μM | | |
| (5-bromo-indoline sulfonyl amidine with 2-hydroxy-2-methylpropyl, N-acetyl) | 22.0 | 93.6% at 200 μM, 74% at 100 μM | Ki = 6.0 μM; IC$_{50}$ = 22.0 (1.0 μM); Hill = 1.0 ± 0.1 | |
| (5-bromo-indoline sulfonyl N-methyl amidine with 2-hydroxy-2-methylpropyl, N-acetyl) | 49.0 | 54.41 at 50 μM | | |

-continued

| Compound | IC$_{50}$ μM* | NDM-1 % Inhibition | NDM-1 IC$_{50}$ | DapE IC$_{50}$ |
|---|---|---|---|---|
| (structure: 5-Br, 1-acetyl-indoline-6-sulfonyl-N=C(NH$_2$)-CH$_2$-C(OH)(cyclopentyl)) | 55.0 | 64.63% at 200 μM, 41.95% at 50 μM | | |
| (structure: 5-Br, 1-acetyl-indoline-6-sulfonyl-N=C(NH$_2$)-CH$_2$-C(OH)(cyclohexyl)) | 60.0 | 34.95 at 50 μM, | | |
| (structure: 5-Cl, 1-acetyl-indoline-6-sulfonyl-N=C(NH$_2$)-CH$_2$-C(OH)(CH$_3$)$_2$) | 80.0 | 32.7% at 50 μM; 19.9% at 5 μM | | |
| (structure: 5-Br, 1-acetyl-indoline-6-sulfonyl-N=C(NH$_2$)-CH$_2$-Ph) | 110.0 | 73.8% at 200; 55.5% at 100 μM | IC$_{50}$ = 110 ± 20; Hill = 0.7 ± 0.1 | |
| (structure: 5-Br, 1-acetyl-indoline-6-sulfonyl-NH-C(=O)-CH$_2$-C(OH)(CH$_3$)$_2$) | 8.7 | 93.01% at 50 μM, 62.70% at 10 μM | 8.74 +/− 0.54; Hill = 1.95 +/− 0.22 | |

-continued

| Compound | IC$_{50}$ μM* | NDM-1 % Inhibition | NDM-1 IC$_{50}$ | DapE IC$_{50}$ |
|---|---|---|---|---|
| (5-Cl indoline sulfonamide with 3-hydroxy-3-phenylpropanamide, N-acetyl) | 100 | 31.9% at 50 μM; 15.5% at 5 μM | | |
| (5-Br indoline sulfonamide with 3-hydroxy-3-phenylpropanamide, N-acetyl) | 100 | 28.8% at 50 μM; 8.1% at 5 μM | | |
| (indoline sulfonamide with acetamide, N-acetyl) | 300.0 | 34.04% at 200 μM, 10.01% at 50 μM | | |
| (5-F indoline sulfonamide with 3-hydroxy-3-phenylpropanamide, N-acetyl) | | 12.8% (Tr1), 13.7% (Tr2) at 50 μM; 23.0% (Tr1), 0.9% (Tr2) at 5 μM | | |

-continued

| Compound | IC$_{50}$ μM* | NDM-1 % Inhibition | NDM-1 IC$_{50}$ | DapE IC$_{50}$ |
|---|---|---|---|---|
| (5-bromo-1-acetyl-indoline-6-sulfonamide with N-acetyl) | | 18% at 500 μM | | |
| (5-bromo-1-acetyl-indoline-6-sulfonyl triazole with C(CH$_3$)(H)OH) | 2.9 | 95.14% at 25 μM, 73.81% at 5 μM | 2.91 +/− 0.24; Hill = 1.39 +/− 0.11 | |
| (5-bromo-1-acetyl-indoline-6-sulfonyl triazole with C(CH$_3$)$_2$OH) | 100.0 | 47% at 200 μM, 47% at 100 μM | IC$_{50}$ = 100 ± 10; Hill = 0.4 ± 0.05 | |
| (5-bromo-1-acetyl-indoline-6-sulfonyl triazole with phenyl) | | 25% at 100 μM | | |

*estimated or actual from a single point

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step that is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps. All patents, publications and references cited herein are hereby fully incorporated by reference. In case of conflict between the present disclosure and incorporated patents, publications and references, the present disclosure should control.

What is claimed:

1. A compound having a structure of Formula (I), or a pharmaceutically acceptable salt thereof:

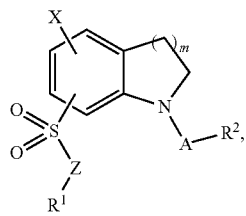

(I)

wherein
m is 1 or 2;
A is C=O or SO$_2$;
X is C$_{1-6}$alkyl, halo, OH, C$_{1-6}$alkoxy, aryl, or heteroaryl having 1, 2, 3, or 4 heteroatoms selected from N, O, and S;
Z is

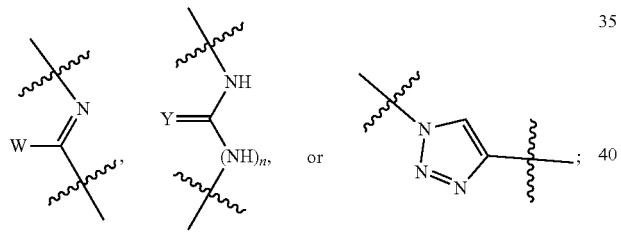

n is 0;
W is NR$^3$R$^4$ or OR$^7$;
Y is O, S, or NR$^6$;
R$^1$ is C$_{1-6}$alkyl, C$_{2-6}$alkenyl, C$_{1-4}$alkylene-OH, C$_{1-4}$alkylene-CN, C$_{1-4}$alkylene-halo, C$_{1-4}$alkylene-NR$^6$$_2$, C$_{0-4}$alkylene-R$^5$, C$_{1-4}$alkylene-C(=O)R$^5$, C$_{1-4}$alkylene-C(=O)OR$^5$, C$_{1-4}$alkylene-NHC(O)R$^6$, C$_{1-4}$alkylene-NHC(O)OR$_5$, C$_{1-4}$alkylene-C(=NOR$^6$)R$^5$, or C$_{1-4}$alkylene-OSO$_2$R$^5$;
R$^2$ is C$_{1-6}$alkyl, C$_{2-6}$alkenyl, C$_{1-4}$alkylene-CN, C$_{1-4}$alkylene-halo, C$_{0-4}$alkylene-R$^5$, C$_{0-4}$alkylene-OR$^5$, or C$_{1-4}$alkylene-SO$_2$R$^5$;
R$^3$ and R$^4$ are each independently H, C$_{1-4}$alkyl, C$_{0-4}$alkylene-C(O)C$_{1-4}$alkyl, C$_{0-4}$alkylene-CO$_2$R$^6$, C$_{0-4}$alkylene-NR$^6$$_2$, C$_{0-4}$alkylene-C$_{3-6}$cycloalkyl, C$_{0-4}$alkylene-C$_{3-6}$heterocycloalkyl having 1, 2, or 3 heteroatoms selected from N, O and S, or C$_{0-4}$alkylene-C$_{6-10}$aryl, or R$^3$ and R$^4$ are taken together with the nitrogen to which they are attached to form a 5-7 membered ring;
R$^5$ is H, C$_{1-6}$alkyl, C$_{2-6}$alkenyl, C$_{0-4}$alkylene-C$_{3-6}$cycloalkyl, C$_{0-4}$alkylene-C$_{3-6}$heterocycloalkyl having 1, 2, or 3 heteroatoms selected from N, O and S, C$_{0-4}$alkylene-C$_{6-10}$aryl, C$_{2-4}$alkenylene-C$_{6-10}$aryl, C$_{0-4}$alkylene-C$_{5-10}$heteroaryl having 1, 2, 3, or 4 heteroatoms selected from N, O, and S, or NR$^3$R$^4$;
each R$^6$ independently is H or C$_{1-3}$alkyl; and
R$^7$ is H, C$_{1-6}$alkyl, C$_{0-4}$alkylene-C$_{6-10}$aryl, or C$_{0-4}$alkylene-C(O)-C$_{1-4}$alkylene-NR$^6$$_2$.

2. The compound of claim 1, wherein m is 1.
3. The compound of claim 1, wherein A is C=O.
4. The compound of claim 1, wherein Z is

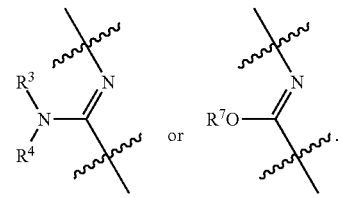

5. The compound of claim 4, wherein R$^3$ and R$^4$ are each independently selected from the group consisting of H,

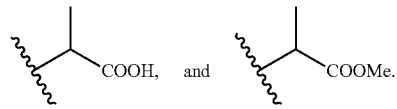

6. The compound of claim 4, wherein each of R$^3$, R$^4$, and R$^7$ is H.
7. The compound of claim 1, wherein Z is

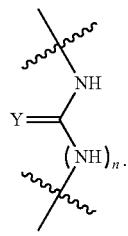

8. The compound of claim 7, wherein Y is O or S.
9. The compound of claim 7, wherein Y is NH.
10. The compound of claim 1, wherein Z is

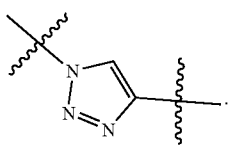 [SMILES: *c1cn(*)nn1]

11. The compound of claim 1, wherein X is F, Cl, Br, I, CH$_3$, CF$_3$, OCH$_3$, or OCF$_3$.
12. The compound of claim 1, wherein R$^1$ is selected from the group consisting of:

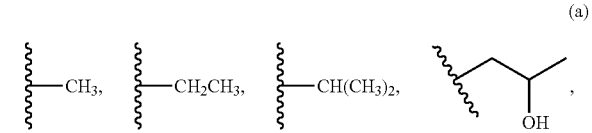

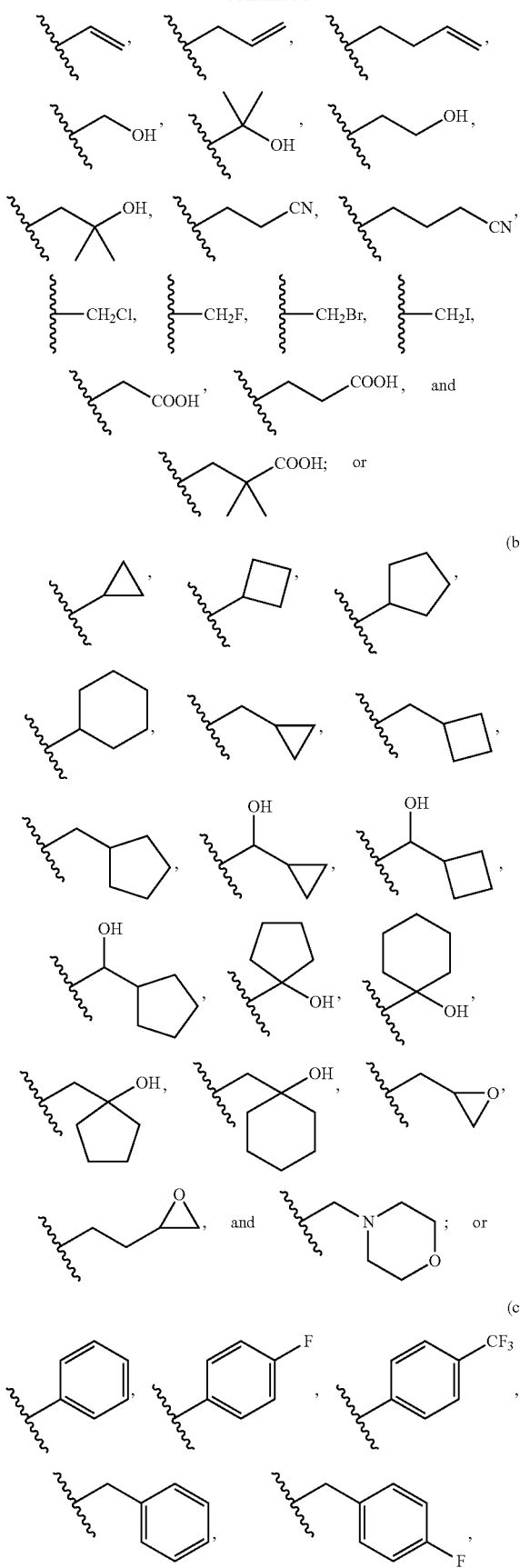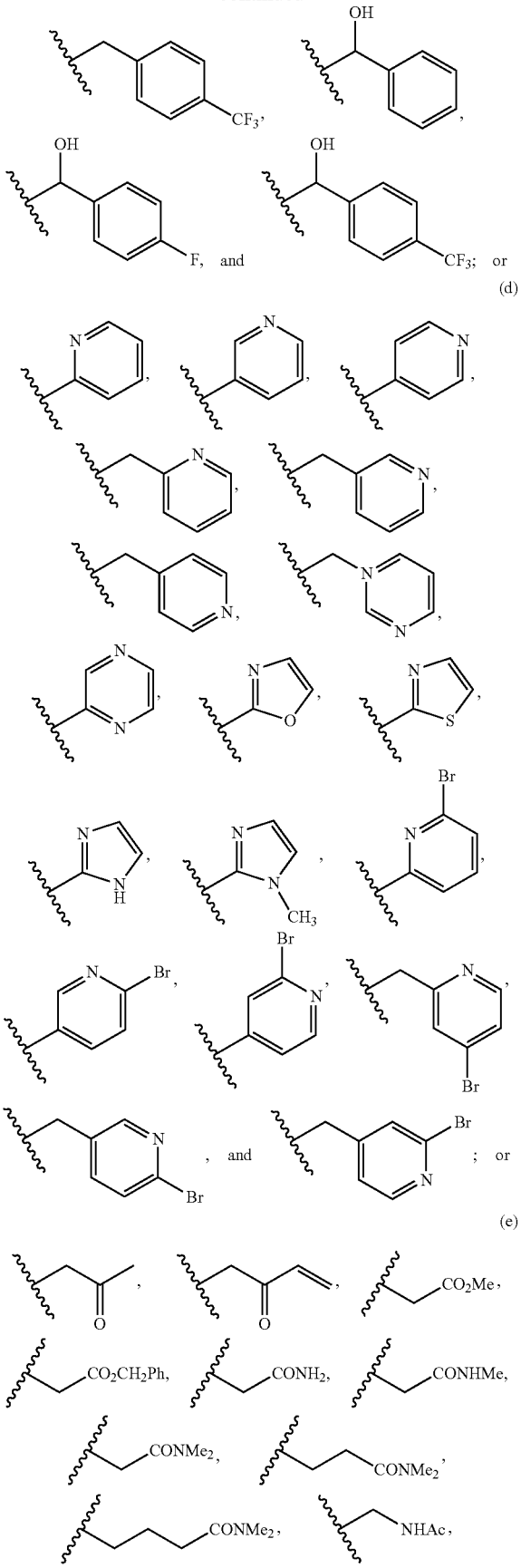

(f) CH₂OSO₂CH₃, CH₂OSO₂CF₃, CH₂OSO₂Ph, and CH₂OSO₂PhCH₃.

13. The compound of claim 1, wherein R² is selected from the group consisting of:

14. A compound having a structure selected from the group consisting of:

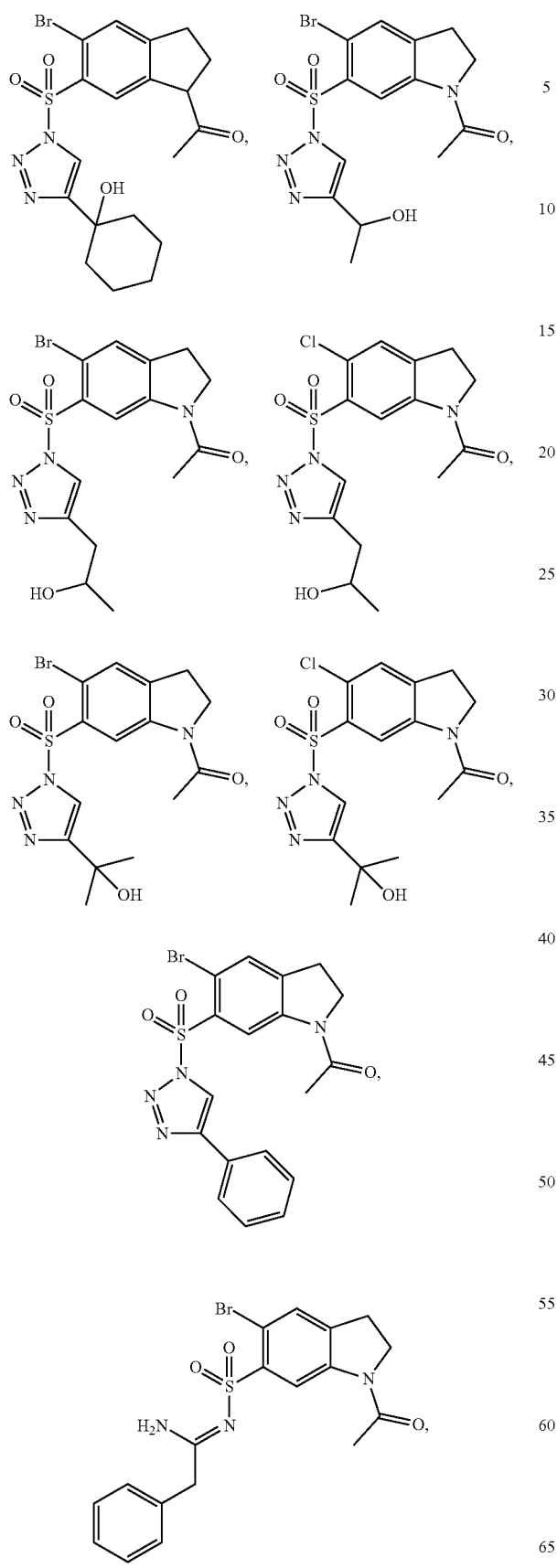
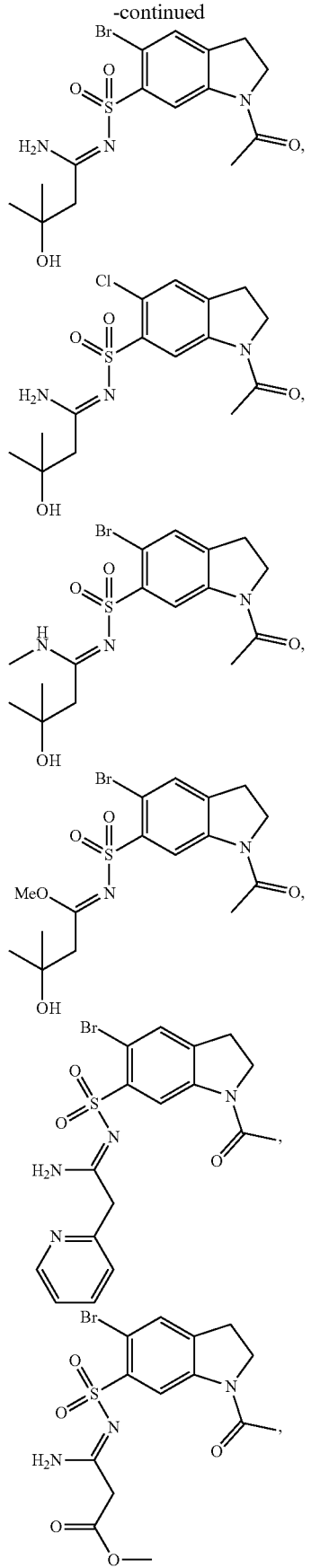
-continued

95
-continued
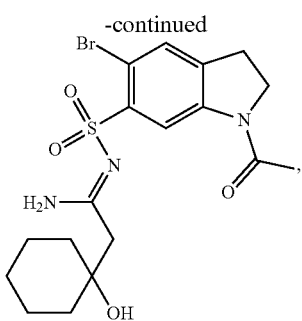
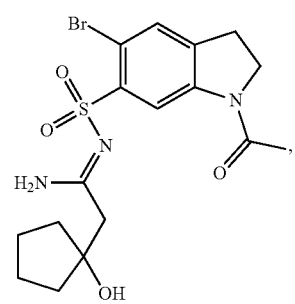
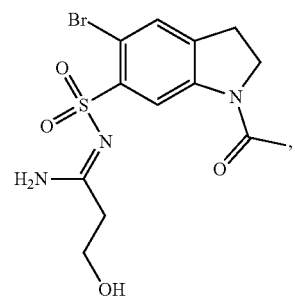
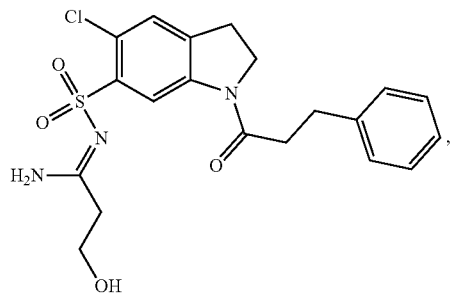
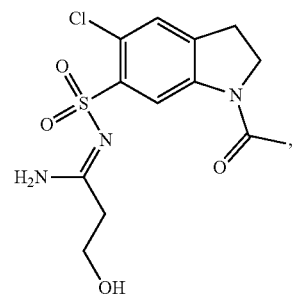
96
-continued
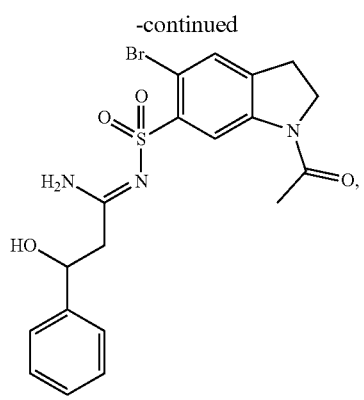
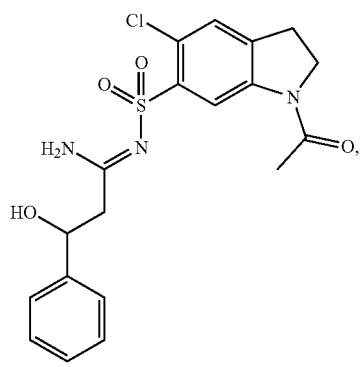
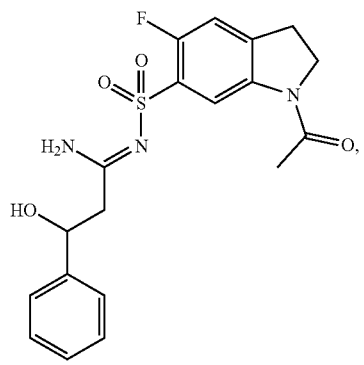
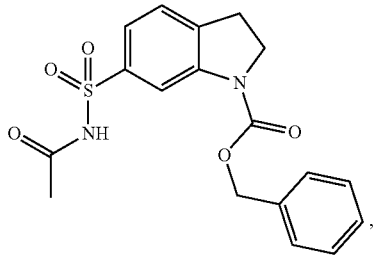
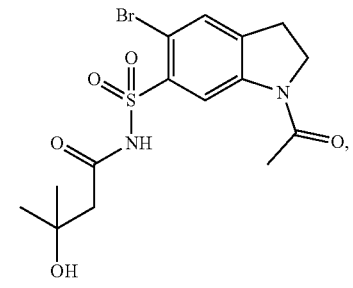

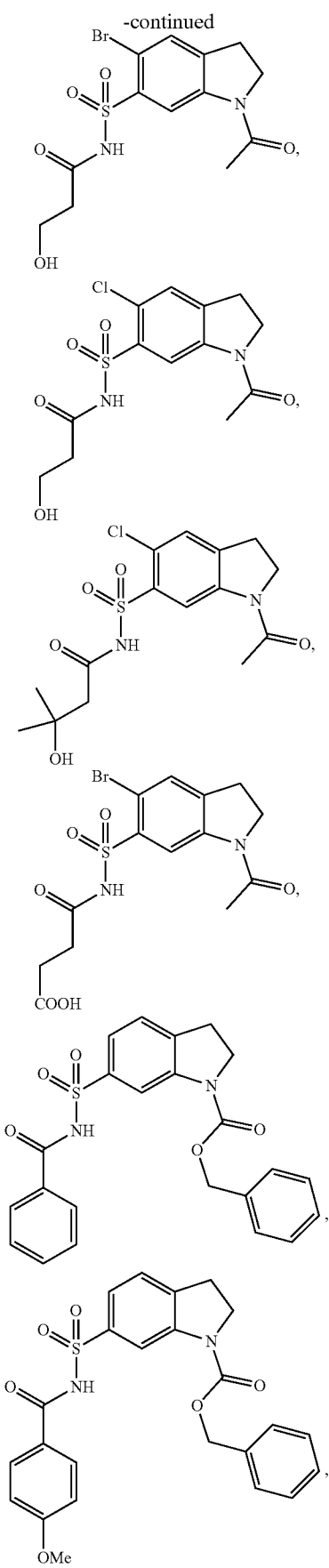
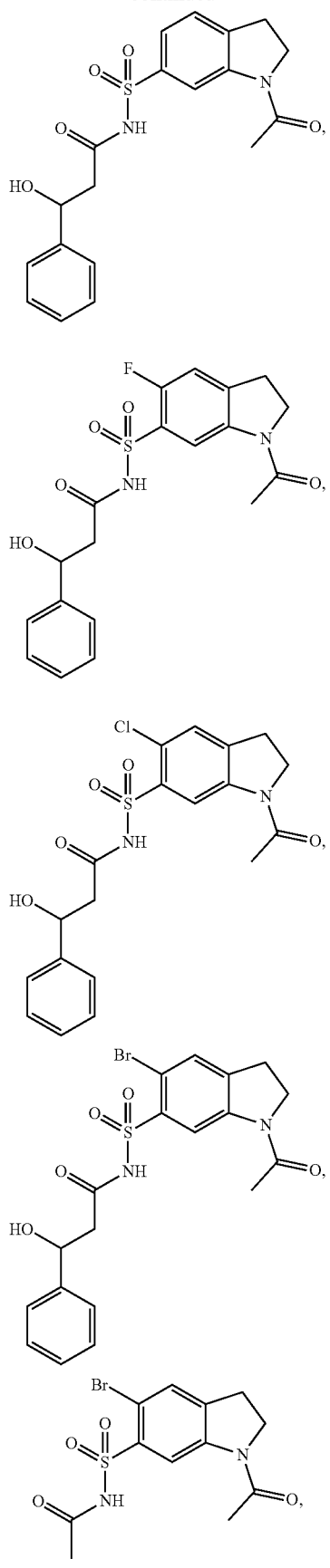

15. A pharmaceutical composition comprising a compound of claim 1, and a pharmaceutically acceptable carrier or vehicle.

16. A method of reducing, or ameliorating a disease or condition, and/or symptoms associated therewith, mediated by inhibition of MBL or DapE comprising administering to an individual in need thereof a therapeutically effective amount of a compound having a structure of Formula (I), or a pharmaceutically acceptable salt thereof:

wherein
m is 1 or 2;
A is C=O or $SO_2$;
X is H, $C_{1-6}$alkyl, halo, OH, $C_{1-6}$alkoxy, aryl, or heteroaryl having 1, 2, 3, or 4 heteroatoms selected from N, O, and S;
Z is n is 0 or 1;
W is $NR^3R^4$ or $OR^7$;
Y is O, S, or $NR^6$;
$R^1$ is $C_{1-6}$alkyl, $C_{2-6}$alkenyl, $C_{1-4}$alkylene-OH, $C_{1-4}$alkylene-CN, $C_{1-4}$alkylene-halo, $C_{1-4}$alkylene-$NR^6_2$, $C_{0-4}$alkylene-$R^5$, $C_{1-4}$alkylene-C(=O)$R^5$, $C_{1-4}$alkylene-C(=O)O$R^5$, $C_{1-4}$alkylene-NHC(O)$R^5$, $C_{1-4}$alkylene-NHC(O)O$R_5$, $C_{1-4}$alkylene-C(=NO$R^6$)$R^5$, or $C_{1-4}$alkylene-OSO$_2R^5$;
$R^2$ is $C_{1-6}$alkyl, $C_{2-6}$alkenyl, $C_{1-4}$alkylene-CN, $C_{1-4}$alkylene-halo, $C_{0-4}$alkylene-$R^5$, $C_{0-4}$alkylene-O$R^5$, or $C_{1-4}$alkylene-SO$_2R^5$;
$R^3$ and $R^4$ are each independently H, $C_{1-4}$alkyl, $C_{0-4}$alkylene-C(O)$C_{1-4}$alkyl, $C_{0-4}$alkylene-CO$_2R^6$, $C_{0-4}$alkylene-$NR^6_2$, $C_{0-4}$alkylene-$C_{3-6}$cycloalkyl, $C_{0-4}$alkylene-$C_{3-6}$heterocycloalkyl having 1, 2, or 3 heteroatoms selected from N, O and S, or $C_{0-4}$alkylene-$C_{6-10}$aryl, or $R^3$ and $R^4$ are taken together with the nitrogen to which they are attached to form a 5-7 membered ring;
$R^5$ is H, $C_{1-6}$alkyl, $C_{2-6}$alkenyl, $C_{0-4}$alkylene-$C_{3-6}$cycloalkyl, $C_{0-4}$alkylene-$C_{3-6}$heterocycloalkyl having 1, 2, or 3 heteroatoms selected from N, O and S, $C_{0-4}$alkylene-$C_{6-10}$aryl, $C_{2-4}$alkenylene-$C_{6-10}$aryl, $C_{0-4}$alkylene-$C_{5-10}$heteroaryl having 1, 2, 3, or 4 heteroatoms selected from N, O, and S, or $NR^3R^4$;
each $R^6$ independently is H or $C_{1-3}$alkyl; and
$R^7$ is H, $C_{1-6}$alkyl, $C_{0-4}$alkylene-$C_{6-10}$aryl, or $C_{0-4}$alkylene-C(O)-$C_{1-4}$alkylene-$NR^6_2$.

17. The method of claim 16, wherein the MBL is NDM-1.

18. The method of claim 16, wherein the disease or condition is a bacterial infection.

19. The method of claim 16 further comprising administering a therapeutically effective amount of a second therapeutic agent useful in the treatment of the disease or condition, optionally wherein the second therapeutic is a δ-lactam antibiotic.

* * * * *

UNITED STATES PATENT AND TRADEMARK OFFICE
CERTIFICATE OF CORRECTION

| | | |
|---|---|---|
| PATENT NO. | : 10,626,087 B2 | Page 1 of 1 |
| APPLICATION NO. | : 15/742947 | |
| DATED | : April 21, 2020 | |
| INVENTOR(S) | : Daniel Paul Becker et al. | |

It is certified that error appears in the above-identified patent and that said Letters Patent is hereby corrected as shown below:

In the Claims

At Column 87, Line 51, "$C_{1-4}$alkylene-NHC(O)R$^6$," should be -- $C_{1-4}$alkylene-NHC(O)R$^5$, --.

At Column 90, Line 25, " 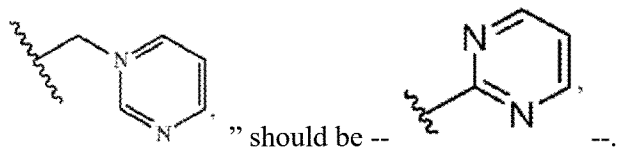 " should be -- --.

At Column 95, Lines 43-53, " 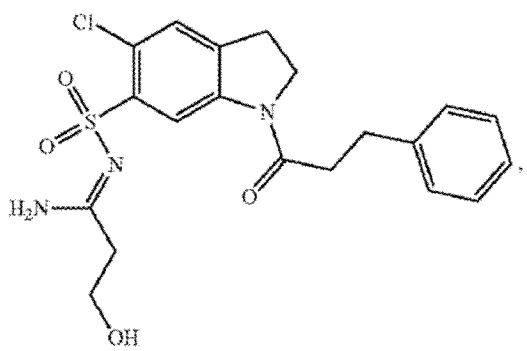 " should be

-- 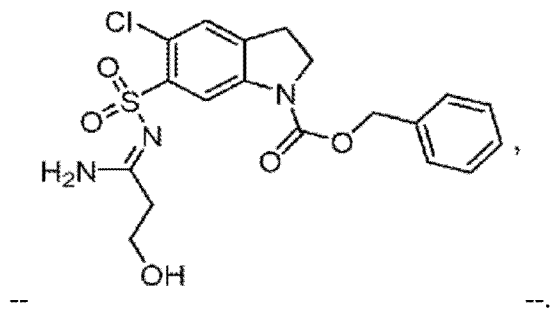 --.

Signed and Sealed this
Twenty-second Day of September, 2020

Andrei Iancu
*Director of the United States Patent and Trademark Office*